US009428780B2

(12) United States Patent
Baldwin et al.

(10) Patent No.: US 9,428,780 B2
(45) Date of Patent: *Aug. 30, 2016

(54) EXPRESSION OF GRANULAR STARCH HYDROLYZING ENZYMES IN TRICHODERMA AND PROCESS FOR PRODUCING GLUCOSE FROM GRANULAR STARCH SUSTRATES

(71) Applicant: Danisco US Inc., Palo Alto, CA (US)

(72) Inventors: Toby M. Baldwin, Palo Alto, CA (US); Benjamin S. Bower, Newark, CA (US); Gopal K. Chotani, Cupertino, CA (US); Nigel Dunn-Coleman, Los Gatos, CA (US); Oreste J. Lantero, Belvidere, IL (US); Suzanne Lantz, San Carlos, CA (US); Michael J. Pepsin, Castro Valley, CA (US); Jayarama K. Shetty, Palo Alto, CA (US); Bruce A. Strohm, Beloit, WI (US)

(73) Assignee: Danisco US Inc., Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/688,283

(22) Filed: Apr. 16, 2015

(65) Prior Publication Data

US 2015/0284756 A1 Oct. 8, 2015

Related U.S. Application Data

(60) Continuation of application No. 13/664,216, filed on Oct. 30, 2012, now abandoned, which is a continuation of application No. 13/230,707, filed on Sep. 12, 2011, now Pat. No. 8,323,932, which is a continuation of application No. 11/875,279, filed on Oct. 19, 2007, now Pat. No. 8,034,590, which is a division of application No. 10/991,654, filed on Nov. 18, 2004, now Pat. No. 7,303,899.

(60) Provisional application No. 60/524,279, filed on Nov. 21, 2003, provisional application No. 60/531,953, filed on Dec. 22, 2003, provisional application No. 60/566,358, filed on Apr. 28, 2004.

(51) Int. Cl.
| | |
|---|---|
| *C12P 19/14* | (2006.01) |
| *C12N 1/14* | (2006.01) |
| *C12N 9/30* | (2006.01) |
| *C12N 9/34* | (2006.01) |
| *C12P 19/20* | (2006.01) |
| *C12P 19/24* | (2006.01) |
| *C12P 19/02* | (2006.01) |
| *C12P 19/04* | (2006.01) |

(52) U.S. Cl.
CPC .............. *C12P 19/14* (2013.01); *C12N 1/14* (2013.01); *C12N 9/242* (2013.01); *C12N 9/2428* (2013.01); *C12P 19/02* (2013.01); *C12P 19/04* (2013.01); *C12P 19/20* (2013.01); *C12P 19/24* (2013.01); *Y02E 50/17* (2013.01); *Y02P 20/52* (2015.11)

(58) Field of Classification Search
None
See application file for complete search history.

(56) References Cited

U.S. PATENT DOCUMENTS

| | | |
|---|---|---|
| 3,236,687 A | 2/1966 | Smith et al. |
| 3,249,514 A | 5/1966 | Bode |
| 3,912,590 A | 10/1975 | Slott et al. |
| 3,922,196 A | 11/1975 | Leach et al. |
| 4,092,434 A | 5/1978 | Yoshizumi et al. |
| 4,316,956 A | 2/1982 | Lutzen |
| 4,514,496 A | 4/1985 | Yoshizumi et al. |
| RE32,153 E | 5/1986 | Tamura et al. |
| 4,587,215 A | 5/1986 | Hirsh |
| 4,618,579 A | 10/1986 | Dwiggins et al. |
| 4,863,864 A | 9/1989 | Ashikari et al. |
| 5,028,539 A | 7/1991 | Ingram et al. |
| 5,246,853 A | 9/1993 | Clarkson et al. |
| 5,322,778 A | 6/1994 | Antrim et al. |
| 5,424,202 A | 6/1995 | Ingram et al. |
| 5,475,101 A | 12/1995 | Ward et al. |
| 5,482,846 A | 1/1996 | Ingram et al. |
| 5,487,989 A | 1/1996 | Fowler et al. |
| 5,514,583 A | 5/1996 | Picataggio et al. |
| 5,554,520 A | 9/1996 | Fowler et al. |
| 5,650,322 A | 7/1997 | Clarkson et al. |

(Continued)

FOREIGN PATENT DOCUMENTS

| | | |
|---|---|---|
| EP | 0 171 218 B1 | 10/1993 |
| EP | 0 625 577 A1 | 11/1994 |

(Continued)

OTHER PUBLICATIONS

Allison, Daniel S. et al., "Transformation of the thermophilic fungus *Humicola grisea* var. *thermoidea* and overproduction of Humicola glucoamylase." *Current Genetics*, vol. 21, pp. 225-229, 1992.

(Continued)

*Primary Examiner* — Iqbal H Chowdhury
(74) *Attorney, Agent, or Firm* — Danisco US Inc.

(57) ABSTRACT

The present invention relates to filamentous fungal host cells and particularly *Trichoderma* host cells useful for the production of heterologous granular starch hydrolyzing enzymes having glucoamylase activity (GSHE). Further the invention relates to a method for producing a glucose syrup comprising contacting a granular starch slurry obtained from a granular starch substrate simultaneously with an alpha amylase and a GSHE at a temperature equal to or below the gelatinization temperature of the granular starch to obtain a composition of a glucose syrup.

3 Claims, 15 Drawing Sheets

(56) References Cited

U.S. PATENT DOCUMENTS

| | | | |
|---|---|---|---|
| 5,665,585 | A | 9/1997 | Torkkeli et al. |
| 5,874,276 | A | 2/1999 | Fowler et al. |
| 6,022,725 | A | 2/2000 | Fowler et al. |
| 6,268,328 | B1 | 7/2001 | Mitchinson et al. |

FOREIGN PATENT DOCUMENTS

| | | |
|---|---|---|
| EP | 0 244 234 B2 | 11/2001 |
| EP | 0 215 594 B2 | 10/2003 |
| WO | WO 92/00381 | 1/1992 |
| WO | WO 92/06209 | 4/1992 |
| WO | WO 99/01545 | 1/1999 |
| WO | WO 99/28488 | 7/1999 |
| WO | WO 99/60136 | 11/1999 |
| WO | WO 00/04136 | 1/2000 |
| WO | WO 03/068976 | 8/2003 |

OTHER PUBLICATIONS

Altshul, Stephen F. et al., "Gapped BLAST and PSI-BLAST : a new generation of protein database search programs." *Nucleic Acids Research*, vol. 25, No. 17, pp. 3389-3402, 1997.

Arasaratnam, Vasanthi et al., "Synergistic Action of α-Amylase and Glucoamylase on Raw Corn." *Starch/Starke* vol. 45, No. 6, pp. 231-233, 1993.

Ashikari, Toshihiko et al., "Rhizopus Raw-Starch-Degrading Glucoamylase : Its Cloning and Expression in Yeast." *Agric. Biol. Chem.*, vol. 50, No. 4, pp. 957-964, 1986.

Bennett, J. W. et al., ed., "More Gene Manipulations in Fungi" Academic Press, San Diego, pp. 70-76, 1991.

Bhikhabhai, Ramagauri et al., "Isolation of Celluloytic Enzymes from Trichoderma reesei, QM 9414." *Journal of Applied Biochemistry*, vol. 6, pp. 336-345, 1984.

Boel, E. et al., "Glucoamylases G1 and G2 from Aspergillus niger are synthesized from two different but closely related mRNAs." *The EMBO Journal*, vol. 3, No. 5, pp. 1097-1102, 1984.

Boel, E. et al., "Two different types of intervening sequences in the glucoamylase gene from Aspergillus niger." *The EMBO Journal*, vol. 3, No. 7, pp. 1581-1585, 1984.

Brumbauer, Aniko et al., "Fractionation of cellulase and β-glucosidase in a Trichoderma reesei." *Bioseparation*, vol. 7, pp. 287-295, 1999.

Campbell, Edward I. et al., "Improved transformation efficiency of Aspergillus niger." *Current Genetics*, vol. 16, pp. 53-56, 1989.

Cao, Qing-Na et al., "Penicillopepsin-JT2, a recombinant enzyme from Penicillium janthinellum and the contribution of a hydrogen bond in subsite S3 to kcat." *Protein Science*, vol. 9, pp. 991-1001, 2000.

Cees, A. M. et al., "Heterologous Gene Expression in Filamentous Fungi." *More Gene Manipulations in Fungi*, Bennett, J.W. et al., ed., pp. 396-428, Academic Press, 1991.

Chen, Hsiu-mei et al., "Identification and elimination by site-directed mutagenesis of thermolabile aspartyl bonds in *Aspergillus awamori* glucoamylase." *Protein Engineering*, vol. 8, No. 6, pp. 575-582, 1995.

Chen, Hsiu-mei et al., "Effect of replacing helical glycine residues with alanines on reversible and irreversible stability and production of Aspergillus awamori glucoamylase." *Protein Engineering*, vol. 9, No. 6, pp. 499-505, 1996.

Chen, Frank Y. et al., "Regulation of mammalian ribonucleotide reductase R1 mRNA stability is mediated by a ribonucleotide reductase R1 mRNA 3-untranslated region cis-trans interaction through a protein kinase C-controlled pathway." *Biochem. J.*, vol. 302, pp. 125-132, 1994.

Database UniProt Online, Nov. 1, 1994, Glucoamylase. XP002325133, retrieved from EBI accession No. UNIPROT:Q12623.

Davis, Rowland H. et al., Genetic and Microbiological Research Techniques for *Neurospora crassa*, Methods in Enzymology, 17A, pp. 79-143, 1970.

Berka, R. et al., Abstract No. 45, "Cloning of a Thermostable Glucoamylase from the Thermophilic Fungus *Humicola grisea* (var. *thermoidea*) and its Expression in Aspergillus Niger. Development of a Transformation System for *H. grisea* and Use of an Automated Screening Procedure for the Isolation of Mutants of *H. grisea* with Enhanced Glucoamylase Secretion." presented at EMBO—Alko Workshop, Molecular Biology of Filamentous Fungi, Hanasaari Conference Centre, Espoo, Finland, Jul. 2-7, 1989.

Poster entitled, Cloning of a Thermostable Glucoamylase from the Thermophilic Fungus *Humicola grisea* (var. *Thermoidea*) and its Expression in Aspergillus Niger. Development of a Transformation System for *H. grisea* and Use of an Automated Screening Procedure for the Isolation of Mutants of *H. grisea* with Enhanced Glucoamylase Secretion. presented at EMBO—Alko Workshop, Molecular Biology of Filamentous Fungi, Hanasaari Conference Centre, Espoo, Finland, Jul. 2-7, 1989.

Ellouz, S. et al., "Analytical Separation of Trichoderma reesei, Cellulases by Ion-Exchange Fast Protein Liquid Chromatography." *Journal of Chromatography*, vol. 396, pp. 307-327, 1987.

Fagerstrom, Richard, "Purification and specificity of recombinant *Hormoconis resinae* glucoamylase P and endogenous glucoamylase from Trichoderma reesei, Enzyme Microb. Technol., vol. 16, pp. 36-42, 1994.".

Finkelstein, David B. et al., ed., *Biotechnology of Filamentous Fungi, Technology and Products*, Chapter 6, pp. 113-156, Butterworth-Heinemann, Boston, MA, 1992.

Fliess, A. et al., "Characterization of Cellulases by HPLC Separation." *Eur. J. Appl. Microbiol. Biotechnol.*, vol. 17, pp. 314-318, 1983.

Flor, Perfecto Q. et al., "Production and Characteristics of Raw Starch-Digesting Glucoamylase O from a Protease-Negative, Glycosidase-Negative *Aspergillus awamori* var. *kawachi* Mutant." *Applied and Environmental Microbiology*, vol. 34, No. 3, pp. 905-912, Mar. 1983.

Fujii, M et al., "Synergistic action of alpha amylase and glucoamylase on hydrolysis of starch", *Biotechnology and Bioengineering*, V. 27, NY, 1985, pp. 260-265.

Fujii, Michihiro et al., "Synergism of α-Amylase and Glucoamylase on Hydrolysis of Native Starch Granules." *Biotechnology and Bioengineering*, vol. 32, pp. 910-915, 1988.

Goedegebuur, Frits et al., "Cloning and relational analysis of 15 novel fungal endoglucanases from family 12 glycosyl hydrolase." *Current Genetics*, vol. 41, pp. 89-98, 2002.

Goto, Masatoshi et al., "The Mechanism of Binding of Glucoamylase I from *Aspergillus awamori* var. *kawachi* to Cyclodextrins and Raw Starch." *Biosci. Biotech. Biochem.*, vol. 58, No. 1, pp. 49-54, 1994.

Goyal, Anil et al., "Characteristics of Fungal Cellulases." *Bioresource Technology*, vol. 36, pp. 37-50, 1991.

Harkki, Anu et al., "Genetic engineering of Trichoderma to produce strains with novel cellulase profiles." *Enzyme Microb. Technol.*, vol. 13, pp. 227-233, Mar. 1991.

Harkki, A. et al., "A Novel Fungal Expression System : Secretion of Active Calf Chymosin from the Filamentous Fungus *Trichoderma reesei.*" *Bio/Technology*, vol. 7, pp. 596-603, Jun. 1989.

Hata, Yoji et al., "The Glucoamylase cDNA from *Aspergillus oryzae* : Its Cloning, Nucleotide Sequence, and Expression in *Saccharomyces cerevisiae.*" *Agric. Biol. Chem.*, vol. 55, No. 4, pp. 941-949, 1991.

Hayashida, Shinsaku et al. "High Concentration-Ethanol Fermentation of Raw Ground Corn." *Agric. Biol. Chem.*, vol. 46, No. 7, pp. 1947-1950, 1982.

Hayashida, Shinsaku et al., "Raw Starch-digestive Glucoamylase Productivity of Protease-less Mutant from *Aspergillus awamori* var. *kawachi.*" *Agric. Biol. Chem.*, vol. 45, No. 12, pp. 2675-2681, 1981.

Hayashida, Shinsaku et al., "Molecular Cloning of the Glucoamylase I Gene of *Aspergillus awamori* var. *kawachi* for Localization of the Raw-starch-affinity Site. " *Agric. Biol. Chem.*, vol. 53, No. 4, pp. 923-929, 1989.

Hayashida, Shinsaku et al., "Raw Starch-digestive Chitin-immobilized Amylase from a Protease-Glycosidase-less Mutant of *Aspergillus awamori* var. *kawachi.*" *Agric. Biol. Chem.*, vol. 46, No. 6, pp. 1639-1645, 1982.>>.

(56) References Cited

OTHER PUBLICATIONS

Ilmen, Marja et al., "Regulation of Cellulase Gene Expression in the Filamentous Fungus Trichoderma reesei." *Applied and Environmental Microbiology*, vol. 63, No. 4, pp. 1298-1306, 1997.
Innis, M. A. et al., "Expression, Glycosylation, and Secretion of an *Aspergillus* Glucoamylase by *Saccharomyces cerevisiae*." *Science*, vol. 228, pp. 21-26, 1985.
Jensen, Bo et al., (1988). Purification of extracellular amylotic enzymes from the thermophilic fungus *Thermomyces lanuginosus*, *Can. J. Microbiol.*, vol. 34, pp. 218-223.
Karakatsanis, A. et al., "Hydrolysis of various starches by the synergistic action of alpha-amylase and glucoamylase in aqueous two phase impeller agitated systems," *Starke-Starch*, Wiley-Vch Verlag, Weinheim, DE, V. 49, N. 5, May 1, 1997, pp. 194-199.
Kelley, Joan M. et al., Transformation of *Aspergillus niger* by the amdS gene of *Aspergillus nidulans*, *The EMBO Journal*, vol. 4, No. 2, pp. 475-479, 1985.
Kinghorn, et al., *Applied Molecular Genetics of Filamentos Fungi*, Blackie Academic and Professional, Chapman and Hall, London, 1992.
Kreigler *Gene Transfer and Expression; A Laboratory Manual.* 1990.
Liakopoulou-Kyriakides, Maria et al., "Synergistic hydrolysis of crude corn starch by alpha-amylases and glucoamylases of various origins." *Cereal Chemistry*, V. 78, N. 5, pp. 603-607, Sep. 2001.
Medve, Jozsef et al., "Ion-exchange chromatogaphic purification and quantitative analysis of *Trichoderma reesei* cellulases cellobiohydrolase I, II and endoglucanase II by fast protein liquid chromatography." *Journal of Chromatography A*, vol. 808, pp. 153-165, 1998.
Miller, Gail L., Use of Dinitrosalicyclic Acid Reagent for Determination of Reducing Sugar. *Analytical Chemistry*, vol. 31, pp. 426-428, 1959.
Nevalainen, K. M. Helena et al., "The Moleclar Biology of *Trichoderma* and Its Application to the Expression of Both Homologous and Heterologous Genes." *Molecular Industrial Mycology*, Leong and Berka, ed., Marcel Dekker, Inc., NY, pp. 129-148, 1992.
Nunberg, Jack H. et al., "Molecular Cloning and Characterization of the Glucoamylase Gene of *Aspergillus awamori*." *Molecular and Cellular Biology*, pp. 2306-2315, Nov. 1984.
Pearson, William R. et al., "Improved tools for biological sequence comparison." *Proc. Natl. Acad. Sci., U.S.A.*, vol. 85, pp. 2444-2448, Apr. 1988.
Penttila, Merja et al., "A versatile transformation system for the cellulolytic filamentous fungus *Trichoderma reesei*." *Gene*, vol. 61, pp. 155-164, 1987.
Pourquie, J. et al., "Scale Up of Cellulase Production and Utilization." *Biochemistry and Genetics of Cellulose Degradation*, Aubert, J. P. et al., ed., Academic Press, pp. 71-86, 1988.

Sheir-Neiss, G. et al., "Characterization of the secreted cellulases of *Trichoderma reesei* wild type and mutants during controlled fermentations." *Appl. Microbiol. Biotechnol.*, vol. 20, pp. 46-53, 1984.
Shibuya, Ichiro et al., "Molecular Cloning of the Glucoamylase Gene of *Aspergillus shirousami* and Its Expression in *Aspergillus oryzae*." *Agric. Biol. Chem.*, vol. 54, No. 8, pp. 1905-1914, 1990.
Swinkels, J. J. M., *Starch Conversion Technology*, Vvan Beynum et al. ed., Marcel Dekker, Inc., New York, pp. 32-38, 1985.
Takahashi, Tomoko et al., "Different Behavior towards Raw Starch of Three Forms of Glucoamylase from a *Rhizopus* Sp. " *J. Biochem.*, vol. 98, pp. 663-671, 1985.
Taylor, Pamela M. et al., "Some Properties of a Glucoamylase Produced by the Thermophilic Fungus *Humicola lanuginosa*." *Carbohydrate Research*, vol. 61, pp. 301-308, 1978.
Tomaz, Candida T. et al., "Studies on the chromatographic fractionation of *Trichoderma reesei* cellulases by hydrophobic interaction." *Journal of Chromatography A*, vol. 865, pp. 123-128, 1999.
Tosi, Luis Ricardo Orsini et al., "Purification and characterization of an extracellular glycoamylase from the thermophilic fungus *Humicola grisea* var. *thermoidea*." *Can J. Microbiol.*, vol. 39, pp. 846-855, 1993.
Van Tilbuergh, Herman et al., "Separation of endo- and exo-type cellulases using a new affinity chromatography method." FEBS, vol. 169, No. 2, pp. 215-218, Apr. 1984.
Ward, Michael et al., "Use of *Aspergillus* overproducing mutants, cured for integrated plasmid, to overproduce heterologous proteins." *Appl. Microbiol. Biotechnol.*, vol. 39, pp. 738-743, 1993.
Wiebe, Marilyn G. et al., "Growth-Rate-Independent Production of Recombinant Glucoamylase by *Fusarium venenatum* JeRS 325. " *Biotechnology and Bioengineering*, vol. 68, No. 3, pp. 245-251, May 5, 2000.
Withers, Julie M. et al., "Optimization and Stability of Glucoamylase Production by Recombinant Strains of *Aspergillus niger* in Chemostat Culture." *Biotechnology and Bioengineering*, vol. 59, No. 4, pp. 407-418, Aug. 20, 1998.
Office Action dated Mar. 5, 2008, in European Patent Application No. 04811428, filed Nov. 18, 2004.
Response dated Sep. 8, 2008, in European Patent Application No. 04811428, filed Nov. 18, 2004.
Office Action dated Oct. 21, 2008, in European Patent Application No. 04811428, filed Nov. 18, 2004.
Response dated Apr. 15, 2009, in European Patent Application No. 04811428, filed Nov. 18, 2004.
Office Action dated Jun. 12, 2009, in European Patent Application No. 04811428, filed Nov. 18, 2004.
Response dated Apr. 6, 2010, in European Patent Application No. 04811428, filed Nov. 18, 2004.
Office Action dated Oct. 22, 2010, in European Patent Application No. 04811428, filed Nov. 18, 2004.
Response dated Feb. 17, 2011, in European Patent Application No. 04811428, filed Nov. 18, 2004.

*H. grisea* GSHE nucleotide sequence with *putative* introns bold & underlined.

```
ATGCATACCTTCTCCAAGCTCCTCGTCCTGGGCTCTGCCGTCCAGTCTGCCCTCGGGCGGCCTCACGGCT
CTTCGCGTCTCCAGGAACGCGCTGCCGTTGATACCTTCATCAACACCGAGAAGCCCATCGCATGGAACAA
GCTGCTCGCCAACATCGGCCCTAACGGCAAAGCCGCTCCCGGTGCCGCCGCCGGCGTTGTGATTGCCAGC
CCTTCCAGGACGGACCCTCCTTGTACGTGGTGGCATGGAATGGACCCAAGAGACTGGTTTTAGATGAAAG
AGAGTTTCTGCTAACCGCCACACCCAGACTTCTTCACCTGGACCCGCGATGCCGCCCTGGTCCTCACCGG
CATCATCGAGTCCCTTGGCCACAACTACAACACCACCCTGCAGACCGTCATCCAGAACTACGTCGCGTCG
CAGGCCAAGCTGCAGCAGGTCTCGAACCCCTCGGGAACCTTCGCCGACGGCTCGGGTCTCGGTGAGGCCA
AGTTCAATGTCGACCTCACTGCCTTCACTGGCGAATGGGGTCGCCCTCAGAGGGACGGCCCGCCCCTGCG
CGCCATCGCTCTCATCCAGTACGCCAAGTGGCTGATCGCCAACGGCTACAAGAGCACGGCCAAGAGCGTC
GTCTGGCCCGTCGTCAAGAACGATCTCGCCTACACGGCCCAGTACTGGAACGAGACCGGCTTCGATCTCT
GGGAGGAGGTCCCCGGCAGCTCGTTCTTTACCATCGCCAGCTCTCACAGGGGTGAGTCATTTATTGTTCA
GTGTTTTCTCATTGAATAATTACCGGAATGCCACTGACGCCAAACAGCTCTGACTGAGGGTGCTTACCTC
GCCGCTCAGCTCGACACCGAGTGCCGCGCCTGCACGACCGTCGCCCCTCAGGTTCTGTGCTTCCAGCAGG
CCTTCTGGAACTCCAAGGGCAACTATGTCGTCTCCAACAGTAAGATCCCTACACCAACAAAAAAAATCGA
AAAGGAACGTTAGCTGACCCTTCTAGTCAACGGCGGCGAGTATCGCTCCGGCAAGGACGCCAACTCGATC
CTGGCGTCCATCCACAACTTCGACCCTGAGGCCGGCTGCGACAACCTGACCTTCCAGCCCTGCAGCGAGC
GCGCCCTGGCCAACCACAAGGCCTATGTCGACTCGTTCCGCAACCTCTACGCCATCAACAAGGGCATCGC
CCAGGGCAAGGCCGTTGCCGTCGGCCGCTACTCGGAGGATGTCTACTACAACGGCAACCCGTGGTACCTG
GCCAACTTTGCCGCCGCCGAGCAGCTCTACGACGCCATCTACGTGTGGAACAAGCAGGGCTCCATCACCG
TGACCTCGGTCTCCCTGCCCTTCTTCCGCGACCTTGTCTCGTCGGTCAGCACCGGCACCTACTCCAAGAG
CAGCTCGACCTTCACCAACATCGTCAACGCCGTCAAGGCCTACGCCGACGGCTTCATCGAGGTGGCGGCC
AAGTACACCCCGTCCAACGGCGCGCTCGCCGAGCAGTACGACCGCAACACGGGCAAGCCCGACTCGGCCG
CCGACCTGACGTGGTCGTACTCGGCCTTCCTCTCGGCCATCGACCGCCGCGCGGGTCTCGTCCCCCCGAG
CTGGCGGGCCAGCGTGGCCAAGAGCCAGCTGCCGTCCACCTGCTCGCGCATCGAGGTCGCCGGCACCTAC
GTCGCCGCCACGAGCACCTCGTTCCCGTCCAAGCAGACCCCGAACCCCTCCGCGGCGCCCTCCCCGTCCC
CCTACCCGACCGCCTGCGCGGACGCTAGCGAGGTGTACGTCACCTTCAACGAGCGCGTGTCGACCGCGTG
GGGCGAGACCATCAAGGTGGTGGGCAACGTGCCGGCGCTGGGGAACTGGGACACGTCCAAGGCGGTGACC
CTGTCGGCCAGCGGGTACAAGTCGAATGATCCCCTCTGGAGCATCACGGTGCCCATCAAGGCGACGGGCT
CGGCCGTGCAGTACAAGTATATCAAGGTCGGCACCAACGGGAAGATTACTTGGGAGTCGGACCCCAACAG
GAGCATTACCCTGCAGACGGCGTCGTCTGCGGGCAAGTGCGCCGCGCAGACGGTGAATGATTCGTGGCGT
TAA
```

FIG. 1

*H. grisea* GSHE protein sequence with *putative* signal sequence underlined.

*H. grisea* Mature GSHE protein sequence

```
AAGCTTACTAGTACTTCTCGAGCTCTGTACATGTCCGGTCGCGACGTACGCGTATCGATGGCGCCAGC
TGCAGGCGGCCGCCTGCAGCCACTTGCAGTCCCGTGGAATTCTCACGGTGAATGTAGGCCTTTTGTAG
GGTAGGAATTGTCACTCAAGCACCCCCAACCTCCATTACGCCTCCCCCATAGAGTTCCCAATCAGTGA
GTCATGGCACTGTTCTCAAATAGATTGGGGAGAAGTTGACTTCCGCCCAGAGCTGAAGGTCGCACAAC
CGCATGATATAGGGTCGGCAACGGCAAAAAAGCACGTGGCTCACCGAAAAGCAAGATGTTTGCGATCT
AACATCCAGGAACCTGGATACATCCATCATCACGCACGACCACTTTGATCTGCTGGTAAACTCGTATT
CGCCCTAAACCGAAGTGCGTGGTAAATCTACACGTGGGCCCCTTTCGGTATACTGCGTGTGTCTTCTC
TAGGTGCCATTCTTTTCCCTTCCTCTAGTGTTGAATTGTTTGTGTTGGAGTCCGAGCTGTAACTACCT
CTGAATCTCTGGAGAATGGTGGACTAACGACTACCGTGCACCTGCATCATGTATATAATAGTGATCCT
GAGAAGGGGGGTTTGGAGCAATGTGGGACTTTGATGGTCATCAAACAAAGAACGAAGACGCCTCTTTT
GCAAAGTTTTGTTTCGGCTACGGTGAAGAACTGGATACTTGTTGTGTCTTCTGTGTATTTTTGTGGCA
ACAAGAGGCCAGAGACAATCTATTCAAACACCAAGCTTGCTCTTTTGAGCTACAAGAACCTGTGGGGT
ATATATCTAGAGTTGTGAAGTCGGTAATCCCGCTGTATAGTAATACGAGTCGCATCTAAATACTCCGA
AGCTGCTGCGAACCCGGAGAATCGAGATGTGCTGGAAAGCTTCTAGCGAGCGGCTAAATTAGCATGAA
AGGCTATGAGAAATTCTGGAGACGGCTTGTTGAATCATGGCGTTCCATTCTTCGACAAGCAAAGCGTT
CCGTCGCAGTAGCAGGCACTCATTCCCGAAAAAACTCGGAGATTCCTAAGTAGCGATGGAACCGGAAT
AATATAATAGGCAATACATTGAGTTGCCTCGACGGTTGCAATGCAGGGGTACTGAGCTTGGACATAAC
TGTTCCGTACCCCACCTCTTCTCAACCTTTGGCGTTTCCCTGATTCAGCGTACCCGTACAAGTCGTAA
TCACTATTAACCCAGACTGACCGGACGTGTTTTGCCCTTCATTTGGAGAAATAATGTCATTGCGATGT
GTAATTTGCCTGCTTGACCGACTGGGGCTGTTCGAAGCCCGAATGTAGGATTGTTATCCGAACTCTGC
TCGTAGAGGCATGTTGTGAATCTGTGTCGGCAGGACACGCCTCGAAGGTTCACGGCAAGGGAAACCA
CCGATAGCAGTGTCTAGTAGCAACCTGTAAAGCCGCAATGCAGCATCACTGGAAAATACAAACCAATG
GCTAAAAGTACATAAGTTAATGCCTAAAGAAGTCATATACCAGCGGCTAATAATTGTACAATCAAGTG
GCTAAACGTACCGTAATTTGCCAACGGCTTGTGGGGTTGCAGAAGCAACGGCAAAGCCCCACTTCCCC
ACGTTTGTTTCTTCACTCAGTCCAATCTCAGCTGGTGATCCCCAATTGGGTCGCTTGTTTGTTCCGG
TGAAGTGAAAGAAGACAGAGGTAAGAATGTCTGACTCGGAGCGTTTTGCATACAACCAAGGGCAGTGA
TGGAAGACAGTGAAATGTTGACATTCAAGGAGTATTTAGCCAGGGATGCTTGAGTGTATCGTGTAAGG
AGGTTTGTCTGCCGATACGACGAATACTGTATAGTCACTTCTGATGAAGTGGTCCATATTGAAATGTA
AAGTCGGCACTGAACAGGCAAAAGATTGAGTTGAAACTGCCTAAGATCTCGGGCCCTCGGGCCTTCGG
CCTTTGGGTGTACATGTTTGTGCTCCGGGCAAATGCAAAGTGTGGTAGGATCGAACACACTGCTGCCT
TTACCAAGCAGCTGAGGGTATGTGATAGGCAAATGTTCAGGGGCACTGCATGGTTTCGAATAGAAAG
AGAAGCTTAGCCAAGAACAATAGCCGATAAAGATAGCCTCATTAAACGGAATGAGCTAGTAG
```

FIG. 4A

```
GCAAAGTCAGCGAATGTGTATATATAAAGGTTCGAGGTCCGTGCCTCCCTCATGCTCTCCCCATCTAC
TCATCAACTCAGATCCTCCAGGAGACTTGTACACCATCTTTTGAGGCACAGAAACCCAATAGTCAACC
ATCACAAGTTTGTACAAAAAAGCAGGCTCCGCGGCCGCCCCCTTCAACATGCATACCTTCTCCAAGCT
CCTCGTCCTGGGCTCTGCCGTCCAGTCTGCCCTCGGGCGGCCTCACGGCTCTTCGCGTCTCCAGGAAC
GCGCTGCCGTTGATACCTTCATCAACACCGAGAAGCCCATCGCATGGAACAAGCTGCTCGCCAACATC
GGCCCTAACGGCAAAGCCGCTCCCGGTGCCGCCGCCGGCGTTGTGATTGCCAGCCCTTCCAGGACGGA
CCCTCCTTGTACGTGGTGGCATGGAATGGACCCAAGAGACTGGTTTTAGATGAAAGAGAGTTTCTGCT
AACCGCCACACCCAGACTTCTTCACCTGGACCCGCGATGCCGCCCTGGTCCTCACCGGCATCATCGAG
TCCCTTGGCCACAACTACAACACCACCCTGCAGACCGTCATCCAGAACTACGTCGCGTCGCAGGCCAA
GCTGCAGCAGGTCTCGAACCCCTCGGGAACCTTCGCCGACGGCTCGGGTCTCGGTGAGGCCAAGTTCA
ATGTCGACCTCACTGCCTTCACTGGCGAATGGGGTCGCCCTCAGAGGGACGGCCCGCCCCTGCGCGCC
ATCGCTCTCATCCAGTACGCCAAGTGGCTGATCGCCAACGGCTACAAGAGCACGGCCAAGAGCGTCGT
CTGGCCCGTCGTCAAGAACGATCTCGCCTACACGGCCCAGTACTGGAACGAGACCGGCTTCGATCTCT
GGGAGGAGGTCCCCGGCAGCTCGTTCTTTACCATCGCCAGCTCTCACAGGGGTGAGTCATTTATTGTT
CAGTGTTTTCTCATTGAATAATTACCGGAATGCCACTGACGCCAAACAGCTCTGACTGAGGGTGCTTA
CCTCGCCGCTCAGCTCGACACCGAGTGCCGCGCCTGCACGACCGTCGCCCCTCAGGTTCTGTGCTTCC
AGCAGGCCTTCTGGAACTCCAAGGGCAACTATGTCGTCTCCAACAGTAAGATCCCTACACCAACAAAA
AAAATCGAAAAGGAACGTTAGCTGACCCTTCTAGTCAACGGCGGCGAGTATCGCTCCGGCAAGGACGC
CAACTCGATCCTGGCGTCCATCACAACTTCGACCCTGAGGCCGGCTGCGACAACCTGACCTTCCAGC
CCTGCAGCGAGCGCGCCCTGGCCAACCACAAGGCCTATGTCGACTCGTTCCGCAACCTCTACGCCATC
AACAAGGGCATCGCCCAGGGCAAGGCCGTTGCCGTCGGCCGCTACTCGGAGGATGTCTACTACAACGG
CAACCCGTGGTACCTGGCCAACTTTGCCGCCGCCGAGCAGCTCTACGACGCCATCTACGTGTGGAACA
AGCAGGGCTCCATCACCGTGACCTCGGTCTCCCTGCCCTTCTTCCGCGACCTTGTCTCGTCGGTCAGC
ACCGGCACCTACTCCAAGAGCAGCTCGACCTTCACCAACATCGTCAACGCCGTCAAGGCCTACGCCGA
CGGCTTCATCGAGGTGGCGGCCAAGTACACCCCGTCCAACGGCGCGCTCGCCGAGCAGTACGACCGCA
ACACGGGCAAGCCCGACTCGGCCGCCGACCTGACGTGGTCGTACTCGGCCTTCCTCTCGGCCATCGAC
CGCCGCGCGGGTCTCGTCCCCCCGAGCTGGCGGGCCAGCGTGGCCAAGAGCCAGCTGCCGTCCACCTG
CTCGCGCATCGAGGTCGCCGGCACCTACGTCGCCGCCACGAGCACCTCGTTCCCGTCCAAGCAGACCC
CGAACCCCTCCGCGGCGCCCTCCCCGTCCCCTACCCGACCGCCTGCGCGGACGCTAGCGAGGTGTAC
GTCACCTTCAACGAGCGCGTGTCGACCGCGTGGGGCGAGACCATCAAGGTGGTGGGCAACGTGCCGGC
GCTGGGGAACTGGGACACGTCCAAGGCGGTGACCCTGTCGGCCAGCGGGTACAAGTCGAATGATCCCC
TCTGGAGCATCACGGTGCCCATCAAGGCGACGGGCTCGGCCGTGCAGTACAAGTATATCAAG
```

FIG. 4B

```
GTCGGCACCAACGGGAAGATTACTTGGGAGTCGGACCCCAACAGGAGCATTACCCTGCAGACGGCGTCGT
CTGCGGGCAAGTGCGCCGCGCAGACGGTGAATGATTCGTGGCGTTAAAAGGGTGGGCGCGCCGACCCA
GCTTTCTTGTACAAAGTGGTGATCGCGCCAGCTCCGTGCGAAAGCCTGACGCACCGGTAGATTCTTGG
TGAGCCCGTATCATGACGGCGGCGGGAGCTACATGGCCCCGGGTGATTTATTTTTTTGTATCTACTT
CTGACCCTTTTCAAATATACGGTCAACTCATCTTTCACTGGAGATGCGGCCTGCTTGGTATTGCGATG
TTGTCAGCTTGGCAAATTGTGGCTTTCGAAAACACAAAACGATTCCTTAGTAGCCATGCATTTTAAGA
TAACGGAATAGAAGAAAGAGGAAATTAAAAAAAAAAAAAAAAACAAACATCCCGTTCATAACCCGTAGA
ATCGCCGCTCTTCGTGTATCCCAGTACCAGTTTATTTTGAATAGCTCGCCCGCTGGAGAGCATCCTGA
ATGCAAGTAACAACCGTAGAGGCTGACACGGCAGGTGTTGCTAGGGAGCGTCGTGTTCTACAAGGCCA
GACGTCTTCGCGGTTGATATATATGTATGTTTGACTGCAGGCTGCTCAGCGACGACAGTCAAGTTCGC
CCTCGCTGCTTGTGCAATAATCGCAGTGGGGAAGCCACACCGTGACTCCCATCTTTCAGTAAAGCTCT
GTTGGTGTTTATCAGCAATACACGTAATTTAAACTCGTTAGCATGGGGCTGATAGCTTAATTACCGTT
TACCAGTGCCATGGTTCTGCAGCTTTCCTTGGCCCGTAAAATTCGGCGAAGCCAGCCAATCACCAGCT
AGGCACCAGCTAAACCCTATAATTAGTCTCTTATCAACACCATCCGCTCCCCGGGATCAATGAGGAG
AATGAGGGGATGCGGGCTAAAGAAGCCTACATAACCCTCATGCCAACTCCCAGTTTACACTCGTCG
AGCCAACATCCTGACTATAAGCTAACACAGAATGCCTCAATCCTGGGAAGAACTGGCCGCTGATAAGC
GCGCCCGCCTCGCAAAAACCATCCCTGATGAATGGAAAGTCCAGACGCTGCCTGCGGAAGACAGCGTT
ATTGATTTCCCAAAGAAATCGGGGATCCTTTCAGAGGCCGAACTGAAGATCACAGAGGCCTCCGCTGC
AGATCTTGTGTCCAAGCTGGCGGCCGGAGAGTTGACCTCGGTGGAAGTTACGCTAGCATTCTGTAAAC
GGGCAGCAATCGCCCAGCAGTTAGTAGGGTCCCCTCTACCTCTCAGGGAGATGTAACAACGCCACCTT
ATGGGACTATCAAGCTGACGCTGGCTTCTGTGCAGACAAACTGCGCCCACGAGTTCTTCCCTGACGCC
GCTCTCGCGCAGGCAAGGGAACTCGATGAATACTACGCAAAGCACAAGAGACCCGTTGGTCCACTCCA
TGGCCTCCCCATCTCTCTCAAAGACCAGCTTCGAGTCAAGGTACACCGTTGCCCCTAAGTCGTTAGAT
GTCCCTTTTTGTCAGCTAACATATGCCACCAGGGCTACGAAACATCAATGGGCTACATCTCATGGCTA
AACAAGTACGACGAAGGGGACTCGGTTCTGACAACCATGCTCCGCAAAGCCGGTGCCGTCTTCTACGT
CAAGACCTCTGTCCCGCAGACCCTGATGGTCTGCGAGACAGTCAACAACATCATCGGGCGCACCGTCA
ACCCACGCAACAAGAACTGGTCGTGCGGCGGCAGTTCTGGTGGTGAGGGTGCGATCGTTGGGATTCGc
RVTGGTGGCGTCATCGGTGTAGGAACGGATATCGGTGGCTCGATTCGAGTGCCGGCCGCGTTCAACTT
CCTGTACGGTCTAAGGCCGAGTCATGGGCGGCTGCCGTATGCAAAGATGGCGAACAGCATGGAGGGTC
AGGAGACGGTGCACAGCGTTGTCGGGCCGATTACGCACTCTGTTGAGGGTGAGTCCTTCGCCTCTTCC
TTCTTTTCCTGCTCTATACCAGGCCTCCACTGTCCTCCTTTCTTGCTTTTTATACTATATACGAGACC
GGCAGTCACTGATGAAGTATGTTAGACCTCCGCCTCTTCACCAAATCCGTCCTCGGTCAG
```

*FIG. 4C*

```
GAGCCATGGAAATACGACTCCAAGGTCATCCCCATGCCCTGGCGCCAGTCCGAGTCGGACATTATTGCCT
CCAAGATCAAGAACGGCGGGCTCAATATCGGCTACTACAACTTCGACGGCAATGTCCTTCCACACCCT
CCTATCCTGCGCGGCGTGGAAACCACCGTCGCCGCACTCGCCAAAGCCGGTCACACCGTGACCCCGTG
GACGCCATACAAGCACGATTTCGGCCACGATCTCATCTCCCATATCTACGCGGCTGACGGCAGCcRVG
CCGACGTAATGCGCGATATCAGTGCATCCGGCGAGCCGGCGATTCCAAATATCAAAGACCTACTGAAC
CCGAACATCAAAGCTGTTAACATGAACGAGCTCTGGGACACGCATCTCCAGAAGTGGAATTACCAGAT
GGAGTACCTTGAGAAATGGCGGGAGGCTGAAGAAAAGGCCGGGAAGGAACTGGACGCCATCATCGCGC
CGATTACGCCTACCGCTGCGGTACGGCATGACCAGTTCCGGTACTATGGGTATGCCTCTGTGATCAAC
CTGCTGGATTTCACGAGCGTGGTTGTTCCGGTTACCTTTGCGGATAAGAACATCGATAAGAAGAATGA
GAGTTTCAAGGCGGTTAGTGAGCTTGATGCCCTCGTGCAGGAAGAGTATGATCCGGAGGCGTACCATG
GGGCACCGGTTGCAGTGCAGGTTATCGGACGGAGACTCAGTGAAGAGAGGACGTTGGCGATTGCAGAG
GAAGTGGGGAAGTTGCTGGGAAATGTGGTGACTCCATAGCTAATAAGTGTCAGATAGCAATTTGCACA
AGAAATCAATACCAGCAACTGTAAATAAGCGCTGAAGTGACCATGCCATGCTACGAAAGAGCAGAAAA
AAACCTGCCGTAGAACCGAAGAGATATGACACGCTTCCATCTCTCAAAGGAAGAATCCCTTCAGGGTT
GCGTTTCCAGTCTAGACACGTATAACGGCACAAGTGTCTCTCACCAAATGGGTTATATCTCAAATGTG
ATCTAAGGATGGAAAGCCCAGAATATCGATCGCGCGCAGATCCATATATAGGGCCCGGGTTATAATTA
CCTCAGGTCGACGTCCCATGGCCATTCGAATTCGTAATCATGGTCATAGCTGTTTCCTGTGTGAAATT
GTTATCCGCTCACAATTCCACACAACATACGAGCCGGAAGCATAAAGTGTAAAGCCTGGGGTGCCTAA
TGAGTGAGCTAACTCACATTAATTGCGTTGCGCTCACTGCCCGCTTTCCAGTCGGGAAACCTGTCGTG
CCAGCTGCATTAATGAATCGGCCAACGCGCGGGGAGAGGCGGTTTGCGTATTGGGCGCTCTTCCGCTT
CCTCGCTCACTGACTCGCTGCGCTCGGTCGTTCGGCTGCGGCGAGCGGTATCAGCTCACTCAAAGGCG
GTAATACGGTTATCCACAGAATCAGGGGATAACGCAGGAAAGAACATGTGAGCAAAAGGCCAGCAAAA
GGCCAGGAACCGTAAAAAGGCCGCGTTGCTGGCGTTTTTCCATAGGCTCCGCCCCCCTGACGAGCATC
ACAAAAATCGACGCTCAAGTCAGAGGTGGCGAAACCCGACAGGACTATAAAGATACCAGGCGTTTCCC
CCTGGAAGCTCCCTCGTGCGCTCTCCTGTTCCGACCCTGCCGCTTACCGGATACCTGTCCGCCTTTCT
CCCTTCGGGAAGCGTGGCGCTTTCTCATAGCTCACGCTGTAGGTATCTCAGTTCGGTGTAGGTCGTTC
GCTCCAAGCTGGGCTGTGTGCACGAACCCCCCGTTCAGCCCGACCGCTGCGCCTTATCCGGTAACTAT
CGTCTTGAGTCCAACCCGGTAAGACACGACTTATCGCCACTGGCAGCAGCCACTGGTAACAGGATTAG
CAGAGCGAGGTATGTAGGCGGTGCTACAGAGTTCTTGAAGTGGTGGCCTAACTACGGCTACACTAGAA
GAACAGTATTTGGTATCTGCGCTCTGCTGAAGCCAGTTACCTTCGGAAAAAGAGTTGGTAGCTCTTGA
TCCGGCAAACAAACCACCGCTGGTAGCGGTGGTTTTTTGTTTGCAAGCAGCAGATTACGCGCAGAAA
AAAAGGATCTCAAGAAGATCCTTTGATCTTTTCTACGGGGTCTGACGCTCAGTGGAACGA
```

FIG. 4D

AAACTCACGTTAAGGGATTTTGGTCATGAGATTATCAAAAAGGATCTTCACCTAGATCCTTTTAAATT
AAAAATGAAGTTTTAAATCAATCTAAAGTATATATGAGTAAACTTGGTCTGACAGTTACCAATGCTTA
ATCAGTGAGGCACCTATCTCAGCGATCTGTCTATTTCGTTCATCCATAGTTGCCTGACTCCCCGTCGT
GTAGATAACTACGATACGGGAGGGCTTACCATCTGGCCCCAGTGCTGCAATGATACCGCGAGACCCAC
GCTCACCGGCTCCAGATTTATCAGCAATAAACCAGCCAGCCGGAAGGGCCGAGCGCAGAAGTGGTCCT
GCAACTTTATCCGCCTCCATCCAGTCTATTAATTGTTGCCGGGAAGCTAGAGTAAGTAGTTCGCCAGT
TAATAGTTTGCGCAACGTTGTTGCCATTGCTACAGGCATCGTGGTGTCACGCTCGTCGTTTGGTATGG
CTTCATTCAGCTCCGGTTCCCAACGATCAAGGCGAGTTACATGATCCCCATGTTGTGCAAAAAGCG
GTTAGCTCCTTCGGTCCTCCGATCGTTGTCAGAAGTAAGTTGGCCGCAGTGTTATCACTCATGGTTAT
GGCAGCACTGCATAATTCTCTTACTGTCATGCCATCCGTAAGATGCTTTTCTGTGACTGGTGAGTACT
CAACCAAGTCATTCTGAGAATAGTGTATGCGGCGACCGAGTTGCTCTTGCCCGGCGTCAATACGGGAT
AATACCGCGCCACATAGCAGAACTTTAAAAGTGCTCATCATTGGAAAACGTTCTTCGGGGCGAAAACT
CTCAAGGATCTTACCGCTGTTGAGATCCAGTTCGATGTAACCCACTCGTGCACCCAACTGATCTTCAG
CATCTTTTACTTTCACCAGCGTTTCTGGGTGAGCAAAAACAGGAAGGCAAAATGCCGCAAAAAAGGGA
ATAAGGGCGACACGGAAATGTTGAATACTCATACTCTTCCTTTTTCAATATTATTGAAGCATTTATCA
GGGTTATTGTCTCATGAGCGGATACATATTTGAATGTATTTAGAAAAATAAACAAATAGGGGTTCCGC
GCACATTTCCCCGAAAAGTGCCACCTGACGTCTAAGAAACCATTATTATCATGACATTAACCTATAAA
AATAGGCGTATCACGAGGCCCTTTCGTCTCGCGCGTTTCGGTGATGACGGTGAAAACCTCTGACACAT
GCAGCTCCCGGAGACGGTCACAGCTTGTCTGTAAGCGGATGCCGGGAGCAGACAAGCCCGTCAGGGCG
CGTCAGCGGGTGTTGGCGGGTGTCGGGCTGGCTTAACTATGCGGCATCAGAGCAGATTGTACTGAGA
GTGCACCATAAAATTGTAAACGTTAATATTTTGTTAAAATTCGCGTTAAATTTTGTTAAATCAGCTC
ATTTTTTAACCAATAGGCCGAAATCGGCAAAATCCCTTATAAATCAAAAGAATAGCCCGAGATAGGGT
TGAGTGTTGTTCCAGTTTGGAACAAGAGTCCACTATTAAAGAACGTGGACTCCAACGTCAAAGGGCGA
AAAACCGTCTATCAGGGCGATGGCCCACTACGTGAACCATCACCCAAATCAAGTTTTTTGGGGTCGAG
GTGCCGTAAAGCACTAAATCGGAACCCTAAAGGGAGCCCCCGATTTAGAGCTTGACGGGGAAAGCCGG
CGAACGTGGCGAGAAAGGAAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACAGGGCGCGTACTATGGTTG
CTTTGACGTATGCGGTGTGAAATACCGCACAGATGCGTAAGGAGAAAATACCGCATCAGGCGCCATTC
GCCATTCAGGCTGCGCAACTGTTGGGAAGGGCGATCGGTGCGGGCCTCTTCGCTATTACGCCAGCTGG
CGAAAGGGGGATGTGCTGCAAGGCGATTAAGTTGGGTAACGCCAGGGTTTTCCCAGTCACGACGTTGT
AAAACGACGGCCAGTGCCC

FIG. 4E

Genomic Nucleotide Sequence of *Aspergillus kawachi* GSHE

```
ATGTCGTTCCGATCTCTTCTCGCCCTGAGCGGCCTTGTCTGCTCGGGGTTGGCAAGTGTGAT
TTCCAAGCGCGCGACCTTGGATTCGTGGTTGAGCAACGAAGCGACCGTGGCCCGTACTGCGA
TCCTGAATAACATCGGGGCGGACGGTGCTTGGGTGTCGGGCGCGGACTCTGGCATTGTCGTT
GCCAGTCCCAGCACCGATAACCCGGACTGTATGTTTTGAGTTCGGATTATGAATGTGTCTTG
GTTGATTGATGCTGACTGGCGTGTCTTTTGATGATTGTAGACTTCTACACCTGGACTCGCGA
CTCTGGTCTCGTCATCAAGACCCTCGTCGACCTCTTCCGCAATGGAGATACTGATCTCCTTT
CCACCATTGAGCACTACATCTCCTCTCAGGCAATTATTCAGGGTGTCAGTAACCCCTCTGGT
GATCTGTCCAGCGGTGGTCTTGGTGAGCCCAAGTTCAATGTCGATGAGACTGCCTACACCGG
TTCTTGGGGACGGCCGCAGCGTGATGGTCCTGCCCTGAGAGCAACTGCTATGATCGGCTTTG
GGCAGTGGCTGCTTGTATGTTCTCCACCTCCTTGCGTCTGATCTGCAACATATGTAGCCGAC
TGGTCAGGACAATGGCTACACCAGCGCTGCAACAGAGATTGTTTGGCCCCTCGTTAGGAACG
ACCTGTCGTATGTGGCTCAGTACTGGAACCAGACGGGATATGGTGTGTTTGATTGATCGGGG
TTCAAGGGTGTTTGTGCATCGGAGCTAACTTCGCGGTCGCAGATCTCTGGGAAGAAGTTAAT
GGCTCGTCCTTCTTCACTATTGCCGTGCAACACCGCGCCCTCGTCGAAGGTAGTGCCTTCGC
GACGGCCGTCGGCTCGTCCTGCTCCTGGTGTGATTCGCAGGCACCTCAGATTCTCTGTTACT
TGCAGTCCTTCTGGACCGGCAGCTACATCCTGGCCAACTTTGACAGCAGCCGTTCCGGCAAG
GACACAAACACCCTCCTGGGAAGCATCCACACCTTTGATCCTGAGGCTGGATGCGACGACTC
CACCTTCCAGCCCTGCTCCCGCGTGCGCTCGCCAACCATAAGGAGGTTGTAGACTCTTTCC
GCTCGATCTATACTCTCAACGATGGTCTCAGTGACAGTGAGGCGGTTGCGGTCGGTCGGTAC
CCTGAGGATAGCTACTACAACGGCAACCCGTGGTTCCTGTGCACCTTGGCTGCCGCGGAACA
GCTGTACGATGCTCTGTACCAGTGGGACAAGCAGGGGTCGTTGGAGATCACAGACGTGTCAC
TTGACTTCTTCAAGGCTCTGTACAGTGGTGCTGCCACCGGCACGTACTCTTCGTCCAGCTCG
ACCTATAGCAGCATTGTGAGTGCCGTCAAGACTTTCGCTGATGGTTTTGTTTCTATTGTGGT
AAGTCTACGCTAGACGAGCGCTCATATTTACAGAGGGTGCGTACTAACAGGATTAGGAAACT
CACGCCGCAAGCAACGGCTCTCTGTCTGAGCAATTCGACAAGTCTGATGGCGACGAGCTTTC
TGCTCGCGATCTGACCTGGTCTTACGCTGCTCTGCTGACCGCCAACAACGTCGTAATTCTG
TCGTGCCCCCGTCTTGGGGTGAGACCTCTGCCAGCAGCGTGCCCGGCACCTGTGCGGCTACC
TCTGCCTCTGGTACCTACAGCAGTGTGACCGTCACCTCGTGGCCGAGCATCGTGGCTACTGG
TGGCACCACTACGACGGCTACTACCACTGGATCGGGCGGCGTGACCTCGACCAGCAAGACCA
CCACAACTGCTAGTAAGACCAGCACCACTACGTCCTCGACCTCCTGCACCACCCCCACTGCC
GTAGCTGTGACCTTTGATCTGACGGCGACCACCACCTACGGCGAGAACATCTACCTGGTCGG
GTCGATCTCTCAGCTCGGTGACTGGGAGACCAGCGATGGCATAGCTCTGAGCGCTGACAAGT
ACACTTCCAGCAACCCGCTTTGGTATGTAACTGTGACTCTGCCGGCTGGTGAGTCATTTGAG
TACAAGTTCATCCGCGTCGAGAGCGATGACTCCGTGGAGTGGGAGAGCGACCCGAACCGGGA
ATACACCGTTCCTCAGGCGTGCGGCGAGTCGACCGCGACGGTGACCGACACCTGGCGGTAG
```

FIG. 6

*Aspergillus awamori* var. *kawachi* GSHE precursor
(i.e.: with signal sequence underlined) protein sequence.

Mature (i.e. expressed protein with the putative signal sequence removed)
*Aspergillus awamori* var. *kawachi* GSHE protein sequence.

ATLDSWLSNEATVARTAILNNIGADGAWVSGADSGIVVASPSTDNPDYFYTWTRDSGLVIKT
LVDLFRNGDTDLLSTIEHYISSQAIIQGVSNPSGDLSSGGLGEPKFNVDETAYTGSWGRPQR
DGPALRATAMIGFGQWLLDNGYTSAATEIVWPLVRNDLSYVAQYWNQTGYDLWEEVNGSSFF
TIAVQHRALVEGSAFATAVGSSCSWCDSQAPQILCYLQSFWTGSYILANFDSSRSGKDTNTL
LGSIHTFDPEAGCDDSTFQPCSPRALANHKEVVDSFRSIYTLNDGLSDSEAVAVGRYPEDSY
YNGNPWFLCTLAAAEQLYDALYQWDKQGSLEITDVSLDFFKALYSGAATGTYSSSSSTYSSI
VSAVKTFADGFVSIVETHAASNGSLSEQFDKSDGDELSARDLTWSYAALLTANNRRNSVVPP
SWGETSASSVPGTCAATSASGTYSSVTVTSWPSIVATGGTTTTATTTGSGGVTSTSKTTTTA
SKTSTTTSSTSCTTPTAVAVTFDLTATTTYGENIYLVGSISQLGDWETSDGIALSADKYTSS
NPLWYVTVTLPAGESFEYKFIRVESDDSVEWESDPNREYTVPQACGESTATVTDTWR

*FIG. 7B*

Acc. Voltage 5 kV
Magnification 5K

Acc. Voltage 2 kV
Magnification 7K

Acc. Voltage 2 kV
Magnification 5K

Acc. Voltage 2 kV
Magnification 4K

EXPRESSION OF GRANULAR STARCH HYDROLYZING ENZYMES IN TRICHODERMA AND PROCESS FOR PRODUCING GLUCOSE FROM GRANULAR STARCH SUSTRATES

CROSS-REFERENCE TO RELATED APPLICATIONS

The present application is a continuation U.S. application Ser. No. 13/664,216, filed Oct. 30, 2012, which is a continuation of U.S. application Ser. No. 13/230,707, filed Sep. 12, 2011, now U.S. Pat. No. 8,323,932, which is a continuation of U.S. application Ser. No. 11/875,279, filed Oct. 19, 2007, now U.S. Pat. No. 8,034,590, which is a divisional application of U.S. patent application Ser. No. 10/991,654, filed Nov. 18, 2004, now U.S. Pat. No. 7,303,899, and claims priority to U.S. Provisional Patent Application Ser. No. 60/524,279 entitled Expression of Granular Starch Hydrolyzing Enzyme in *Trichoderma*, filed Nov. 21, 2003; U.S. Provisional Patent Application Ser. No. 60/531,953 entitled Enzyme Compositions for Glucose Feed from Granular Starch Substrates, filed Dec. 22, 2003; and U.S. Provisional Patent Application Ser. No. 60/566,358 entitled Expression of Granular Starch Hydrolyzing Enzyme in *Trichoderma*, filed Apr. 28, 2004.

SEQUENCE LISTING

The sequence listing submitted via EFS, in compliance with 37 C.F.R. §1.52(e), is incorporated herein by reference. The sequence listing text file submitted via EFS contains the file "30824-US-CNT4-SeqListing.txt" created on Feb. 24, 2012, and which is 39,952 bytes in size.

FIELD OF THE INVENTION

The present invention relates to filamentous fungal host cells useful for the expression of heterologous granular starch hydrolyzing enzymes having glucoamylase activity (GSHE). The invention further relates to the use of the GSHE in methods for producing glucose syrup and other end products from granular starch substrates comprising contacting a granular starch substrate, at or below the gelatinization temperature of the granular starch, simultaneously with a starch liquefying amylase and a GSHE. The invention further relates to enzyme compositions comprising the GSHE and starch liquefying amylase.

BACKGROUND OF THE INVENTION

Industrial fermentation predominately uses glucose as a feedstock for the production of a multitude of proteins, enzymes, amino acids, alcohols, organic acids, pharmaceuticals and other chemicals. In many applications, the glucose is produced from the enzymatic conversion of carbon substrates such as biomass and starch. Starch, which is abundantly found in green plants, accumulates as microscopic granules varying in diameter from 0.5 to 175 microns. The partial crystalline nature of these starch granules imparts insolubility in cold water. As a result, the solubilization of starch granules in water requires a tremendous amount of heat energy to disrupt the crystalline structure of the granule resulting in the solubilization of partially hydrolyzed starch. Numerous solubilization processes have been employed and these include direct and indirect heating systems, such as direct heating by steam injection. (See for example, STARCH CHEMISTRY AND TECHNOLOGY, eds R. L. Whistler et al., $2^{nd}$ Ed., 1984 Academic Press Inc., Orlando, Fla.; STARCH CONVERSION TECHNOLOGY, Eds. G. M. A. Van Beynum et al., Food Science and Technology Series, Marcel Dekker Inc., NY; and THE ALCOHOL TEXTBOOK, $3^{rd}$ Ed., Eds. K. Jacques, T. P. Lyons and D. R. Kelsall, 1999, Nottingham University Press, UK).

In general, two enzyme steps have been used for the hydrolysis of starch to glucose. The first step is a liquefaction step, and the second step is a saccharification step. In the liquefaction step, the insoluble starch granules are slurried in water, gelatinized with heat and hydrolyzed by a thermostable alpha amylase (EC.3.2.1.1, alpha (1-4)-glucan glucanohydrolase) in the presence of added calcium to produce a mash of dextrins. The resulting mash is generally cooled to about 60 to 65° C. In the saccharification step, the soluble dextrins (sugars) are further hydrolyzed to dextrose (glucose) by an enzyme having glucoamylase (EC 3.2.1.3, alpha (1,4)-glucan glucohydrolase) activity. Glucose may then be used as an end product or used as a precursor to be converted into other commercially important desired end products, such as fructose, sorbitol, ethanol, lactic acid, ascorbic acid (ASA) intermediates and 1,3 propanediol.

In the late 1950s, glucoamylases derived from *Aspergillus niger* were commercialized, and these enzymes significantly improved the conversion of starch to glucose. Another significant improvement occurred in the 1970s. A thermostable alpha amylase having improved thermostability, pH stability and lower calcium dependency was derived and commercialized from *Bacillus licheniformis* (U.S. Pat. No. 3,912,590).

Further industrial processes have been adopted by the starch sweetener industry for the enzyme liquefaction process (U.S. Pat. No. 5,322,778). Some of these processes include, a low temperature process (105-110° C. for 5-8 min) with lower steam requirements and a high temperature process (148° C.+/−5° C. for 8-10 sec), which improves gelatinization of the starch granules resulting in improved filtration characteristics and quality of the liquefied starch substrate (Shetty, et al., (1988) *Cereal Foods World* 33:929-934).

While enzyme starch liquefaction processes are well established, improvements with respect to yield loss, processing costs, energy consumption, pH adjustments, temperature thresholds, calcium requirement and the levels of retrograded starch would be desirable. In particular, it is well known that residual alpha amylase from the liquefaction step, under saccharification conditions, has an adverse effect on process efficiency and that the residual alpha amylase must be inactivated prior to saccharification by glucoamylases. Inactivation is generally accomplished by lowering the pH of the liquefied starch to pH 4.2 to 4.5 at 95° C. Another disadvantage of liquefaction processes is the alkaline isomerization of reducing groups. Alkaline isomerization results in the formation of a disaccharide, maltulose (4-alpha-D-glucopyranosyl-D-fructose). Maltulose lowers the glucose yield because it is resistant to hydrolysis by glucoamylases and alpha amylases. Further, it is difficult to control the formation of reversion reaction products catalyzed by active glucoamylases at high glucose concentration. Glucoamylases from *Aspergillus niger* are generally thermostable under the typical saccharification conditions. Therefore, a substantial amount of the glucoamylase activity may remain after the saccharification reaction. Solutions to some of the problems as discussed herein have been suggested by various researchers.

For example, Leach et al (U.S. Pat. No. 4,113,509 and U.S. Pat. No. 3,922,196) disclose a process for converting granular starch (refined) into soluble hydrolyzate by incubating the granular starch with bacterial alpha amylase at a temperature below the starch gelatinization temperature. Beta amylase was then used for hydrolysis to produce high maltose syrup.

European Patent Application No. 0350737 A2 discloses a process for producing maltose syrup by hydrolyzing a granular (purified) starch from corn, wheat, potato and sweet potato at 60° C. without the conventional liquefaction step (gelatinization followed by liquefaction at high temperature) using an alpha amylase from *Bacillus stearothermophilus*.

A multi-step process to convert granular (raw) starch to glucose using a glucoamylase demonstrating raw starch hydrolyzing capability has been previously described (U.S. Pat. No. 4,618,579). However, only 60% of the starch was hydrolyzed, which then resulted in an extensive recycling process.

Not only would it be advantageous to improved upon conventional processes for granular starch conversion, but also it would be desirable to provide processes resulting in increased expression and production of the enzymes used therefore. For example, glucoamylases having granular starch hydrolyzing activity with improved characteristics such as increased specific activity, different pH ranges and/or different levels of glycosylation may be particularly advantageous for use in industrial starch conversion. The present invention not only meets some of these needs but also results in an increase in the efficiency of producing various end products obtained from starch hydrolysis.

BRIEF SUMMARY OF THE INVENTION

One embodiment of the present invention concerns a one-step process for converting granular starch to glucose by hydrolyzing granular starch at or below the gelatinization temperature of the granular starch substrate, by simultaneously contacting the ungelatinized starch substrate with an endo-acting alpha amylase and a saccharifying enzyme having glucoamylase activity, and more specifically having granular starch hydrolyzing activity.

The present invention finds utility and improvement over prior art processes in at least one of the following ways a) both the alpha amylase and the glucoamylase having granular starch hydrolyzing activity are active during saccharification; b) the starch substrate is used in granular form and the starch is hydrolyzed; c) a single pH is used for solubilization and saccharification of the granular starch; d) the saccharification time period is shorter using granular starch compared to the current saccharification time using liquefied starch substrate; e) a high glucose syrup with reduced higher sugar content is obtained compared to glucose syrup obtained from liquefied starch substrate; f) glucose loss to maltulose formation is reduced; g) milliard reactions are eliminated or minimized; h) the risk of iodine positive starch polymer formation (Blue-Sac), after saccharification due to retrograded starch formation from jet cooking is lower; i) calcium addition to the starch slurry is eliminated; and j) filtration is improved because the hydrolyzed starch will not plug the filtration system. The methods and compositions encompassed by the invention offer a more economical and efficient means to produce glucose feed for industrial and specialty chemicals.

In one aspect of the invention a filamentous fungal strain transformed with a heterologous polynucleotide encoding a granular starch hydrolyzing enzyme having glucoamylase activity (GSHE) is provided. A preferred filamentous fungal strain is a *Trichoderma* strain and more specifically a *T. reesei* strain which expresses and secretes GSHE into the culture medium.

In some embodiments of this aspect, the invention pertains to a method of producing a GSHE in a filamentous host cell which comprises transforming the filamentous fungal host cell with a DNA construct comprising a promoter having transcriptional activity in the filamentous fungal host cell operably linked to a heterologous polynucleotide encoding a GSHE, cultivating the transformed filamentous fungal host cell in a suitable culture medium to allow expression of the GSHE and producing the GSHE. In other embodiments, the heterologous polynucleotide encoding the GSHE is derived from a strain of *Humicola grisea* or a strain of *Aspergillus awamori*. In other embodiments, the GSHE has at least 90% sequence identity to SEQ ID NO: 3 or at least 90% identity to SEQ ID NO: 6. In further embodiments, the GSHE produced by the recombinant host cell is recovered.

In a second aspect, the invention includes a fermentation broth produced from a culture of recombinant *Trichoderma reesei*, wherein the *T. reesei* comprises a heterologous polynucleotide encoding a GSHE having at least 90% sequence identity to SEQ ID NO: 3 or at least 90% sequence identity to SEQ ID NO: 6.

In a third aspect, the invention pertains to a one-step process for producing a glucose syrup from a granular starch substrate, the process comprising (a) contacting a slurry of a granular starch substrate having a dry solid content (ds) of 10-55% simultaneously with an alpha amylase and a granular starch hydrolyzing enzyme having glucoamylase activity (GSHE), at a temperature equal to or below the gelatinization temperature of the starch substrate, and (b) allowing the alpha amylase and the GSHE to act for a period of time sufficient to hydrolyze the granular starch to obtain a glucose syrup. In one embodiment, at least 95% of the granular starch is hydrolyzed. In a second embodiment, the yield of the glucose syrup is at least 90% by weight. In a third embodiment, the dry solid content of the granular starch substrate is between about 15 to 40%. In a fourth embodiment, the period of time to hydrolyze the granular starch is in the range of about 5 hours to 100 hours. In a fifth embodiment, the alpha amylase is an enzyme having EC 3.2.1.1. In a sixth embodiment, the alpha amylase is derived from a *Bacillus* and particularly a strain of *B. stearothermophilus*. In further embodiments, the alpha amylase is derived from a recombinant *Bacillus* strain. In a seventh embodiment, the GSHE is a glucoamylase derived from a *Humicola grisea* var. *thermoidea* strain or an *Aspergillus awamori* var. *kawachi* strain. In an eighth embodiment, the GSHE is a glucoamylase derived from a recombinant *Trichoderma* strain, and particularly a *T. reesei* strain which expresses a heterologous gene encoding a *Humicola grisea* GSHE or an *Aspergillus awamori* var. *kawachi* GSHE. In a ninth embodiment, the process further comprises separating the glucose syrup, particularly by filtration. In a tenth embodiment, the glucose from the glucose syrup is further converted to fructose. In an eleventh embodiment, the temperature of the one-step process is conducted at about 50 to about 70° C. In a twelfth embodiment, the pH of the process is conducted at pH 4.5 to 6.5.

In a fourth aspect, the invention relates to a one-step process for producing a glucose syrup from a granular cornstarch substrate, the process comprising (a) contacting a slurry of a granular starch substrate having a dry solid content (ds) of 25-45% simultaneously with an alpha amylase derived from a *Bacillus* and a glucoamylase having granular starch hydrolyzing activity which is derived from a fungal source, at a temperature of about 55 to 65° C. and a pH of about 5.0 to 6.0 and allowing the alpha amylase and the glucoamylase having granular starch hydrolyzing activity to act for a period of time sufficient to hydrolyze the granular starch to obtain a glucose syrup. In one embodiment, at least 80% of the granular starch is hydrolyzed and the yield of glucose syrup is at least 90% by weight. In a second embodiment, the glucoamylase is a GSHE derived from a recombinant *Trichoderma reesei* which expresses a heterologous polynucleotide encoding a *Humicola grisea* GSHE or an *Aspergillus awamori* var. *kawachi* GSHE.

In a fifth aspect, the invention relates to a method a hydrolyzing granular starch comprising contacting a slurry of granular starch having a dry solid content of 20-55% simultaneously with an alpha amylase and a glucoamylase having granular starch hydrolyzing activity obtained from a *Trichoderma* strain comprising a heterologous polynucleotide encoding a GSHE derived from *Humicola grisea* and allowing the alpha amylase and glucoamylase to act for a period of time sufficient to hydrolyze the granular starch. In one embodiment, at least 90% of the granular starch is hydrolyzed. In a second embodiment, the granular starch is cornstarch or wheat starch. In a third embodiment, the GSHE is provided to the slurry at a concentration of between about 0.5 to 1.0 GSHE units of *Humicola* GA/g starch; the alpha amylase is provided to the slurry at a concentration of between about 0.1 to 0.5 kg/MT of starch, the pH of the slurry is adjusted to about pH 4.5 to 6.0; and the temperature of the slurry is adjusted to about 55 to 65° C.

In a sixth aspect, the invention relates to a method for producing a glucose syrup comprising contacting a granular starch substrate simultaneously with an alpha amylase and a granular starch hydrolyzing enzyme (GSHE), wherein the GSHE is secreted from a filamentous fungal strain, said fungal strain comprising, a heterologous polynucleotide encoding a GSHE derived from a *Humicola* strain and having the amino acid sequence of at least 90% identity to SEQ ID NO: 3 to obtain a glucose syrup. In one embodiment, the glucose is further converted to a desired end product.

In a seventh aspect, the invention relates to an enzymatic composition comprising an alpha amylase and a glucoamylase having granular starch hydrolyzing activity. In one embodiment the alpha amylase is derived from a *Bacillus* sp. and the GSHE is derived from a *Humicola grisea* GSHE. In a second embodiment, the GSHE is derived from a *Trichoderma* strain genetically engineered to comprise a polynucleotide encoding a *Humicola grisea* GSHE. In a third embodiment, the pH of the composition is between pH 4.5 and 6.5. In a fourth embodiment, the alpha amylase is derived from a *B. stearothermophilus* strain. In further embodiment, the ratio of alpha amylase to GSHE in the enzyme composition is 15:1 to 1:15.

In an eighth aspect, the invention relates to a process for the production of a high fructose starch based syrup comprising converting the glucose syrup obtained by a method encompassed by the invention into a fructose based syrup.

In a ninth aspect, the invention relates to a method of producing an end product wherein the glucose syrup obtained by a method encompassed by the invention is subjected to fermentation. In some embodiments of this aspect, the end product is an alcohol, and preferably ethanol. In further embodiments of this aspect, the fermentation is carried out simultaneously with the contacting step and in other embodiments the fermentation is carried out separately and sequentially to the contacting step. In yet further embodiments, the fermentation product is separated from the fermentation broth.

In a tenth aspect, the invention relates to a method for producing residual starch by separating the glucose syrup produced according to the method of the invention and retaining the composition comprising residual starch. In one embodiment, the residual starch is used for the production of end products. In a second embodiment, the residual starch is recycled and simultaneously contacted with a GSHE and an alpha amylase at a temperature below the gelatinization temperature of the granular starch.

BRIEF DESCRIPTION OF THE DRAWINGS

FIG. 1 provides the genomic DNA sequence coding for the native *H. grisea* var. *thermoidea* granular starch hydrolyzing enzyme having glucoamylase activity (GSHE) (SEQ ID NO: 1). The putative introns are in bold and underlined.

FIG. 2A provides the signal sequence and mature amino acid sequence for *H. grisea* var. *thermoidea* GSHE (SEQ ID NO: 2). The putative signal sequence is in bold and underlined.

FIG. 2B provides the mature amino acid sequence for *H. grisea* var. *thermoidea* GSHE (SEQ ID NO: 3).

FIG. 4A, FIG. 4B, FIG. 4C, FIG. 4D, and FIG. 4E collectively depict the nucleotide sequence (SEQ ID NO: 11) (10738 bp) of the pTrex3g_N13 plasmid of FIG. 3.

FIG. 6 provides the genomic DNA sequence coding for the *Aspergillus awamori* var. *kawachi* GSHE (SEQ ID NO: 4). The putative introns are in bold and underlined.

FIG. 7A provides the signal sequence and mature amino acid sequence for *A. awamori* var. *kawachi* GSHE (SEQ ID NO: 5). The signal sequence is in bold and underlined.

FIG. 7B provides the mature amino acid sequence for *Aspergillus awamori* var. *kawachi* GSHE (SEQ ID NO: 6).

DETAILED DESCRIPTION OF THE INVENTION

Figure 3:
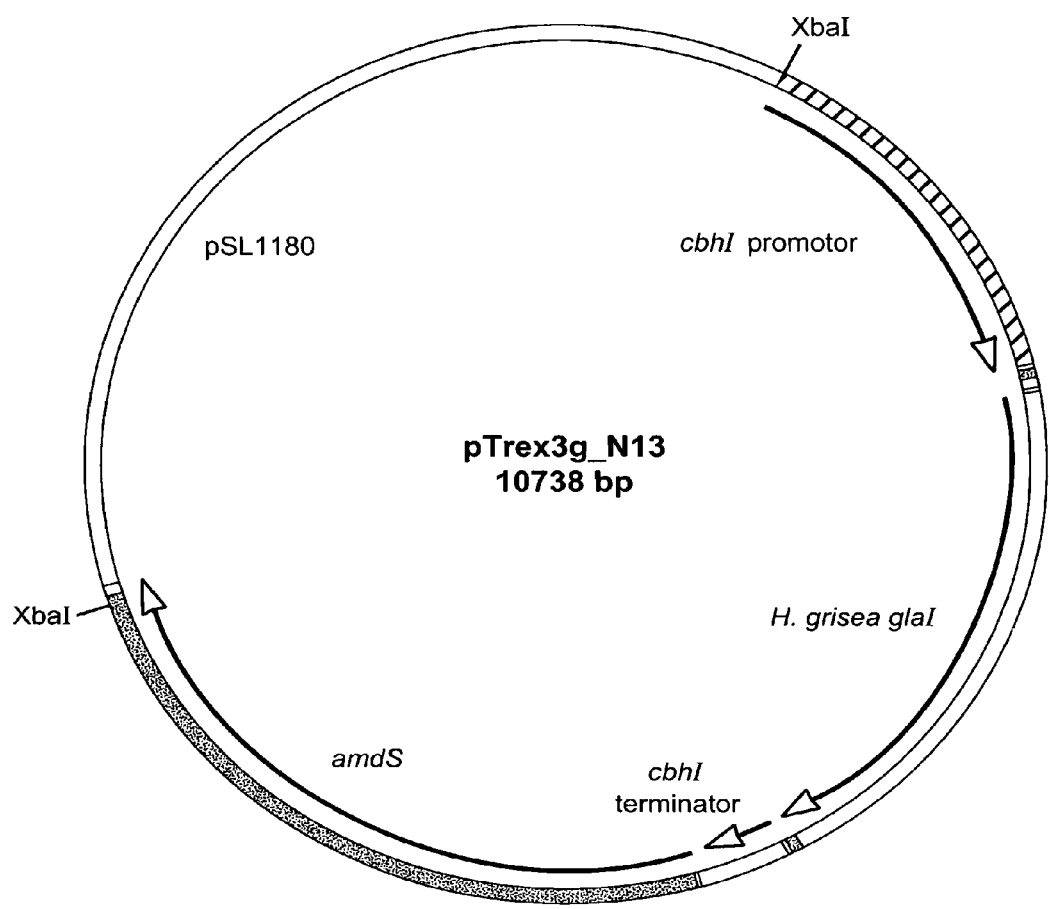
FIG. 3 provides an illustration of pTrex3g_N13 plasmid, which was used for expression of the nucleic acid encoding the *Humicola grisea* GSHE and which contains the XbaI sites flanking the fungal expression vector, wherein
   a) cbhI promoter is the *Trichoderma reesei* cellobiohydrolase promoter,
   b) *H. grisea* gla1 is the polynucleotide encoding the *Humicola grisea* GSHE of SEQ ID NO:3,
   c) cbhI terminator is the *Trichoderma reesei* cellobiohydrolase terminator,
   and d) amdS is an *Aspergillus nidulans* acetamidase marker gene.

In some aspects, the present invention relies on routine techniques and methods used in the field of genetic engineering and molecular biology. The following resources include descriptions of general methodology useful in accordance with the invention: Sambrook et al., MOLECULAR CLONING: A LABORATORY MANUAL (2nd Ed., 1989); Kreigler, GENE TRANSFER AND EXPRESSION; A LABORATORY MANUAL (1990) and Ausubel et al., Eds. CURRENT PROTOCOLS IN MOLECULAR BIOLOGY (1994).

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described.

The invention will now be described in detail by way of reference only using the following definitions and examples. All patents and publications, including all sequences disclosed within such patents and publications, referred to herein are expressly incorporated by reference.

Numeric ranges are inclusive of the numbers defining the range.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention, which can be had by reference to the specification as a whole.

A. DEFINITIONS

As used herein the term "starch" refers to any material comprised of the complex polysaccharide carbohydrates of plants, comprised of amylose and/or amylopectin with the formula $(C_6H_{10}O_5)_x$, wherein X can be any number. In particular, the term refers to any plant-based material including but not limited to grains, grasses, tubers and roots and more specifically the plants wheat, barely, corn, rye, rice, sorghum, legumes, cassava, millet, potato, sweet potato, and tapioca.

The term "granular starch" refers to uncooked (raw) starch, which has not been subject to gelatinization.

The term "starch gelatinization" means solubilization of a starch molecule to form a viscous suspension.

The term "gelatinization temperature" refers to the lowest temperature at which gelatinization of a starch substrate begins. The exact temperature depends upon the specific starch substrate and further may depend on the particular variety of plant species from which the starch is obtained and the growth conditions.

The term "DE" or "dextrose equivalent" is an industry standard for measuring the concentration of total reducing sugars, calculated as D-glucose on a dry weight basis. Unhydrolyzed granular starch has a DE that is essentially 0 and D-glucose has a DE of 100.

The term "glucose syrup" refers to an aqueous composition containing glucose solids. In one embodiment, glucose syrup will include at least 90% D-glucose and in another embodiment glucose syrup will include at least 95% D-glucose. In some embodiments, the terms "glucose", "glucose syrup" and "dextrose" are used interchangeably.

The term "total sugar content" refers to the total sugar content present in a starch composition.

The term "dry solids content (ds)" refers to the total solids of a slurry (in %) on a dry weight basis.

"Brix" refers to a well known hydrometer scale for measuring the sugar content of a solution at a given temperature. The Brix scale measures the number of grams of sucrose present per 100 grams of aqueous sugar solution (the total solublized solid content). Brix measurements are frequently made by use of a hydrometer or refractometer.

The term "starch-liquefying enzyme" refers to an enzyme that effects the fluidization of granular starch. Exemplary starch liquefying enzymes include alpha amylases (E.C. 3.2.1.1).

The term "amylases" refer to enzymes that catalyze the hydrolysis of starches.

The term "alpha-amylase (E.C. class 3.2.1.1)" refers to enzymes that catalyze the hydrolysis of alpha-1,4-glucosidic linkages. These enzymes have also been described as those effecting the exo or endohydrolysis of 1,4-α-D-glucosidic linkages in polysaccharides containing 1,4-α-linked D-glucose units. Another term used to describe these enzymes is glycogenase. Exemplary enzymes include alpha-1,4-glucan 4-glucanohydrase glucanohydrolase.

The terms "saccharification enzyme" and "glucoamylase" used interchangeability herein refer to the amyloglucosidase class of enzymes (EC.3.2.1.3, glucoamylase, alpha-1,4-D-glucan glucohydrolase). These are exo-acting enzymes, which release glucosyl residues from the non-reducing ends of amylose and amylopectin molecules. The enzymes also hydrolyze alpha-1,6 and alpha-1,3 linkages although at much slower rates than alpha-1,4 linkages.

The term "granular starch hydrolyzing enzyme (GSHE)" or "an enzyme having granular starch hydrolyzing activity" as used herein specifically refers to an enzyme having glucoamylase activity and having the ability to hydrolyze starch in granular form. Preferred GSHEs are those derived from filamentous fungi wherein the GSHE is endogenous or exogenous to the filamentous fungal cell. One preferred GSHE is the native GSHE derived from *Humicola grisea* var. *thermoidea*. Another preferred GSHE is derived from *Aspergillus awamori* var. *kawachi*. A particularly preferred GSHE is a recombinant GSHE, that is a GSHE expressed in a host strain that has been genetically engineered to include a heterologous polynucleotide encoding the GSHE. In some preferred embodiments, the GSHE is expressed as an extracellular enzyme.

The term "hydrolysis of starch" refers to the cleavage of glucosidic bonds with the addition of water molecules.

The term "degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. A DP4$^+$ (>DP3) denotes polymers with a degree of polymerization of greater than 3.

The term "contacting" refers to the placing of the respective enzymes in sufficiently close proximity to the respective substrate to enable the enzymes to convert the substrate to the end product. Those skilled in the art will recognize that mixing solutions of the enzyme with the respective substrates can effect contacting.

The term "enzymatic conversion" in general refers to the modification of a substrate by enzyme action. The term as used herein also refers to the modification of a granular starch substrate by the action of an enzyme. In a preferred embodiment, the enzymatic conversion of a granular starch substrate will result in a glucose syrup.

The term "slurry" refers to an aqueous mixture containing insoluble starch granules.

The term "glycosylation" refers to the post-transcriptional modification of a protein by the addition of carbohydrate moieties, wherein the carbohydrate is either N-linked or O-linked resulting in a glucoprotein. An N-linked carbohydrate moiety of a glycoprotein is attached by a glycosidic bond to the β-amide nitrogen of an asparagine residue. An O-linked carbohydrate is attached by a glycosidic bond to a protein through the hydroxy group of a serine or a threonine residue.

The term "recombinant" when used with reference e.g. to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The terms "recombinant GSHE", "recombinantly expressed GSHE" and "recombinantly produced GSHE" refer to a mature GSHE protein sequence that is produced in a host cell from a heterologous polynucleotide. The symbol "r" may be used to denote recombinant. The protein sequence of a rGSHE excludes a signal sequence. In one embodiment *Humicola grisea* var. *thermoidea* GSHE expressed in a strain of *Trichoderma reesei* is denoted by "rH-GSHE".

The terms "native GSHE" and "nGSHE" mean a GSHE, which was derived from a microbial host organism other than the fungal host for which recombinant GSHE expression is desired. Preferred native GSHEs are derived from a *Humicola grisea* strain or a *Aspergillus awamori* strain.

The terms "protein" and "polypeptide" are used interchangeably herein. The conventional one-letter or three-letter code for amino acid residues is used herein.

A "signal sequence" means a sequence of amino acids bound to the N-terminal portion of a protein, which facilitates the secretion of the mature form of the protein outside the cell. The definition of a signal sequence is a functional one. The mature form of the extracellular protein lacks the signal sequence which is cleaved off during the secretion process.

A "gene" refers to a DNA segment that is involved in producing a polypeptide and includes regions preceding and following the coding regions as well as intervening sequences (introns) between individual coding segments (exons).

The term "nucleic acid" encompasses DNA, RNA, single stranded or double stranded and chemical modifications thereof. The terms "nucleic acid" and "polynucleotide" may be used interchangeably herein. Because the genetic code is degenerate, more than one codon may be used to encode a particular amino acid, and the present invention encompasses polynucleotides, which encode a particular amino acid sequence.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" as used herein means a DNA construct comprising a DNA sequence which is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

A "promoter" is a regulatory sequence that is involved in binding RNA polymerase to initiate transcription of a gene. The promoter may be an inducible promoter or a constitutive promoter. A preferred promoter used in the invention is *Trichoderma reesei* cbh1, which is an inducible promoter.

"Under transcriptional control" is a term well understood in the art that indicates that transcription of a polynucleotide sequence, usually a DNA sequence, depends on its being operably linked to an element which contributes to the initiation of, or promotes transcription.

"Under translational control" is a term well understood in the art that indicates a regulatory process that occurs after mRNA has been formed, As used herein when describing proteins and genes that encode them, the term for the gene is not capitalized and is italicized, e.g. the gene that encodes the *Humicola grisea* GSHE may be denoted as gla1. The term for the protein is generally not italicized and the first letter is capitalized, e.g. the protein encoded by the gla1 gene may be denoted as Gla1.

The term "operably linked" refers to juxtaposition wherein the elements are in an arrangement allowing then to be functionally related. For example, a promoter is operably linked to a coding sequence if it controls the transcription of the sequence.

The term "selective marker" refers to a gene capable of expression in a host that allows for ease of selection of those hosts containing an introduced nucleic acid or vector. Examples of selectable markers include but are not limited to antimicrobials (e.g. hygromycin, bleomycin, or chloramphenicol) or genes that confer a metabolic advantage, such as a nutritional advantage on the host cell.

The term "derived" encompasses the terms "originated from", "obtained or obtainable from", and "isolated from".

"Host strain" or "host cell" means a suitable host for an expression vector or DNA construct comprising a polynucleotide encoding a GSHE according to the invention. Specifically, host strains are filamentous fungal cells. In a preferred embodiment of the invention, "host cell" means both the cells and protoplasts created from the cells of a filamentous fungal strain and particularly a *Trichoderma* sp. or an *Aspergillus* sp.

The term "filamentous fungi" refers to all filamentous forms of the subdivision Eumycotina (See, Alexopoulos, C. J. (1962), INTRODUCTORY MYCOLOGY, New York: Wiley). These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic. In the present invention, the filamentous fungal parent cell may be a cell of a species of, but not limited to, *Trichoderma*, e.g., *Trichoderma reesei* (previously classified as *T. longibrachiatum* and currently also known as *Hypocrea jecorina*), *Trichoderma viride, Trichoderma koningii, Trichoderma harzianum; Penicillium* sp.; *Humicola* sp., including *Humicola insolens* and *Humicola grisea; Chrysosporium* sp., including *C. lucknowense; Gliocladium* sp.; *Aspergillus* sp., including *A. oryzae, A. nidulans, A. niger,* and *A. awamori;*

*Fusarium* sp., *Neurospora* sp., *Hypocrea* sp., and *Emericella* sp. Reference is also made to Innis et al., (1985) *Sci.* 228:21-26.

As used herein, the term "*Trichoderma*" or "*Trichoderma* sp." refer to any fungal strain, which had previously been classified as *Trichoderma* or is currently classified as *Trichoderma*.

The term "culturing" refers to growing a population of microbial cells under suitable conditions in a liquid or solid medium. In one embodiment, culturing refers to fermentative bioconversion of a granular starch substrate to glucose syrup or other desired end products (typically in a vessel or reactor).

The term "heterologous" or "exogenous" with reference to a polynucleotide or protein refers to a polynucleotide or protein that does not naturally occur in a host cell. In some embodiments, the protein is a commercially important industrial protein. It is intended that the term encompass proteins that are encoded by naturally occurring genes, mutated genes and/or synthetic genes. The term "homologous" or "endogenous" with reference to a polynucleotide or protein refers to a polynucleotide or protein that occurs naturally in the host cell.

The terms "recovered", "isolated", and "separated" as used herein refer to a molecule, protein, cell, nucleic acid, amino acid, or carbohydrate that is removed from at least one component with which it is naturally associated.

As used herein, the terms "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein the term "specific activity" means an enzyme unit defined as the number of moles of substrate converted to product by an enzyme preparation per unit time under specific conditions. Specific activity is expressed as units (U)/mg of protein.

As used herein "enzyme activity" refers to the action of an enzyme on its substrate.

As used herein the term "enzyme unit" refers to the amount of enzyme that converts 1 mg of substrate per minute to the substrate product at optimum assay conditions. For example, in one embodiment, the term granular starch hydrolyzing enzyme unit (GSHE U) is defined as being the amount of GSHE required to produce 1 mg of glucose per minute from granular starch under assay conditions of, for example 50° C. at pH 4.5. For example, in one embodiment, the term alpha amylase enzyme unit (AU) is defined as the amount of alpha amylase which hydrolyzes 1 micromole of starch substrate in 1 min under standard assay conditions of pH 5.2 and 40° C.

The terms "end product" or "desired end-product" refer to any carbon-source derived molecule product which is enzymatically converted from the granular starch substrate. Preferably, the end product is glucose or a glucose syrup. Glucose may then be used as a precursor for other desired end-products.

The term "residual starch" as used herein refers to the by-product or remaining components of the inventive granular starch hydrolysis process when the composition comprising the glucose syrup or other end products is separated. The residual starch includes remaining insoluble starch, left in the composition after the separation.

A "residual starch recycling step" refers to the recycling of residual starch into a vessel or reactor, which includes a GSHE and an alpha amylase.

The term "yield" refers to the amount of end-product or desired end-products produced using the methods of the present invention. In some preferred embodiments, the yield is greater than that produced using methods known in the art. In some embodiments, the term refers to the volume of the end product and in other embodiment the term refers to the concentration of the end product.

As used herein "ethanologenic microorganism" refers to a microorganism with the ability to convert a sugar or oligosaccharide to ethanol. An ethanologenic microorganism is ethanologenic by virtue of their ability to express one or more enzymes that individually or together convert sugar to ethanol.

In the present context, the term "substantially pure polypeptide" means a polypeptide preparation which contains at the most 10% by weight of other polypeptide material with which it is natively associated (lower percentages of other polypeptide material are preferred, e.g. at the most 8% by weight, at the most 6% by weight, at the most 5% by weight, at the most 4% at the most 3% by weight, at the most 2% by weight, at the most 1% by weight, and at the most ½% by weight). Thus, it is preferred that the substantially pure polypeptide is at least 92% pure, i.e. that the polypeptide constitutes at least 92% by weight of the total polypeptide material present in the preparation, and higher percentages are preferred such as at least 94% pure, at least 95% pure, at least 96% pure, at least 96% pure, at least 97% pure, at least 98% pure, at least 99%, and at the most 99.5% pure. The polypeptides disclosed herein are preferably in a substantially pure form. In particular, it is preferred that the polypeptides disclosed herein are in "essentially pure form", i.e. that the polypeptide preparation is essentially free of other polypeptide material with which it is natively associated. This can be accomplished, for example, by preparing the polypeptide by means of well-known recombinant methods.

"ATCC" refers to American Type Culture Collection located at Manassas, Va. 20108 (ATCC, www/atcc.org).

"NRRL" refers to the Agricultural Research Service Culture Collection, National Center for Agricultural Utilization Research (and previously known as USDA Northern Regional Research Laboratory), Peoria, Ill.

"A", "an" and "the" include plural references unless the context clearly dictates otherwise.

As used herein the term "comprising" and its cognates are used in their inclusive sense; that is, equivalent to the term "including" and its corresponding cognates.

B. PREFERRED EMBODIMENTS

Starch Substrates—

A granular starch substrate to be processed in the methods of the invention may be obtained from any plant part including stems, grains, roots and tubers. Particularly preferred plant sources include corn; wheat; rye; sorghum; rice; millet; barley; cassava; legumes, such as beans and peas; potatoes;

sweet potatoes; bananas; and tapioca. The starch may be highly refined raw starch or feedstock from starch refinery processes. Specifically contemplated starch substrates are cornstarch and wheat starch. Those of general skill in the art are well aware of available methods which may be used to prepare granular starch substrates for use in the methods encompassed by the invention. Some of these available methods include dry milling of whole cereal grains using hammer mills and roller mills and wet milling.

Various starches are commercially available. For example, cornstarches are available from Cerestar, Sigma, and Katayama Chemical Industry Co. (Japan); wheat starches are available from Sigma; sweet potato starches are available from Wako Pure Chemical Industry Co. (Japan); and potato starch is available from Nakaari Chemical Pharmaceutical Co. (Japan).

While not meant to limit the invention in any manner, Table 1 below provides a general guide to the level of starch found in some common cereal grains. As one of ordinary skill in the art is well aware the level of starch in a grain may vary depending on such factors as genotype and environment.

TABLE 1

Starch Content of Various Grains

| Raw Material | Starch % |
|---|---|
| Corn | 60-68 |
| Wheat | 60-65 |
| Oats | 50-53 |
| Barley | 55-65 |
| Milo | 60-65 |
| Potato | 10-25 |
| Cassava | 25-30 |
| Rye | 60-65 |
| Rice (polished) | 70-72 |
| Sorghum (millet) | 75-80 |

The Alcohol Textbook, 3$^{rd}$ Ed. K. Jacques et al., Eds. 1999, Nottingham University Press, pg. 11.

In some embodiments of the methods encompassed by the invention, the granular starch substrate is slurried (generally with water) and the slurry comprises i) about 10 to about 55% dry solids content, ii) about 20 to about 50% dry solids content; iii) about 25 to about 45% dry solids content; iv) about 30 to about 45% dry solids content; v) about 30 to about 40% dry solids content; and vi) about 30 to 35% dry solids content.

Alpha Amylases—

In some of the embodiments encompassed by the invention, the alpha amylase is a microbial enzyme having an E.C. number, E.C. 3.2.1.1-3 and in particular E.C. 3.2.1.1. In some embodiments, the alpha amylase is a thermostable bacterial alpha amylase. Suitable alpha amylases may be naturally occurring as well as recombinant and mutant alpha amylases. In particularly preferred embodiments, the alpha amylase is derived from a *Bacillus* species. Preferred *Bacillus* species include *B. subtilis, B. stearothermophilus, B. lentus, B. licheniformis, B. coagulans*, and *B. amyloliquefaciens* (U.S. Pat. No. 5,763,385; U.S. Pat. No. 5,824,532; U.S. Pat. No. 5,958,739; U.S. Pat. No. 6,008,026 and U.S. Pat. No. 6,361,809). Particularly preferred alpha amylases are derived from *Bacillus* strains *B. stearothermophilus, B. amyloliquefaciens* and *B. licheniformis*. Also reference is made to strains having ATCC 39709; ATCC 11945; ATCC 6598; ATCC 6634; ATCC 8480; ATCC 9945A and NCIB 8059.

Commercially available alpha amylases contemplated for use in the compositions and methods of the invention include; SPEZYME AA; SPEZYME FRED; GZYME G997 (Genencor International Inc.) and TERMAMYL 120-L, LC, SC and SUPRA (Novozyme Biotech).

As understood by those in the art, the quantity of alpha amylase used in the compositions and methods of the present invention will depend on the enzymatic activity of the alpha amylase. In general, an amount of about 0.01 to 5.0 kg of the alpha amylase is added to a metric ton (MT) of the raw material (granular starch substrate). This amount is approximately equivalent to 0.06 AU/g ds to 30 AU/g ds with a GZYME 997. In some embodiments, the alpha amylase is added in an amount about 0.05 to 5.0 kg; about 0.05 to 2.5 kg; about 0.1 to 2.5 kg; about 0.1 to 2.0 kg; about 0.1 to 1.5 kg; about 0.1 to 1.0 kg; about 0.5 to 5.0 kg and about 0.5 to 2.0 kg per metric ton. These values are approximately equal to 0.3 to 30 AU/g ds; 0.3 to 15 AU/g ds; 0.6 to 15 AU/g ds; 0.6 to 12 AU/g ds; 0.6 to 9 AU/g ds; 0.6 to 6 AU/g ds; 3 to 30 AU/g ds and also 3 to 12 AU/g ds with a GZYME 997. In further embodiments, other quantities are utilized, for example, generally an amount of between about 0.01 to 1.0 kg of GZYME 997 or SPEZYME FRED (Genencor International Inc.) is added to a metric ton of starch. In other embodiments, the enzyme is added in an amount between about 0.05 to 1.0 kg; between about 0.1 to 0.6 kg; between about 0.2 to 0.6 kg and between about 0.4 to 0.6 kg of GZYME 997 or SPEZYME FRED per metric ton of starch.

Granular Starch Hydrolyzing Enzymes Having Glucoamylase Activity—

Glucoamylases (E.C. 3.2.1.3) are enzymes that remove successive glucose units from the non-reducing ends of starch. The enzyme can hydrolyze both linear and branched glucosidic linkages of starch, amylose and amylopectin. While glucoamylase may be derived from bacteria, plants and fungi, preferred glucoamylases encompassed by the present are derived from fungal strains.

Glucoamylases secreted from fungi of the genera *Aspergillus, Rhizopus, Humicola* and *Mucor* have been derived from fungal strains, including *Aspergillus niger, Aspergillus awamori, Rhizopus niveus, Rhizopus oryzae, Mucor miehe, Humicola grisea, Aspergillus shirousami* and *Humicola (Thermomyces) laniginosa* (See, Boel et al. (1984) *EMBO J.* 3:1097-1102; WO 92/00381; WO 00/04136; Chen et al., (1996) *Prot. Eng.* 9:499-505; Taylor et al., (1978) *Carbohydrate Res.* 61:301-308 and Jensen et al., (1988) *Can. J. Microbiol.* 34:218-223).

Enzymes having glucoamylase activity used commercially are produced for examples, from *Aspergillus niger* (trade name OPTIDEX L-400 and G ZYME G990 4X from Genencor International Inc.) or *Rhizopus* species (trade name CU.CONC. from Shin Nihon Chemicals, Japan and trade name GLUCZYME from Amano Pharmaceuticals, Japan).

A particular group of enzymes having glucoamylase activity are granular starch hydrolyzing enzyme(s) GSHE (See, Tosi et al., (1993) *Can. J. Microbiol.* 39:846-855). GSHEs not only have glucoamylase activity, but also are able to hydrolyze granular (raw) starch. GSHEs have been recovered from fungal cells such as *Humicola* sp., *Aspergillus* sp. and *Rhizopus* sp. A *Rhizopus oryzae* GSHE has been described in Ashikari et al., (1986) *Agric. Biol. Chem.* 50:957-964 and U.S. Pat. No. 4,863,864. A *Humicola grisea* GSHE has been described in Allison et al., (1992) *Curr. Genet.* 21:225-229 and European Patent No. 171218. The gene encoding this enzyme is also known in the art as gla1. An *Aspergillus awamori* var. *kawachi* GSHE has been described by Hayashida et al., (1989) *Agric. Biol. Chem* 53:923-929. An *Aspergillus shirousami* GSHE has been described by Shibuya et al., (1990) *Agric. Biol. Chem.* 54:1905-1914.

In one embodiment a GSHE may be derived from a strain of *Humicola grisea*, particularly a strain of *Humicola grisea* var. *thermoidea* (see, U.S. Pat. No. 4,618,579).

In some preferred embodiments, the GSHE is recovered from fungi including ATCC 16453, NRRL 15219, NRRL 15220, NRRL 15221, NRRL 15222, NRRL 15223, NRRL 15224 and NRRL 15225 as well as genetically altered strains thereof. (EP 0 171218).

In one embodiment, a GSHE may be derived from a strain of *Aspergillus awamori*, particularly a strain of *A. awamori* var. *kawachi* (See, Hayashida et al., (1989) *Agric. Biol. Chem.* 53:923-929).

In another embodiment, a GSHE may exhibit a maximum pH activity within a pH range of 4 to 7.5 and within a pH range of 5.0 to 7.5 and a maximum activity in the temperature range of 50 to 60° C.

In one embodiment, the GSHE has at least 50%, 55%, 60%, 65%, 70%, 75%, 80%, 85%, 90%, 93%, 95%, 97%, 98% and 99% sequence identity with the amino acid sequence set forth in SEQ ID NO: 3. In another embodiment, the GSHE comprises an amino acid sequence having at least 80% sequence identity with the sequence set forth in SEQ ID NO: 3. In other embodiments, the GSHE comprising the amino acid sequence of SEQ ID NO: 3 or a GSHE having at least 80% sequence identity with the sequence of SEQ ID NO: 3 is encoded by a polynucleotide having at least 70%, 80%, 85%, 90%, 93%, 95%, 97%, 98% and 99% sequence identity with SEQ ID NO: 1.

In another embodiment, the GSHE has at least 50%, 55%, 60%, 65%, 70%, 75%, 80%, 85%, 90%, 93%, 95%, 97%, 98% and 99% sequence identity with the amino acid sequence set forth in SEQ ID NO: 6. In another embodiment, the GSHE comprises an amino acid sequence having at least 80% sequence identity with the sequence set forth in SEQ ID NO: 6. In other embodiments, the GSHE comprising the amino acid sequence of SEQ ID NO: 6 or a GSHE having at least 80% sequence identity with the sequence of SEQ ID NO: 6 is encoded by a polynucleotide having at least 70%, 80%, 85%, 90%, 93%, 95%, 97%, 98% and 99% sequence identity with SEQ ID NO: 4.

A polynucleotide or polypeptide having a certain percent (e.g., 80%, 85%, 90% or 99%) of sequence identity with another sequence means that when aligned, that percent of bases or amino acid residues are the same in comparing the two sequences. This alignment and the percent homology or identity can be determined using any suitable software program known in the art, for example those described in Current Protocols in Molecular Biology (Ausubel et al., eds 1987 Supplement 30, section 7.7.18). Preferred programs include GCG Pileup program, FASTA and BLAST. Another preferred alignment program is ALIGN Plus and TFASTA.

One skilled in the art will recognize that sequences encompassed by the invention are also defined by the ability to hybridize under stringent hybridization conditions with the exemplified GSHE sequences (e.g. SEQ ID NO: 1 or SEQ ID NO: 4). A nucleic acid is hybridizable to another nucleic acid sequence when a single stranded form of the nucleic acid can anneal to the other nucleic acid under appropriate conditions of temperature and solution ionic strength. Hybridization and washing conditions are well known in the art (See, e.g. Sambrook (1989) supra, particularly chapters 9 and 11). In some embodiments, stringent conditions correspond to a Tm of 65° C. and 0.1×SSC, 0.1% SDS. In a further embodiment, a GSHE enzyme may be derived from a strain of *Rhizopus*. Such as the enzyme derived from the Koji strain of *R. niveus* (sold under the trade name "CU CONC") or the enzyme from *Rhizopus* sold under the trade name GLUCZYME.

In a preferred embodiment, the GHSE used in a method or composition encompassed by the invention is a recombinantly expressed GSHE obtained from a filamentous fungal strain, which has been genetically engineered to express a heterologous polynucleotide that encodes a GSHE derived from a source other than the host strain.

In some embodiments the filamentous fungal strain is a strain of *Aspergillus* sp., *Trichoderma* sp., *Fusarium* sp., or *Penicillium* sp. Particularly preferred fungal hosts include *A. nidulans, A. awamori, A. oryzae, A. aculeatus, A. niger, A. japonicus, T. reesei, T. viride, F. oxysporum*, and *F. solani*. *Aspergillus* strains are disclosed in Ward et al., (1993) *Appl. Microbiol. Biotechnol.* 39:738-743 and Goedegebuur et al., (2002) *Curr. Gene* 41:89-98. In a most preferred embodiment, the host is a *Trichoderma* strain and particularly a *T. reesei* strain. Strains of *T. reesei* are known and nonlimiting examples include ATCC No. 13631, ATCC No. 26921, ATCC No. 56764, ATCC No. 56765, ATCC NO. 56767 and NRRL 15709. In some preferred embodiments, the host strain is a derivative of RL-P37. RL-P37 is disclosed in Sheir-Neiss et al., (1984) *Appl. Microbiol. Biotechnol.* 20:46-53.

A host strain which expresses rGSHE may have be previously manipulated through genetic engineering. In some embodiments, various genes of the fungal host have been inactivated. These genes include, for example genes encoding cellulolytic enzymes, such as endoglucanases (EG) and exocellobiohydolases (CBH) (e.g., cbh1, cbh2, egl1, egl2 and egl3). U.S. Pat. No. 5,650,322 discloses derivative strains of RL-P37 having deletions in the cbh1 gene and the cbh2 gene.

In some embodiments, the fungal host has been genetically engineered to comprise a polynucleotide encoding a GSHE derived from *Humicola grisea*. In one embodiment the rGSHE will have at least 50%, 55%, 60%, 65%, 70%, 75%, 80%, 85%, 90%, 93%, 95%, 97%, 98% and 99% sequence identity to the amino acid sequence set forth in SEQ ID NO: 3. In other embodiments, a polynucleotide encoding the GSHE of SEQ ID NO: 3 will have at least 70%, 80%, 85%, 90%, 95%, 97% and 98% sequence identity with the sequence of SEQ ID NO: 1. In a particularly preferred embodiment, the GSHE is expressed in a *Trichoderma reesei* strain and the produced protein has at least 80%, 85%, 90%, 95%, 97% and 98% sequence identity with the sequence of SEQ ID NO: 3.

In other embodiments, the fungal host has been genetically engineered to express a polynucleotide encoding a GSHE derived from *Aspergillus awamori*. In one embodiment, the rGSHE will have at least 50%, 55%, 60%, 65%, 70%, 75%, 80%, 85%, 90%, 93%, 95%, 97%, 98% and 99% sequence identity to the amino acid sequence set forth in SEQ ID NO. 6. In other embodiments, a polynucleotide encoding the GSHE of SEQ ID NO: 6 will have at least 70%, 80%, 85%, 90%, 95%, 97% and 98% sequence identity with the sequence of SEQ ID NO: 4. In a particularly preferred embodiment, the GSHE is expressed in a *Trichoderma reesei* strain and the produced protein has at least 80%, 85%, 90%, 95%, 97% and 98% sequence identity with the sequence of SEQ ID NO: 6.

In some embodiments, the level of glycosylation of the recombinantly expressed GSHE is different that the level of glycosylation of the corresponding native GSHE (e.g., GSHE which was originally derived from *H. grisea* or *A. awamori* has a different level of glycosylation than the level of glycosylation of the GSHE expressed in *Trichoderma*). In one embodiment, the level of glycosylation is different even if the rGSHE has at least 80%, 85%, 90%, 95% amino acid identity to the corresponding native GSHE. In some embodiments, a rGSHE expressed in *Trichoderma* and particularly a strain of T. reesei has a different level of glycosylation than the level from the corresponding nGSHE. In other embodiments, the level of glycosylation is higher, while in other embodiments it is lower.

For example, the level of glycosylation for rGSHE may be at least 1%, 5%, 10%, 15%, 20%, 25%, 30%, 35%, 40%, 45%, 50%, 55%, 60%, or 65% less than the level of glycosylation of the corresponding nGSHE. In other embodiments, the level of glycosylation of an expressed rGSHE may be at least 1%, 5%, 10%, 15%, 20%, 25%, 30%, 35%, 40%, 50%, 60%, 70%, 80%, 100%, 125% 150%, 175%, 200%, 225% or 250% greater than the level of a corresponding nGSHE.

In another embodiment, the recombinantly produced GSHE produced according to the invention may have greater stability at lower pH levels than the corresponding native GSHE at optimum temperature levels. More specifically, a rGSHE expressed in *Trichoderma*, which was originally derived from *Humicola grisea* var. *thermoidea*, has a greater stability at pH levels of 3.5 to 4.0 compared to a corresponding nGSHE at a temperature of 45-55° C. Under some conditions the stability of rGSHE and particularly *H. grisea* var. *thermoidea* SEQ ID NO: 1 expressed in *Trichoderma reesei* is more than double the level of stability of nGSHE.

Vectors and Fungal Transformation:

According to the invention, a DNA construct comprising a polynucleotide encoding a GSHE encompassed by the invention is constructed to transfer GSHE into a host cell. Thus, a GSHE polynucleotide which can be expressed in enzyme form may be introduced into a host cell using a vector, particularly an expression vector which comprises a regulatory sequence operably linked to a GSHE coding sequence.

The vector may be any vector which when introduced into a fungal host cell is integrated into the host cell genome and is replicated. Reference is made to the Fungal Genetics Stock Center Catalogue of Strains (www.FGSC.net) for a list of vectors. Also, examples of suitable expression vectors may be found in Sambrook et al., (1989) supra, and Ausubel (1987) supra, and more specifically reference is made to van den Hondel et al. (1991) in Bennett and Lasure Eds. MORE GENE MANIPULATIONS IN FUNGI, Academic Press pp. 396-428. Particularly useful vectors include pFB6, pBR322, PUC18, pUC100 and pENTR/D.

In some embodiments, a nucleic acid encoding a GSHE is operably linked to a suitable promoter, which shows transcriptional activity in the fungal host cell. The promoter may be derived from genes encoding proteins either homologous or heterologous to the host cell. Preferably, the promoter is useful in a *Trichoderma* host and suitable nonlimiting examples of promoters include cbh1, cbh2, egl1, egl2. In one embodiment, the promoter is one that is native to the host cell. For example, when *T. reesei* is the host, the promoter would be a native *T. reesei* promoter. In a preferred embodiment, the promoter is *T. reesei* cbh1, which is an inducible promoter and has been deposited in GenBank under Accession No. D86235. An inducible promoter is a promoter that is active under environmental or developmental regulation. In another embodiment the promoter is one that is heterologous to the fungal host cell. Other examples of useful promoters include promoters from *A. awamori* and *A. niger glucoamylase* genes (See, Nunberg et al., (1984) *Mol. Cell Biol.* 4:2306-2315 and Boel et al., (1984) *EMBO J.* 3:1581-1585). Also, the promoters of the *T. reesei* xln1 gene and the cellobiohydrolase 1 gene may be useful (EPA 137280A1).

Figures 2A, 2B:
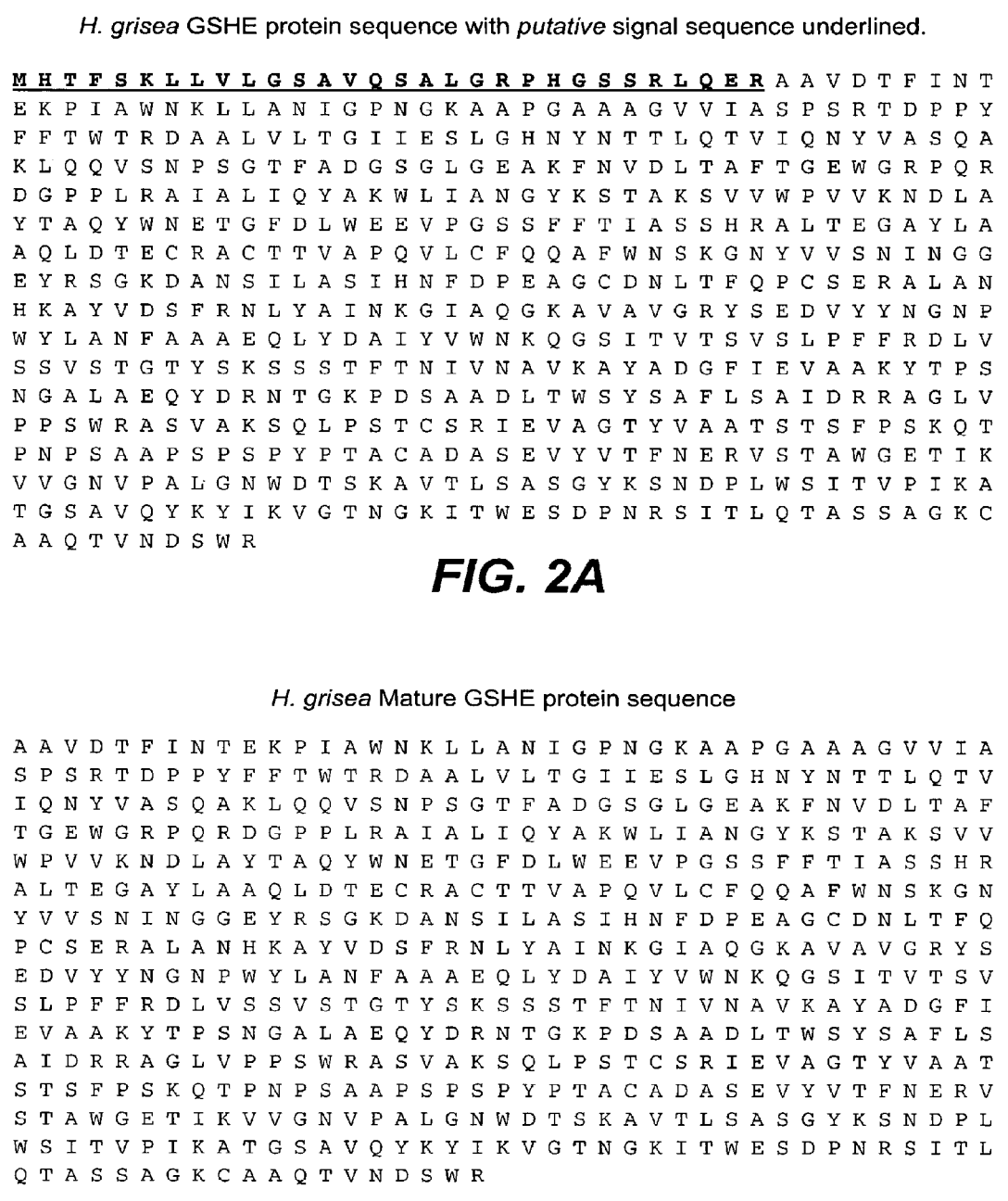

In some embodiments, the GSHE coding sequence is operably linked to a signal sequence. The DNA encoding the signal sequence is preferably that which is naturally associated with the GSHE gene to be expressed. Preferably, the signal sequence is encoded by a *Humicola grisea* or *Aspergillus awamori* gene which encodes a GSHE. More preferably the signal sequence has at least 90%, at least 95%, at least 97%, and at least 99% sequence identity to the signal sequence depicted in FIGS. 2A and 6A. In additional embodiments, a signal sequence and a promoter sequence comprising a DNA construct or vector to be introduced into a fungal host cell are derived from the same source. For example, in some embodiments, the signal sequence is the cdh1 signal sequence which is operably linked to a cdh1 promoter.

In some embodiments, the expression vector also includes a termination sequence. In one embodiment, the termination sequence and the promoter sequence are derived from the same source. In another embodiment, the termination sequence is homologous to the host cell. A particularly suitable terminator sequence is cbh1 derived from a *Trichoderma* strain and particularly *T. reesei*. Other useful fungal terminators include the terminator from *A. niger* or *A. awamori* glucoamylase gene (Nunberg et al. (1984) supra, and Boel et al., (1984) supra).

In some embodiments, an expression vector includes a selectable marker. Examples of preferred selectable markers include ones which confer antimicrobial resistance (e.g., hygromycin and phleomycin). Nutritional selective markers also find use in the present invention including those markers known in the art as amdS, argB and pyr4. Markers useful in vector systems for transformation of *Trichoderma* are described in Finkelstein, chapter 6 in BIOTECHNOLOGY OF FILAMENTOUS FUNGI, Finkelstein et al. Eds. Butterworth-Heinemann, Boston, Mass. (1992), Chap. 6. and Kinghorn et al. (1992) APPLIED MOLECULAR GENETICS OF FILAMENTOUS FUNGI, Blackie Academic and Professional, Chapman and Hall, London. In a preferred embodiment, the selective marker is the amdS gene, which encodes the enzyme acetamidase allowing transformed cells to grow on acetamide as a nitrogen source. (See, Kelley et al., (1985) *EMBO J.* 4:475-479 and Penttila et al., (1987) *Gene* 61:155-164.

An expression vector comprising a polynucleotide encoding a GSHE may be any vector which is capable of replicating autonomously in a given fungal host organism or of integrating into the DNA of the host. In some embodiments, an expression vector is a plasmid. In preferred embodiments, two types of expression vectors for obtaining expression of genes are contemplated.

The first expression vector comprises DNA sequences in which the promoter, GSHE coding region, and terminator all originate from the gene to be expressed. In some embodiments, gene truncation is obtained by deleting undesired DNA sequences (e.g., coding for unwanted domains) to leave the domain to be expressed under control of its own transcriptional and translational regulatory sequences.

The second type of expression vector is preassembled and contains sequences required for high-level transcription and a selectable marker. In some embodiments, the coding region for a GSHE gene or part thereof is inserted into this general-purpose expression vector such that it is under the transcriptional control of the expression constructs promoter and terminator sequences. In some embodiments, genes or part thereof are inserted downstream of the strong cbh1 promoter.

Methods used to ligate a vector comprising a polynucleotide encoding a GSHE, a promoter, a terminator and other sequences and to insert them into a suitable vector are well known in the art. Linking is generally accomplished by ligation at convenient restriction sites. If such sites do not exist, the synthetic oligonucleotide linkers are used in accordance with conventional practice. (See, Sambrook (1989) supra, and Bennett and Lasure, MORE GENE MANIPULATIONS IN FUNGI, Academic Press, San Diego (1991) pp 70-76.) Additionally, vector can be constructed using known recombination techniques (e.g. Invitrogen Life Technologies, Gateway Technology).

Where it is desired to obtain a fungal host cell having one or more inactivated genes known methods may be used (See, U.S. Pat. No. 5,246,853; U.S. Pat. No. 5,475,101 and WO 92/06209). Gene inactivation may be accomplished by complete or partial deletion, by insertional inactivation or by any other means which renders a gene nonfunctional for its intended purpose (such that the gene is prevented from expression of a functional protein). Any gene from a *Trichoderma* sp. or other filamentous fungal host, which has been cloned can be deleted, for example cbh1, cbh2, egl1 and egl2. In some embodiments, gene deletion is accomplished by inserting a form of the desired gene to be inactivated into a plasmid by known methods. The deletion plasmid is then cut at an appropriate restriction enzyme site(s), internal to the desired gene coding region and the gene coding sequence or part thereof id replaced with a selectable marker, Flanking DNA sequences from the locus of the gene to be deleted remain on either side of the market (preferably about between 0.5 to 2.0 kb). An appropriate deletion plasmid will generally have unique restriction enzyme sites present therein to enable the fragment containing the deleted gene, including the flanking DNA sequences and the selectable marker gene to be removed as a single linear piece.

Introduction of a DNA construct or vector into a host cell includes techniques such as transformation; electroporation; nuclear microinjection; transduction; transfection, including lipofection mediated and DEAE-Dextrin mediated transfection; incubation with calcium phosphate DNA precipitate; high velocity bombardment with DNA-coated microprojectiles; and protoplast fusion. General transformation techniques are taught in Ausubel et al., (1987), supra chapter 9 and Sambrook (1989) supra. More specifically methods of transformation for filamentous fungi are disclosed in Campbell et al., (1989) *Curr. Genet.* 16:53-56. Specifically, to effect the expression of heterologous protein in *Trichoderma* reference is made to U.S. Pat. No. 6,022,725; U.S. Pat. No. 6,268,328; Harkki et al. (1991); *Enzyme Microb. Technol.* 13:227-233; Harkki et al., (1989) *Bio Technol.* 7:596-603; EP 244,234; and EP 215,594. Reference is also made to Nevalainen et al., "The Molecular Biology of *Trichoderma* and its Application to the Expression of Both Homologous and Heterologous Genes", in MOLECULAR INDUSTRIAL MYCOLOGY, Eds. Leong and Berka, Marcel Dekker Inc., NY (1992) pp. 129-148. Reference is also made to Cao et al., (2000) *Sci.* 9:991-1001 for transformation of *Aspergillus* strains.

Preferably genetically stable transformants may be constructed with vector systems whereby the nucleic acid encoding GSHE is stably integrated into a host strain chromosome. Transformants may then be purified by known techniques.

In one nonlimiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on solid non-selective medium (i.e. lacking acetamide), harvesting spores from this culture medium and determining the percentage of these spores which will subsequently germinate and grow on selective medium containing acetamide. Alternatively, other methods known in the art may be used to select transformants.

In one specific embodiment, the preparation of *Trichoderma* sp. for transformation involves the preparation of protoplasts from fungal mycelia. (See, Campbell et al., (1989) *Curr. Genet.* 16:53-56). In some embodiments, the mycelia are obtained from germinated vegetative spores and treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M and 1.2 M. It is preferable to use about a 1.2 M solution of sorbitol in the suspension medium.

Uptake of DNA into the host *Trichoderma* sp. strain is dependent upon the calcium ion concentration. Generally between about 10 mM $CaCl_2$ and 50 mM $CaCl_2$ is used in an uptake solution. Besides the need for the calcium ion in the uptake solution, other items generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes thus permitting the contents of the medium to be delivered into the cytoplasm of the *Trichoderma* sp. strain and the plasmid DNA is transferred to the nucleus. This fusion frequently leaves multiple copies of the plasmid DNA tenderly integrated into the host chromosome.

Usually a suspension containing the *Trichoderma* sp. protoplasts or cells that have been subjected to a permeability treatment at a density of $10^5$ to $10^7$/mL, preferably $2 \times 10^6$/mL are used in transformation. A volume of 100 µL of these protoplasts or cells in an appropriate solution (e.g., 1.2 M sorbitol; 50 mM $CaCl_2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation. Similar procedures are available for other fungal host cells. See, for example, U.S. Pat. Nos. 6,022,725 and 6,268,328, the contents of which are hereby incorporated by reference.

Generally, the mixture is then incubated at approximately 0° C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated either at room temperature or on ice before the addition of a sorbitol and $CaCl_2$ solution. The protoplast suspension is then further added to molten aliquots of a growth medium. This growth medium permits the growth of transformants only.

Cell Culture—

Appropriate host cells are generally cultured in a standard medium containing physiological salts and nutrients, such as described in Pourquie, J. et al., BIOCHEMISTRY AND GENETICS OF CELLULOSE DEGRADATION, eds. Aubert, J. P. et al., Academic Press, pp. 71-86, 1988 and Ilmen, M. et al., (1997) *Appl. Environ. Microbiol.* 63:1298-1306. Also reference is made to common commercially prepared media such as Yeast Malt Extract (YM) broth, Luria Bertani (LB) broth and Sabouraud Dextrose (SD) broth.

Culture conditions are also standard, e.g., cultures are incubated at approximately 28° C. in appropriate media in shaker cultures or fermenters until desired levels of GSHE expression are achieved. Preferred culture conditions for a given filamentous fungus may be found in the scientific literature and/or from the source of the fungi such as the American Type Culture Collection and Fungal Genetics Stock Center (www.FGSC.net).

After fungal growth has been established, the cells are exposed to conditions effective to cause or permit the expression of a GSHE and particularly a GSHE as defined herein. In cases where a GSHE coding sequence is under the control of an inducible promoter, the inducing agent, e.g., a sugar, metal salt or antibiotics, is added to the medium at a concentration effective to induce GSHE expression.

Industrial Uses of the rGSHE—Fermentations—

In some embodiments of the present invention, fungal cells expressing a heterologous GSHE are grown under batch or continuous fermentation conditions. A classical batch fermentation is a closed system, wherein the composition of the medium is set at the beginning of the fermentation and is not subject to artificial alterations during the fermentation. Thus, at the beginning of the fermentation the medium is inoculated with the desired organism(s). In this method, fermentation is permitted to occur without the addition of any components to the system. Typically, a batch fermentation qualifies as a "batch" with respect to the addition of the carbon source and attempts are often made at controlling factors such as pH and oxygen concentration. The metabolite and biomass compositions of the batch system change constantly up to the time the fermentation is stopped. Within batch cultures, cells progress through a static lag phase to a high growth log phase and finally to a stationary phase where growth rate is diminished or halted. If untreated, cells in the stationary phase eventually die. In general, cells in log phase are responsible for the bulk of production of end product.

A variation on the standard batch system is the "fed-batch fermentation" system, which also finds use with the present invention. In this variation of a typical batch system, the substrate is added in increments as the fermentation progresses. Fed-batch systems are useful when catabolite repression is apt to inhibit the metabolism of the cells and where it is desirable to have limited amounts of substrate in the medium. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and well known in the art.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in one embodiment, a limiting nutrient such as the carbon source or nitrogen source is maintained at a fixed rate an all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology.

Identification of GSHE Activity—

In order to evaluate the expression of a GSHE by a cell line that has been transformed with a heterologous polynucleotide encoding a GSHE encompassed by the invention, assays can be carried out at the protein level, the RNA level or by use of functional bioassays particular to glucoamylase activity and/or production. In general, assays employed to analyze the expression of a GSHE include, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of a GSHE may be measured in a sample directly, for example, by assays directly measuring reducing sugars such as glucose in the culture media and by assays for measuring glucoamylase activity, expression and/or production. Substrates useful for assaying GSHE activity include granular starch substrates. For example, glucose concentration may be determined by any convenient method such as by using glucose reagent kit No 15-UV (Sigma Chemical Co.) or an instrument such as Technicon Autoanalyzer. Also reference is made to glucose oxidase kits and glucose hexose kits commercially available from Instrumentation Lab. (Lexington, Mass.). Glucoamylase activity may be assayed by the 3,5-dinitrosalicylic acid (DNS) method (See, Goto et al., (1994) Biosci. Biotechnol. Biochem. 58:49-54). In one nonlimiting example, a rGSHE has the ability to hydrolyze granular starch in a 15% starch solids suspension in water to a solution of saccharides of at least 90%, 91%, 92%, 93%, 94%, 95%, 96%, 97%, 98% and 99% wt glucose, dry substance basis.

In an embodiment of the invention, the GSHE expressed by a recombinant host will be greater than 1 gram protein per liter (g/L) of culture media. Preferably in some embodiments, the host is a *Trichoderma* or an *Aspergillus* host. In some embodiments, the amount of GSHE expressed by a recombinant *Trichoderma* host will be greater than 2 g/L of culture media. In other embodiments, the amount of GSHE expressed by a recombinant *Trichoderma* host will be greater than 5 g/L of culture media. Yet in other embodiments the amount of GSHE expressed by a recombinant *Trichoderma* host will be greater than 10 g/L of culture media. The amount of expressed GSHE may in some instances be greater than 20 g/L, greater than 25 g/L, greater than 30 g/L and greater than 50 g/L of culture media.

In addition, protein expression, may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of a GSHE. The details of such methods are known to those of skill in the art and many reagents for practicing such methods are commercially available.

Exemplary assays include ELISA, competitive immunoassays, radioimmunoassays, Western blot, indirect immunofluorescent assays and the like. In general, commercially available antibodies and/or kits may be used for the quantitative immunoassay of the expression level of a GSHE.

Methods for Purifying GSHE—

In general, a GSHE (nGSHE or rGSHE) produced in cell culture is secreted into the medium and may be purified or isolated, e.g., by removing unwanted components from the cell culture medium. In some cases, a GSHE may be produced in a cellular form necessitating recovery from a cell lysate. In such cases the enzyme is purified from the cells in which it was produced using techniques routinely employed by those of skill in the art. Examples include, but are not limited to, affinity chromatography (Tilbeurgh et al., (1984) *FEBS Lett.* 16:215); ion-exchange chromatographic methods (Goyal et al., (1991) *Biores. Technol.* 36:37; Fliess et al., (1983) *Eur. J. Appl. Microbiol. Biotechnol.* 17:314; Bhikhabhai et al., (1984) *J. Appl. Biochem.* 6:336; and Ellouz et al., (1987) *Chromatography* 396:307), including ion-exchange using materials with high resolution power (Medve et al., (1998) *J. Chromatography A* 808:153; hydrophobic interaction chromatography (Tomaz and Queiroz, (1999) *J. Chromatography A* 865:123; two-phase partitioning (Brumbauer, et al., (1999) *Bioseparation* 7:287); ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75. The degree of purification desired will vary depending on the use of the GSHE. In some embodiments, purification will not be necessary.

In some embodiments, the recombinantly expressed GSHE is from a *Trichoderma* host. In other embodiments the *Trichoderma* host expresses a heterologous polynucleotide, which encodes a GSHE from a *Humicola grisea* strain, particularly a strain of *Humicola grisea* var. *thermoidea*. In other embodiments, the *Trichoderma* expresses a recombinant GSHE wherein the heterologous polynucleotide encodes a GSHE having at least 50% sequence identity with the sequence of SEQ ID NO:3.

In some embodiments, *Trichoderma* host expresses a heterologous polynucleotide, which encodes a GSHE from a *Aspergillus awamori* strain, particularly a strain of *A. awamori* var. *kawachi*. In other embodiments, the *Trichoderma* expresses a recombinant GSHE wherein the heterologous polynucleotide encodes a GSHE having at least 50% sequence identity with the sequence of SEQ ID NO:6.

Composition and Process Conditions—

Whether the GSHE is supplied in a cell free extract or supplied in the culture medium (fermentation broth), which includes fungal cells that express and secret GSHE, the granular starch substrate, preferably in slurry form is contacted with the GSHE and alpha amylase essentially simultaneously (referred to herein as simultaneously) to hydrolyze the granular starch and produce a glucose syrup. The hydrolysis of the granular starch is a one-step process.

A GSHE may be added to a composition comprising an alpha amylase and a granular starch substrate in an amount of between about 0.01 to 10.0 GSHE U/g starch dry solids of a slurry adjusted to 10-55% dry solids. In some embodiments, the GSHE is added in an amount of between about 0.01 and 5.0 GSHE U/g; about 0.01 and 2.0 GSHE U/g; about 0.01 and 1.5 GSHE U/g; about 0.05 and 1.5 GSHE U/g; about 0.1 and 5.0 GSHE U/g; about 0.1 and 1.0 GSHE U/g; about 0.25 and 2.5 GSHE U/g; about 0.5 and 5.0 GSHE U/g; and about 0.5 and 1.0 GSHE U/g of such solution. Also in some preferred embodiments, the GSHE is added in an amount of between about 0.05 and 1.5 GSHE U/g of such solution, also between 0.1 and 2.0 GSHE U/g and also between about 0.1 and 1.0 GSHE U/g.

In further embodiments, a GSHE is added to a granular starch slurry composition essentially simultaneously with alpha amylase wherein the slurry is adjusted to 10 to about 55% ds, preferably 20-45% ds and also 25-45% ds. In certain embodiments, the alpha amylase comprising the composition is added in a range of about 0.01 to 1.0 kg of GZYME 997 per metric ton of starch.

In one embodiment, the granular starch substrate is contacted with a GSHE wherein the GSHE is available as a cell free filtrate (such that the GSHE is isolated from the culture medium). In another embodiment, the granular starch substrate is contacted with a GSHE, wherein the GSHE is available in a culture medium containing the secreted GSHE and fungal cells. Preferably, the GSHE will be secreted from a *Trichoderma reesei* containing a heterologous polynucleotide encoding a polypeptide having granular starch hydrolyzing activity and at least 90%, at least 95% and at least 98% sequence identity with the sequence of SEQ ID NO: 3 or SEQ ID NO: 6.

The methods of the invention are conducted at a temperature equal to or below the gelatinization temperature of the granular starch of the substrate. In some embodiments, the method is conducted at a temperature of at least about 25° C., 30° C., 35° C., 40° C., 45° C., 50° C., 55° C., 60° C., 65° C., 70° C. and 75° C. In other embodiments, the method is conducted at a temperature less than about 65° C. and also less than about 60° C. In other embodiments, the method is conducted at a temperature of between about 30° C. and 65° C.; also between about 35° C. and 65° C.; between about 40° C. and 65° C.; between about 45° C. and 65° C.; and between about 50° C. and 65° C. The exact temperature used in accordance with the method depends upon the specific starch substrate and further may depend upon the particular plant variety. In some embodiments, when corn is the granular starch substrate the temperature is conducted at about between 55° C. and 65° and more particularly between 60° C. and 65° C.

Table 2 illustrates the general starch gelatinization temperature ranges for a number of starches. The table has been complied from various sources and is not meant to limit the invention, but is provided as a guide.

TABLE 2

Temperature Range for the Gelatinization of Starches

| Starch | Gelatinization Temperature Range ° C. |
|---|---|
| Barley | 52-59 |
| Wheat | 58-64 |
| Rye | 57-70 |
| Corn (maize) | 62-72 |
| High amylose corn | 67-80 |
| Rice | 68-77 |
| *Sorghum* | 68-77 |
| Potato | 58-68 |
| Tapioca | 59-69 |
| Sweet Potato | 58-72 |

(J. J. M. Swinkels pg 32-38 in STARCH CONVERSION TECHNOLOGY, Eds Van Beynum et al., (1985) Marcel Dekker Inc. New York and The Alcohol Textbook 3$^{rd}$ ED. A reference for the beverage, fuel and industrial alcohol industries, Eds Jacques et al., (1999) Nottingham University Press, UK)

The pH range at which the methods of the invention is conducted is in the range of about pH 3.0 to pH 6.5; also the range of pH 3.5 to pH 6.5; the range of pH 4.0 to pH 6.5; and the range of pH 4.5 to pH 6.0 are used in the methods. The pH range is somewhat dependent of the specific enzymes and one skilled in the art would be able to determine the best pH range for conducting the methods without undue experimentation. In some embodiments, when corn is the substrate the pH range is about pH 4.5 to pH 6.0 and also about pH 5.0 to pH 5.5.

In some embodiments, at least 50%, 55%, 60%, 65%, 70%, 75%, 80%, 85%, 90%, 94%, 95%, 96%, 97%, 98% and 99% of the dry solids of the granular starch is converted into a composition of glucose syrup. In some embodiments, the granular starch substrate is completely hydrolyzed. In certain embodiments, at least 90% of the granular starch substrate is hydrolyzed in a time period of 24 hours. In other embodiments, at least 95% of the granular starch substrate is hydrolyzed in a time period of 24 hours. In other embodiments, the dextrose syrup produced according to the invention will be about 32 to 46% ds syrup containing at least 90% glucose.

In some embodiments, the period of time required to hydrolyze the granular starch to produce a glucose syrup is from about 2 to 100 hours. In some embodiments, the period of time is about 5 to 100 hours. In other embodiments, the period of time is from about 10 to 100 hours. In still other embodiments, the period of time is from 5 to 50 hours. In other embodiments, the period of time is at least about 10 hours but less than about 50 hours. In preferred embodiments, the one-step process will be conducted from 2 to 100 hours and in some embodiments, the process will be conducted from 5 hours to 50 hours.

Preferably, the yield of glucose in the solublized composition (glucose percent of the total solublized dry solids) is at least about 85%, 90%, 91%, 92%, 93%, 94%, 95%, 95.5%, 96%, 96.5%, 97%, 97.5%, 98%, 98.5%, 99% and 99.5%. More preferably, the yield is at least about 95% and most preferably, the yield is at least about 96%.

The exact amounts of the components encompassed by the composition and methods of the invention depend on the combination of enzymes applied as well as the type of granular starch processed. In some embodiments, the ratio of alpha amylase units to GSHE units (alpha amylase:GSHE) will be in the range of 15:1 to 1:15 and in some embodiments in the range of 10:1 to 1:10. In other embodiments, the ratio will be in the range of 5:1 to 1:5 and in further embodiments, the alpha amylase:GSHE will be 4:1 to 1:4. In preferred embodiments, the ratio will be about 2:1 to 1:4 and most preferably about 2:1 to 1:2.

The one-step process encompassed by the invention can include the addition of further ingredients without reducing the effectiveness of the hydrolysis of granular starch. These further ingredients include but are not limited to other enzymes, such as cellulases, proteases, pullulanases, hemicellulase, xylanases and the like.

The glucose produced according to the method of the invention may be separated from the reaction mixture by methods known in the art. Some of these methods include centrifugation, conventional filtration methods and preferably membrane separation processes. Also mentioned is the use of ultrafiltration membrane systems. In one preferred embodiment, the glucose syrup is separated by filtration using a molecular weight cut-off (MWCO) ultrafiltration membrane. These membranes are known in the art. In some embodiments, the membrane could be 1,000 to 1,000,000 MWCO. In other embodiments, the separation membrane may be a 0.1 to 1.0 microfilter type membrane.

Further Conversion of Glucose to Desired End Products—

In a method encompassed by the invention, glucose syrup is the preferred end product. However, the glucose may be further purified to yield crystalline dextrose by known methods.

The glucose may also be converted to other desired end products. Conversion of glucose to other desired end products may be accomplished by any suitable method such as, enzymatic or chemical methods. In one embodiment, conversion is accomplished by bioconversion of glucose by contacting glucose obtained according to the invention with a microorganism capable of converting the glucose to an end product. The contacting step may be a sequential step, wherein the glucose syrup produced by the method of the invention is then contacted with a microorganism to produce an end product, or the contacting step may be a simultaneous step, wherein the granular starch substrate is contacted with the GSHE and alpha amylase enzyme in combination with a microorganism capable of converting the glucose syrup produced by the enzyme conversion to an end-product. The microorganism may be a wild-type, mutated or recombinant microorganism. In some embodiments, the desired end products are fructose, ascorbic acid (ASA) intermediates, such as gluconate, 2-keto-D-gluconate, 2,5-diketo-D-gluconate, 2-keto-L-gulonic acid, idonic acid, erythorbic acid and ascorbic acid; ethanol, 1,3-propanediol, monosodium glutamate, amino acids, sugars alcohols, organic acids, and indigo.

When fructose is the desired end-product, the glucose syrup obtained according to the present invention may be enzymatically converted to a fructose syrup by a glucose isomerase. In some embodiments, the glucose isomerase is immobilized. Contemplated glucose isomerases include those commercially available such as G ZYME™ G993 liquid and GENSWEET™ (Genencor International, Inc.) and SWEETZYME T (Novozyme). (See, e.g. U.S. Pat. No. 3,939,041 and U.S. Pat. No. 4,687,742).

When ASA intermediates and ASA are the desired end-products, the glucose syrup obtained according to the present invention may be enzymatically bioconverted to gluconate using for example, glucose dehydrogenase (or glucose oxidase-catalase enzymes. Gluconate may be oxidized to 2,5-diketo-D-gluconate (DKG) by a DKG reductase. DKG may be reduced to 2-keto-L-gulonic acid (KLG) by a KLG reductase. KLG may then be converted to ASA. Methods for converting glucose to ASA and ASA intermediates are well known (See, for example U.S. Pat. No. 4,945,052, U.S. Pat. No. 5,008,193; U.S. Pat. No. 5,817,490 and U.S. Pat. No. 6,358,715).

When 1,3-propanediol is the desired end-product, glucose obtained according to the invention may be contacted with *E. coli* or other recombinant microorganisms (See, for example U.S. Pat. No. 6,013,494, U.S. Pat. No. 5,356,812).

When ethanol is the desired end-product, glucose may be contacted either sequentially or simultaneously with an ethanologenic microorganism, such as the yeast *Saccharomyces cerevisiae* to obtain ethanol. (See, for example U.S. Pat. No. 4,316,956). Further examples of ethanologenic microorganisms, which can be used in the methods of the invention, are those expressing alcohol dehydrogenase and pyruvate decarboxylase such as *Zymomonas mobilis* (See, for example U.S. Pat. Nos. 5,028,539; 5,424,202; 5,487,989 and 5,514,583). Upon completion of the fermentation with yeast, the ethanol may be recovered, for example by distillation, and used for potable, fuel and industrial ethanol products. By-products of the fermentation include both liquid and solid material that can be separated and further used. For example, the recovered solid material, such as distiller's dried grain (DDG) and the mixture of DDS with liquid by-products to form distiller's dried grain with solubles (DDGS) may be used as an animal feed. The use of yeast for the production of ethanol during fermentation and ethanol production is further discussed in THE ALCOHOL TEXTBOOK, A REFERENCE FOR THE BEVERAGE, FUEL AND INDUSTRIAL ALCOHOL INDUSTRIES, $3^{rd}$ Edition, Eds K. A. Jacques et al., 1999, Nottingham University Press, UK.

In some embodiments of the invention, when the glucose syrup is separated from the reaction mixture by for example, centrifugation or filtration as mentioned above, the remaining composition will include residual starch. The residual starch by-product may be used in various applications. For example, residual starch may be recycled and used as a component in a method according to the invention; the residual starch may be used as a carbon feedstock in further fermentations; the residual starch may be used in a conventional starch hydrolysis process; and the residual starch may be used as an ingredient for food formulations. One preferred embodiment of the invention comprises simultaneously contacting a granular starch substrate with a GSHE and an alpha amylase at a temperature below the gelatinization of the granular starch to hydrolyze the granular starch to obtain a glucose syrup, separating the glucose syrup from the reaction mixture to obtain a glucose syrup component and a by-product component which includes residual starch.

In some embodiments, according to the invention, when the residual starch is recycled in a recycling step and used in the method encompassed by the invention, the residual starch will be simultaneously contacted with a composition comprising a GSHE and an alpha amylase at a temperature below the gelatinization temperature of the granular starch substrate. The residual starch component may include enzymes that have been retained by the separation membrane and/or GSHE and alpha amylase enzymes that are newly added to the reactor. In some embodiments, the recycling step in combination with the simultaneous contacting step may be repeated numerous times and further may take place under continuous recycling conditions wherein the glucose syrup is separated by means known in the art. The contacting time of the various components in a reactor or vessel would be the same as outlined above that is from 2 to 100 hours. In some preferred embodiments, the residence time would be between 5 and 50 hours.

In the recycling step embodiment, the residual starch may be recycled to obtain glucose syrup. In one non-limiting example, a granular starch slurry (i.e. a corn starch slurry having 38-42% ds) may be hydrolyzed with a *Humicola* GSHE (i.e., 1.0 GSHE U/g) and SPEZYME ethyl (i.e., 0.6 AU/g) at a temperature of about 58-62° C. and a pH of 5.0 to 6.0 for 20-24 hours, wherein at least 55% of the corn starch is hydrolyzed to produce a glucose syrup having at least 90% glucose. The residual starch may be recovered and resuspended and combined with a second round of GSHE and alpha amylase. In the second round, approximately at least 90% of the starch is hydrolyzed yielding at least 90% glucose. The glucose syrup may then be evaporated by means known in the art, such as by vacuum and then used as a glucose feed.

In the recycling step embodiment, the residual starch may be recycled to obtain end products other than glucose. For example, when the end product is ethanol, the granular starch substrate is contacted either separately and sequentially or simultaneously with GSHE, alpha amylase and an ethanologenic organism to both hydrolyze the granular starch and produce ethanol, the ethanol may be recovered by distillation and the remaining material which includes both solid and liquid material including residual starch may be recycled and used with the GSHE and alpha amylase in further steps such that the recycling takes place under continuous recycling conditions.

EXPERIMENTAL

In the disclosure and experimental section which follows, the following abbreviations apply: rH-GSHE (*Humicola grisea* var. *thermoidea* GSHE expressed in *Trichoderma reesei*); wt % (weight percent); ° C. (degrees Centigrade); rpm (revolutions per minute); $H_2O$ (water); $dH_2O$ (deionized water); by (base pair); kb (kilobase pair); kD (kilodaltons); gm (grams); µg (micrograms); mg (milligrams); ng (nanograms); µl (microliters); ml and mL (milliliters); mm (millimeters); nm (nanometers); µm (micrometer); M (molar); mM (millimolar); µM (micromolar); U (units); V (volts); MW (molecular weight); sec (seconds); min(s) (minute/minutes); hr(s) (hour/hours); PAGE (polyacrylamide gel electrophoresis); Di (deionized); phthalate buffer (sodium phthalate in water, 20 mM, pH 5.0); Cerestar (Cerestar, Inc., a Cargill Inc., Minneapolis, Minn.); AVICELL® (FMC Corporation); SDS (sodium dodecyl sulfate); Tris (tris(hydroxymethyl)aminomethane); w/v (weight to volume); v/v (volume to volume); Genencor (Genencor International, Inc., Palo Alto, Calif.); Shin Nihon (Shin Nihon, Japan).

General Methods:

Starch Substrates—Purified and/or refined cornstarch, wheat starch and tapioca starch were used in the examples provided below.

Oligosaccharides Analysis—The composition of the reaction products of oligosaccharides was measured by high pressure liquid chromatographic method (Beckman System Gold 32 Karat Fullerton, Calif., USA) equipped with a HPLC column (Rezex 8 u8% H, Monosaccharides), maintained at 50° C. fitted with a refractive index (RI) detector (ERC-7515A, RI Detector from The Anspec Company, Inc.). Dilute sulfuric acid (0.01 N) was used as the mobile phase at a flow rate of 0.6 ml per minute. Twenty microliter of 4.0% solution was injected on to the column. The column separates based on the molecular weight of the saccharides. For example a designation of DP1 is a monosaccharide, such as glucose; a designation of DP2 is a disaccharide, such as maltose; a designation of DP3 is a trisaccharide, such as maltotriose and the designation "DP4+" is an oligosaccharide having a degree of polymerization (DP) of 4 or greater.

Relative solubilization of the solids—A conventional low temperature jet cooking process was used to solubilize the starch (U.S. Pat. No. 3,912,590). The measured BRIX was taken as 100% solubilization of the starch under the defined parameters of starch to water ratio. In a typical jet cooking process, suspending 150 grams of starch in 350 grams of water made a 30% starch slurry. The pH was then adjusted to pH 5.8 using 10% NaOH. Thermostable alpha amylase, SPEZYME FRED (Genencor International Inc.) was added at 0.4 Kg/MT, ds and heated in a jet cooker maintained at 105° C. for 8 min. The gelatinized starch was further hydrolyzed at 95° C. for 90 min. An aliquot of the hydrolysate was withdrawn and centrifuged. The clear supernatant was used to measure the BRIX (ABBE Refractometer, American Optical Corporation, Scientific Instrument Division, Buffalo, N.Y.). The BRIX for 100% solublized starch for different starch substrate at 30% ds is given in Table 3 and used to calculate the percent relative solubilization of starch under different treatment conditions. Alternatively, BRIX for 100% solubilization under different conditions was determined by incubating 5 ml of an aliquot with 10 micro liter of SPEZYME FRED (Genencor International Inc,) at 95° C. for 5 min. The high temperature treated sample was kept at 85° C. for 2 hours. The insoluble solids were separated by centrifugation and the BRIX of the clear supernatant was measured.

TABLE 3

| BRIX For Enzyme jet cooked starch substrate at 30% slurry | |
|---|---|
| Enzyme jet cooked Starch substrate, 30% ds | Measured BRIX |
| Cornstarch | 28.2 |
| Wheat starch | 27.9 |
| Tapioca starch | 28.5 |

EXAMPLES

The following examples are provided in order to demonstrate and further illustrate certain preferred embodiments and aspects of the present invention and are not to be construed as limiting the scope thereof. Indeed, it is contemplated that these teachings will find use in further optimizing the process systems described herein.

Example 1

Expression of *Humicola grisea* Var. *Thermoidea* GSHE Gene in *Trichoderma reesei*

A. Cloning of the *Humicola grisea* Var. *Thermoidea* GSHE Gene

Genomic DNA (SEQ ID NO:1) was extracted from frozen *Scytalidium thermophilum* (ATCC 16453, anamorph, *H. grisea* var. *thermoidea*) mycelia. The frozen mycelia were ground with dry ice in a coffee grinder and the DNA was extracted by the EasyDNA protocol (Invitrogen). An extra chloroform/phenol/isoamyl alcohol extraction was added to the standard protocol. PCR primers were designed, based on the NCBI database accession #M89475 sequence. The forward primer contained a motif for directional cloning into the pENTR/D vector (Invitrogen).

The sequence of the RSH003f primer was CAACATG-CATACCTTCTCCAAGCTCCTC (SEQ ID NO. 7) and the sequence of the RSH004r primer was TTAACGCCAC-GAATCATTCA CCGTC (SEQ ID NO. 8).

The PCR product was cloned into pENTR/D, according to the Invitrogen Gateway system protocol. The vector was then transformed into chemically competent Top10 *E. coli* (Invitrogen) with kanamycin selection. Plasmid DNA from several clones was restriction digested to confirm the correct size insert. The gla1 insert was sequenced (Sequetech, Mountain View, Calif.) from several clones. Plasmid DNA from one clone, pENTR/D_N13, was added to the LR clonase reaction (Invitrogen Gateway system) with pTrex3g/amdS destination vector DNA. Recombination, in the LR clonase reaction, replaced the CmR and ccdB genes of the destination vector with the *H. grisea* gla1 from the pENTR/D vector. This recombination directionally inserted gla1 between the cbhI promoter and terminator of the destination vector. Recombination site sequences of 48 and 50 bp remained upstream and downstream, respectively, of gla1. An aliquot of the LR clonase reaction was transformed into chemically competent Top10 *E. coli* and grown overnight with carbenicillin selection. Plasmid DNA, from several clones, was digested with appropriate restriction enzymes to confirm the correct insert size. Plasmid DNA from clone, pTrex3g_N13 (see FIGS. 3 and 4) was digested with Xba1 to release the expression cassette including the cbhI promoter:gla1:cbhI terminator: amdS. This 6.6 kb cassette was purified by agarose gel extraction using standard techniques and transformed into a strain of *T. reesei* derived from the publicly available strain QM6a, as further described below.

The cassette was sequenced by Sequetech, Mountain View, Calif. and the DNA for GSHE is illustrated in FIG. 1 (SEQ ID NO:1) and the amino acid sequence illustrated in FIG. 2 (SEQ ID NOs:2 and 3).

B. Transformation of *T. reesei*—

Approximately 2 $cm^2$ of a plate of sporulated mycelia (grown on a PDA plate for 5 days at 30° C.) was inoculated into 50 ml of YEG (5 g/L yeast extract plus 20 g/L glucose) broth in a 250 ml, 4-baffle shake flask and incubated at 37° C. for 16-20 hours at 200 rpm. The mycelia were recovered by transferring the liquid volume into 50 ml conical tubes and spinning at 2500 rpm for 10 minutes. The supernatant was decanted. The mycelial pellet was transferred into a 250 ml, 0.22 micron CA Corning filter bottle containing 40 ml of filtered β-D-glucanase solution and incubated at 30° C., 200 rpm for 2 hrs to generate protoplasts for transformation.

Protoplasts were harvested by filtration through sterile miracloth into a 50 ml conical tube. They were pelleted by spinning at 2000 rpm for 5 minutes and aspirated. The protoplast pellet was washed once with 50 ml of 1.2 M sorbitol, spun down, aspirated, and washed with 25 ml of sorbitol/$CaCl_2$. Protoplasts were counted and then pelleted at 2000 rpm for 5 min, the supernate was decanted, and the protoplast pellet was resuspended in an amount of sorbitol/$CaCl_2$ sufficient to generate a protoplast concentration of $1.25 \times 10^8$ protoplasts per ml, generating a protoplast solution.

Aliquots of up to 20 µg of expression vector DNA (in a volume no greater than 20 µl) were placed into 15 ml conical tubes and the tubes were put on ice. Then 200 µl of the protoplast suspension was added along with 50 µl PEG solution to each transformation aliquot. The tubes were mixed gently and incubated on ice for 20 min. PEG solution (2 ml) was added to the transformation aliquot tubes, and these were incubated at room temperature for 5 minutes. Sorbitol/$CaCl_2$ (4 ml) solution was added to the tubes (generating a total volume of 6.2 ml). The transformation mixture was divided into 3 aliquots each containing about 2 ml. An overlay mixture was created by adding each of these three aliquots to three tubes of melted top agar (kept molten by holding at 50° C.) and this overlay mixture was poured onto a transformation plate. The transformation plates were then incubated at 30° C. for four to seven days.

The transformation was performed with amdS selection. Acetamide/sorbitol plates and top agar were used for the transformation. Top agar was prepared by the same Sorbitol/acetamide agar recipe as the plates, except that low melting agarose was used in place of Noble agar. Transformants were purified by transfer of isolated colonies to fresh selective media containing acetamide (i.e., Sorbitol/acetamide agar, without sorbitol).

With reference to the examples the solutions were prepared as follows.
1) 40 ml β-D-glucanase solution was made up in 1.2M sorbitol and included 600 mg β-D-glucanase (InterSpex Products Inc., San Mateo, Calif.) and 400 mg $MgSO_4.7H_2O$.
2) 200 ml PEG mix contained 50 g PEG 4000 (BDH Laboratory Supplies Poole, England) and 1.47 g $CaCl_2.2H_2O$ made up in $dH_2O$.
3) Sorbitol/$CaCl_2$ contained 1.2M sorbitol and 50 mM $CaCl_2$.
4) Acetamide/sorbitol agar:
    Part I—0.6 g acetamide (Aldrich, 99% sublime.), 1.68 g CsCl, 20 g glucose, 20 g $KH_2PO_4$, 0.6 g $MgSO_4.7H_2O$, 0.6 g $CaCl_2.2H_2O$, 1 ml 1000× salts (see below), adjusted to pH 5.5, brought to volume (300 mls) with $dH_2O$, filter sterilized.
    Part II—20 g Noble agar and 218 g sorbitol brought to volume (700 mls) with $dH_2O$ and autoclaved.
    Part II was added to part I for a final volume of 1 L.
5) 1000× Salts—5 g $FeSO_4.7H_2O$, 1.6 g $MnSO_4.H_2O$, 1.4 g $ZnSO_4.7H_2O$, 1 g $CoCl_2.6H_2O$ were combined and the volume was brought to 1 L with $dH_2O$. The solution was filter sterilized.

C. Fermentation of *T. reesei* Transformed with the *H. grisea* Var. *Thermoidea* GSHE Gene.

Figure 5:
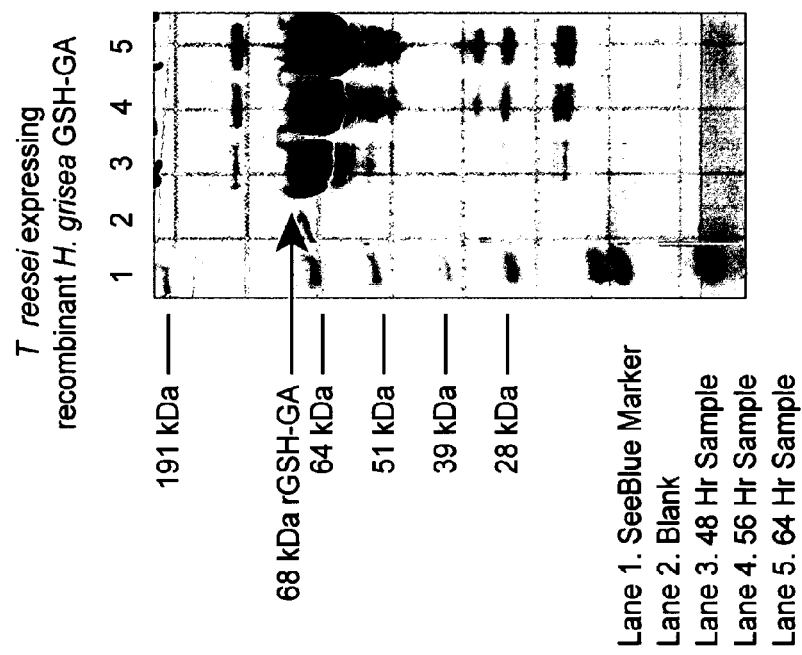
FIG. 5 provides an SDS-PAGE gel indicating the expression of *H. grisea* var. *thermoidea* GSHE in a representative fermentation run for *Trichoderma reesei* clones as described in Example 1. Lane 1 represents the commercial molecular weight marker, SeeBlue (Invitrogen); lane 2 is blank; lane 3 depicts rGSHE expression at 48 hours; lane 4 depicts rGSHE expression at 56 hours; and lane 5 depicts rGSHE expression at 64 hours.

In general, the fermentation protocol as described in Foreman et al. (Foreman et al. (2003) *J. Biol. Chem* 278:31988-31997) was followed. More specifically, duplicate fermentations were run for each of the strains displayed in FIG. 5. 0.8 L of Vogels minimal medium (Davis et al., (1970) Methods in Enzymology 17A, pg 79-143 and Davis, Rowland, NEUROSPORA, CONTRIBUTIONS OF A MODEL ORGANISM, Oxford University Press, (2000)) containing 5% glucose was inoculated with 1.5 ml frozen spore suspension. After 48 hours, each culture was transferred to 6.2 L of the same medium in a 14 L Biolafitte fermenter. The fermenter was run at 25° C., 750 RPM and 8 standard liters per minute airflow. One hour after the initial glucose was exhausted, a 25% (w/w) lactose feed was started and fed in a carbon limiting fashion to prevent lactose accumulation. The concentrations of glucose and lactose were monitored using a glucose oxidase assay kit or a glucose hexokinase assay kit with beta-galactosidase added to cleave lactose, respectively (Instrumentation Laboratory Co., Lexington, Mass.). Samples were obtained at regular intervals to monitor the progress of the fermentation. Collected samples were spun in a 50 ml centrifuge tube at ¾ speed in an International Equipment Company (Needham Heights, Mass.) clinical centrifuge.

Sample supernatants were run of 4-12% BIS-TRIS SDS-PAGE gels, under reducing conditions with MOPS (morpholinepropanesulfonic acid) SDS running buffer and LDS sample buffer. The results are provided in FIG. 5. Lanes 3, 4 and 5 illustrate a 68 kD rGSHE band at different time periods.

D. Assay of GSHE Activity from Transformed *Trichoderma reesei* Clones—

Enzyme activity—GSHE activity was determined as milligrams (mg) of reducing sugars released (measured as glucose equivalent) per minute (min) during an incubation of 5 ml of 10% granular cornstarch in a 0.1 M acetate buffer, pH 4.5, 50° C. with an aliquot of the enzyme preparation. One unit of GSHE is defined as 1.0 mg of reducing sugar released per min under the assay conditions.

Native GSHE (nGSHE) from *Humicola grisea* var. *thermoidea* and recombinant GSHE produced from *T. reesei* were purified by standard techniques using hydrophobic interaction chromatography using phenyl-sepharose (Amersham Biosciences, Piscataway, N.J.) followed by ion exchange chromatography using SP-sepharose (Amersham Biosciences, Piscataway, N.J.). The recombinant GSHE initially expressed by *T. reesei* clones included two protein peak fractions in about equal concentrations. These peaks were labeled rGSHE1 and rGSHE2. The two peaks differed in mass by 1500 D and by 0.3 pH units as measured by matrix assisted laser desorption and ionization (MALDI-TOF) on a voyageur mass spectrometer (Applied Biosystems, Foster City, Calif.) and an isoelectric focusing gel (SERVA Electrophoresis, GmbH, Heidelberg, Germany) according to manufacturer directions. Both rGSHE1 and rGSHE2 have the same specific activity as measured by the raw starch hydrolyzing assay and protein measurements using a MicroBCA protein assay kit (Pierce, Rockford, Ill.) and the percent solution extinction coefficient (A280 0.1%=1.963). After a period of time, measured at approximately 72 hours after initial rGSHE expression, only one form of rGSHE is represented (rGSHE3). (See, Table 4).

TABLE 4

| Source of GSHE | Specific Activity GSHE Units/mg | % total carbohydrate |
|---|---|---|
| Native GSHE | 9.0 | 1.12 |
| rGSHE1/rGSHE2 | 8.0/8.0 | 2.70 |
| rGSHE3 | 8.0 | 0.57 |

The % carbohydrate (CHO) of the GSHEs was determined by acid hydrolysis using 4N trifluoroacetic acid at 100° C. for 5 hrs and measurements were made of the released reducing sugars using parahydroxybenzoic acid hydrazide.

When initially expressed, the glycosylation of rGSHE1 and rGSHE2 was 2.70% of the total carbohydrate. However, after 72 hours, the level of glycosylation of rGSHE3 found in the medium was 0.57% total CHO. The level of glycosylation of native GSHE was 1.12%.

E. Comparison of Native GSHE from *H. grisea* Var. *Thermoidea* and Recombinantly Expressed *H. grisea* Var. *Thermoidea* GSHE in *Trichoderma reesei*.

(1) pH Stability was Determined from pH 3 to 7.

The collected samples of recombinantly produced GSHE as described above and samples of native GSHE were diluted to equal protein concentrations with 20 mM acetate buffer at pH 4.5. Reactions were then run in 100 mM citrate/NaOH buffers at 50° C. for 30 minutes at pH levels 3 to 7.

1.0 ml of the reaction was then added to 5 ml of 10% corn starch (Cargill Foods, Minneapolis, Minn.) in 100 mM acetate, pH 4.5 in sample tubes. The tubes were shaken at 50° C. for 20 minutes. Then 0.5 ml 2.0% NaOH was added. Tubes were spun and 0.5 ml of the supernatant was assayed for reducing sugars using the Dinitro Salicylic acid (DNS) assay (Goto et al., (1994) supra,).

Figure 8A:
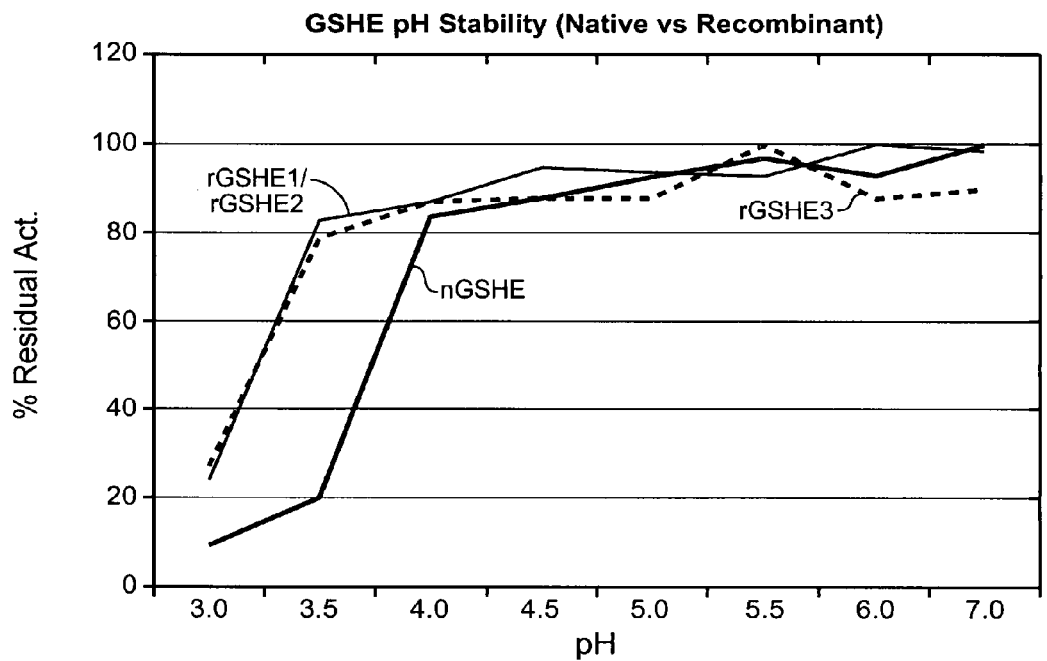
FIGS. 8A and 8B illustrate the pH stability as % residual activity for the native *Humicola grisea* var. *thermoidea* GSHE (nGSHE) and the expressed *H. grisea* var. *thermoidea* GSHE (RGSHE) in the *T. reesei* host (SEQ ID NO: 3), as described in Example 1.

The results of the assay are depicted in FIG. 8A. The recombinantly produced GSHE exhibited about 80% residual activity at pH 3.5. In comparison, the corresponding native GSHE exhibited only about 20% residual activity. At pH 4.0 both the recombinantly produced GSHE and the native GSHE exhibited about 82% residual activity and at pH 5.5 both enzymes exhibited between about 90 to 100% residual activity.

Figure 8B:
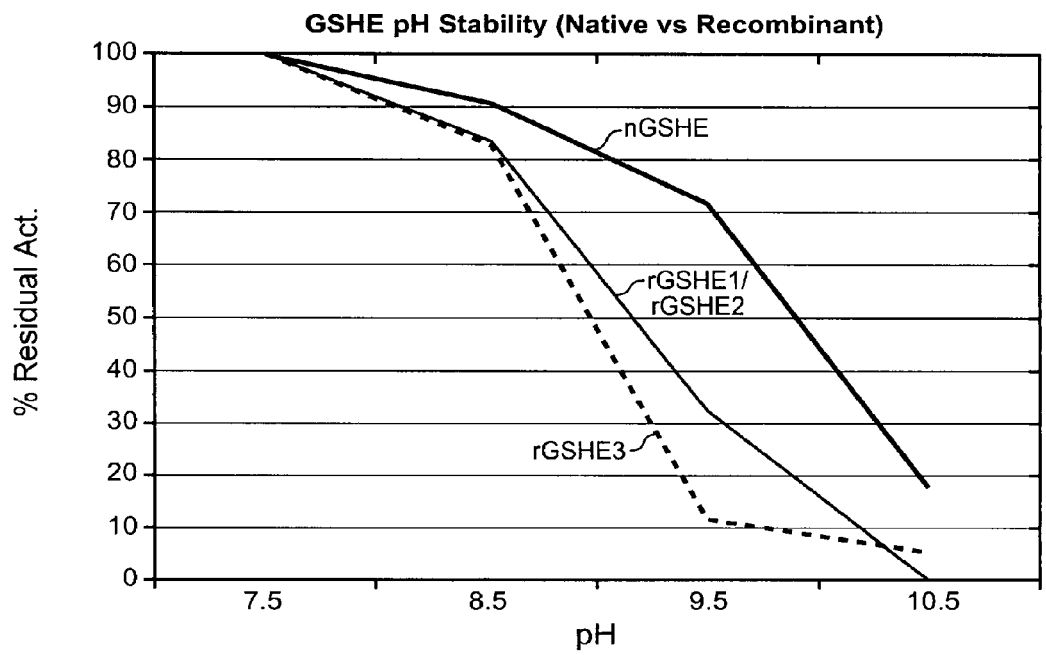

Stability was also measured at pH 7.5 to 10.5 using the methods as described above. However, the buffer was 100 mM boric acid/NaOH buffer. As exhibited in FIG. 8B, at pH 7.5 both enzymes exhibited about 100% residual activity. At pH 8.5 recombinantly produced GSHE exhibited about 82% residual activity and the native GSHE exhibited about 90% residual activity. At pH 9.5 the % residual activity of recombinantly produced GSHE was substantially less than the native GSHE. (10% compared to 72%, respectively).

(2) Profile of Activity as a Function of Temperature.

Temperature stability was determined at pH 5.75. Using essentially the same procedures as described above for the pH stability studies, enzyme samples were diluted to equal protein concentrations in a 100 mM acetate buffer and then 1.0 ml of the diluted enzymes was exposed to a water bath temperature of 40° C., 50° C., 60° C. and 70° C. for 10 minutes and assayed as described above in the pH stability studies. The results are presented in Table 5.

TABLE 5

| GSHE Source | Temp ° C. | % Residual Activity |
|---|---|---|
| Native GSHE | 40 | 100 |
|  | 50 | 95 |
|  | 60 | 90 |
|  | 70 | 0 |
| Recombinant GSHE | 40 | 100 |
|  | 50 | 93 |
|  | 60 | 92 |
|  | 70 | 0 |

% residual activity means the % difference referenced to 100% at pH 4.0

The profile of activity as a function of temperature of the recombinantly produced GSHE is similar to that of the corresponding native GSHE.

(3). Hydrolysis of Granular Corn Starch by nGSHE and rGSHE.

Figure 9:
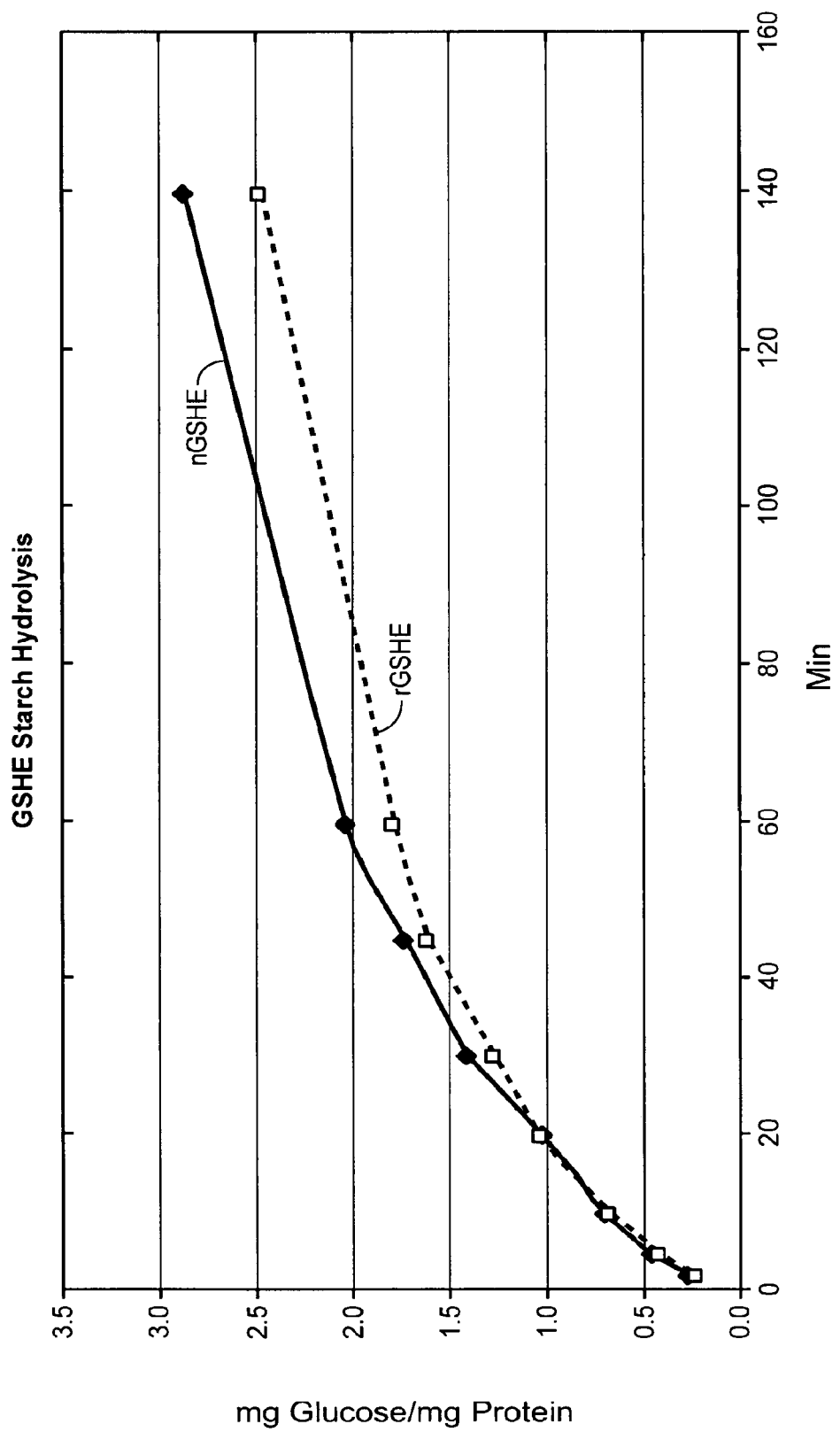
FIG. 9 illustrates the hydrolysis of corn starch measured as mg glucose/mg protein over time for native *Humicola grisea* var. *thermoidea* GSHE and the expressed *H. grisea* var. *thermoidea* GSHE in the recombinant *Trichoderma reesei* host as described in Example 1.
Figure 11:
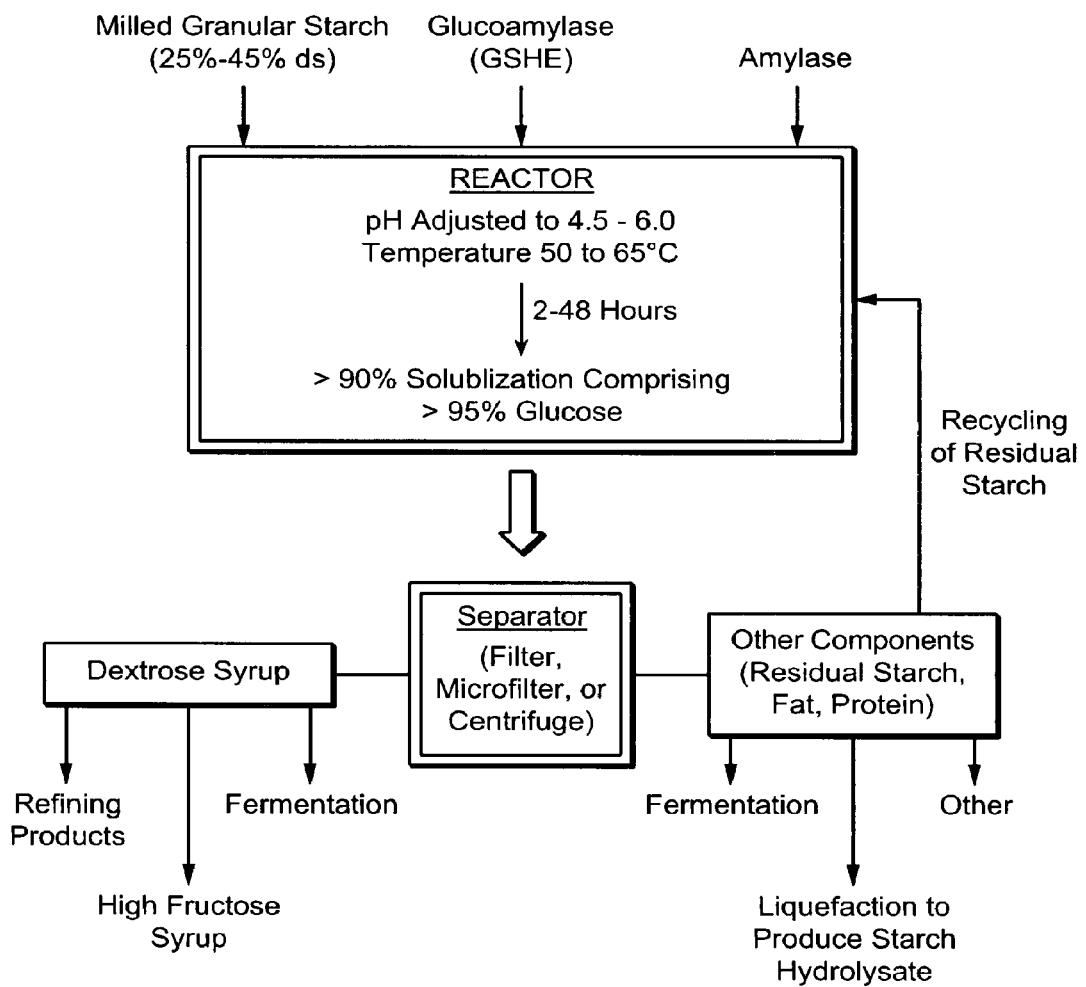
FIG. 11 is a general diagram illustrating an embodiment of the inventive process for low energy glucose production from granular starch substrates.

Both native GSHE from *H. grisea* var. *thermoidea* (nGSHE) and recombinantly expressed *H. grisea* var. *thermoidea* (rGSHE) in *Trichoderma reesei* were diluted to equal protein concentrations in pH 4.5 acetate buffer. One ml of the dilution was added to a 10% corn starch (Cargill Foods, Minneapolis, Minn.) slurry in 20 mM pH 4.5 acetate buffer and shaken at 350 rpm at 50° C. At designated time intervals 100 μL of slurry was removed and added to 10 μL of 2% NaOH. The sample was spun and the supernatant was assayed for glucose (mg glucose/mg protein) using the glucose oxidase reagent in a Monarch clinical analyzer (Instrumentation Laboratory, Lexington, Mass.). As shown in FIG. 9 the hydrolysis of corn starch was slightly lower for the rGSHE compared to the nGSHE.

Example 2

Expression of *Aspergillus awamori* Var. *Kawachi* GSHE Gene in *Trichoderma reesei*

A. Cloning the *Aspergillus awamori* Var. *Kawachi* GSHE Gene

Genomic DNA was extracted from frozen mycelia of a strain of *A. awamori* var. *kawachi* according to the methods described in Example 1. The PCR primer sequences were designed based on the published sequence of the *A. awamori* var. *kawachi* glucoamylase GAI (Hayashida, et al. (1989) *Agric. Biol. Chem.* 53:923-929). This GAI is a GSHE. The following primers were used: the RSH10f primer having the sequence, CAC CAT GTC GTT CCG ATC TCT TCT C (SEQ ID NO:9), which includes the Gateway (Invitrogen) directional cloning motif CACC and the RSH11r primer having the sequence, CTA CCG CCA GGT GTC GGT CAC (SEQ ID NO:10).

The DNA sequence is provided in FIG. 6 (SEQ ID NO:4). The encoded GSHE polypeptide sequence, including the signal peptide, is provided in FIG. 7A (SEQ ID NO:5) and the mature protein sequence is provided in FIG. 7B (SEQ ID NO:6).

The 2.16 kb PCR product was gel-purified (Gel Purification kit, Qiagen) and cloned into pENTR/D (Invitrogen), according to the Gateway system protocol. The vector was then transformed into chemically competent Top10 *E. coli* (Invitrogen) with kanamycin selection. Plasmid DNA from several clones was restriction digested to confirm the correct size insert. The GAI gene insert was sequenced (Sequetech, Mountain View, Calif.) from several clones (SEQ ID NO:4). Plasmid DNA from one clone, pENTR/D_Ak33xx#1, was added to the LR clonase reaction (Invitrogen Gateway system) with the pTrex3g/amdS destination vector DNA. Recombination, in the LR clonase reaction, replaced the $Cm^R$ and ccdB genes of the destination vector with the *A. kawachi* GAI from the pENTR/D vector. This recombination directionally inserted GAI between the cbhI promoter and terminator of the destination vector. AttB recombination site sequences of 48 and 50 bp remained upstream and downstream, respectively, of the glucoamylase. Reference is made to FIG. 3, wherein the *H. grisea* gla1 has been replaced by the *A. kawachi* GAI in this example. Two microliters of the LR clonase reaction were transformed into chemically competent Top10 *E. coli* and grown overnight with carbenicillin selection. Plasmid DNA from several clones was digested with XbaI to confirm the insert size. Plasmid DNA from clone, pTrex3g_Akxx #3 was digested with XbaI to release the expression cassette including the cbhI promoter:GAI:cbhI terminator:amdS. This 6.7 kb cassette was purified by agarose extraction using standard techniques and transformed into a strain of *T. reesei* derived from the publicly available strain QM6a.

B. Transformation of *T. reesei* with the *A. awamori* Var. *Kawachi* GSHE Gene

A *Trichoderma reesei* spore suspension was spread onto the center ~6 cm diameter of an MABA transformation plate (150 μl of a $5 \times 10^7$-$5 \times 10^8$ spore/ml suspension). The plate was then air dried in a biological hood. Stopping screens (BioRad 165-2336) and macrocarrier holders (BioRad 1652322) were soaked in 70% ethanol and air dried. DriRite desiccant was placed in small Petri dishes (6 cm Pyrex) and overlaid with Whatman filter paper. The macrocarrier holder containing the macrocarrier (BioRad 165-2335) was placed flatly on top of filter paper and the Petri dish lid replaced.

A tungsten particle suspension was prepared by adding 60 mg tungsten M-10 particles (microcarrier, 0.7 micron, Biorad #1652266) to an Eppendorf tube. One ml ethanol (100%) was added. The tungsten was vortexed in the ethanol solution and allowed to soak for 15 minutes. The Eppendorf tube was microfuged briefly at maximum speed to pellet the tungsten. The ethanol was decanted and washed three times with sterile distilled water. After the water wash was decanted the third time, the tungsten was resuspended in 1 ml of sterile 50% glycerol. The tungsten was prepared fresh every two weeks.

The transformation reaction was prepared by adding 25 μl of suspended tungsten to a 1.5 ml Eppendorf tube for each transformation. Subsequent additions were made in order, 0.5-5 μl DNA (0.2-1 μg/μl), 25 μl 2.5M $CaCl_2$, 10 μl 0.1 M spermidine. The reaction was vortexed continuously for 5-10 minutes, keeping the tungsten suspended. The Eppendorf tube was then microfuged briefly and decanted. The tungsten pellet was washed with 200 μl of 70% ethanol, microfuged briefly to pellet and decanted. The pellet was washed with 200 μl of 100% ethanol, microfuged briefly to pellet, and decanted. The tungsten pellet was resuspended, by pipetting, in 24 μl 100% ethanol. The Eppendorf tube was placed in an ultrasonic water bath for 15 seconds and 8 μl aliquots were transferred onto the center of the desiccated macrocarriers. The macrocarriers were left to dry in the desiccated Petri dishes.

A He tank was turned on to 1500 psi. 1100 psi rupture discs (BioRad 165-2329) were used in the Model PDS-1000/He Biolistic Particle Delivery System (BioRad). When the tungsten solution was dry, a stopping screen and the macrocarrier holder were inserted into the PDS-1000. An MABA plate, containing the target *T. reesei* spores, was placed 6 cm below the stopping screen. A vacuum of 29 inches Hg was pulled on the chamber and held. The He Biolistic Particle Delivery System was fired. The chamber was vented and the MABA plate removed for incubation, 28° C. for 5-7 days.

With reference to Example 2 the solutions were prepared as follows.

|  | per liter |
|---|---|
| Modified amdS Biolistic agar (MABA) Part I, make in 500 ml $dH_2O$ | |
| 1000x salts | 1 ml |
| Noble agar | 20 g |
| pH to 6.0, autoclave Part II, make in 500 ml $dH_2O$ | |
| Acetamide | 0.6 g |
| CsCl | 1.68 g |

-continued

|  | per liter |
| --- | --- |
| Glucose | 20 g |
| $KH_2PO_4$ | 15 g |
| $MgSO_4 \cdot 7H_2O$ | 0.6 g |
| $CaCl_2 \cdot 2H_2O$ | 0.6 g |
| pH to 4.5, 0.2 micron filter sterilize; leave in 50° C. oven to warm, add to Part I, mix, pour plates. | |
| 1000x Salts | |
| $FeSO_4 \cdot 7H_2O$ | 5 g |
| $MnSO_4 \cdot H_2O$ | 1.6 g |
| $ZnSO_4 \cdot 7H_2O$ | 1.4 g |
| $CoCl_2 \cdot 6H_2O$ | 1 g |
| 0.2 micron filter sterilize | |

Figure 10:
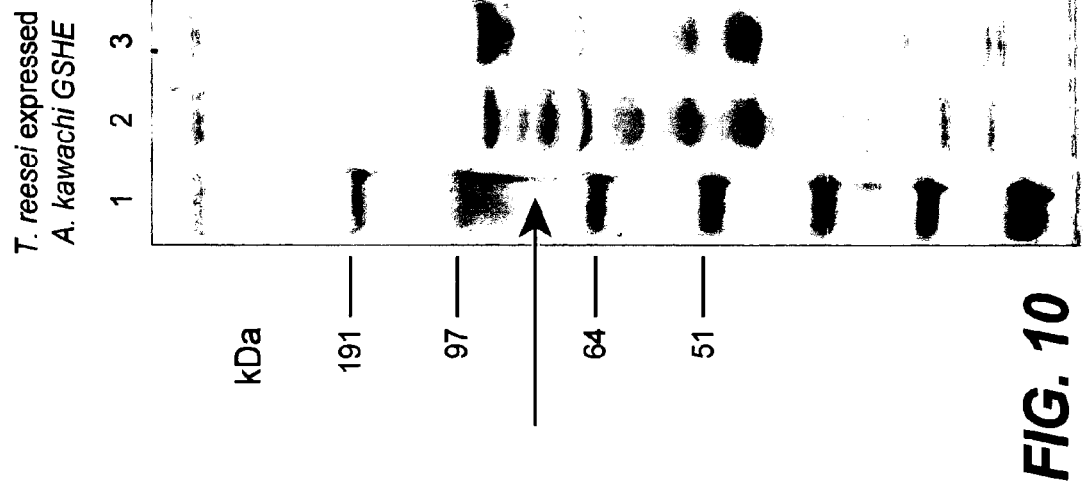
FIG. 10 provides an SDS-PAGE gel indicating the expression of *Aspergillus awamori* var. *kawachi* GSHE in a representative fermentation run for *Trichoderma reesei* clones as described in Example 2. Lane 1 represents the commercial molecular weight marker, SeeBlue (Invitrogen); lane 2 depicts rGSHE expression at 162 hours, and lane 3 is a control, which depicts the untransformed *Trichoderma reesei* host at 162 hours.

Expression of rGSHE (*A. awamori* var. *kawachi* GSHE expressed in *T. reesei*) was determined as described above for expression of *H. grisea* var. *thermoidea* in Example 1. The level of expression was determined to be greater than 1 g/L (data not shown). FIG. 10 provides the results of a SDS-PAGE gel illustrating the expression of *Aspergillus awamori* var. *kawachi* GSHE in the *T. reesei* host.

Example 3

Solubilization and Hydrolysis of Different Granular Starch Substrates by Alpha Amylase In a typical experiment, 150 grams of granular starch were suspended in 350 grams of distilled water. After mixing, the pH was adjusted to pH 5.5 using 6 N NaOH. The alpha amylase (GZYME G997 at 1.0 kg/MT of starch, ds) was added to the starch slurry and incubated with constant stirring in a water bath maintained at 60° C. The samples were withdrawn at different time intervals for measuring the Brix. The sample withdrawn at 24 hrs was used to determine the sugar composition using HPLC (Table 6).

TABLE 6

| G Zyme G 997 (0.1 kg/MT starch) | % Solids solublized Incubation time (hr) | | | | | | % Carbohydrate composition at 24 hr | | | |
| --- | --- | --- | --- | --- | --- | --- | --- | --- | --- | --- |
| Starch substrate | 2 | 4 | 6 | 9 | 12 | 24 | DPI | DP2 | DP3 | DP4+ |
| Corn | 32.2 | 39.3 | 42.9 | 49.2 | 52.8 | 53.9 | 0.6 | 12.0 | 15.0 | 72.4 |
| Tapioca | 46.6 | 50.8 | 53.6 | 56.1 | 58.2 | 62.4 | 1.6 | 11.6 | 14.6 | 72.2 |
| Wheat | 74.9 | 80.6 | 82.4 | 84.5 | 86.3 | 87.8 | 1.3 | 11.5 | 14.1 | 73.1 |

The results illustrated in Table 6 show significant differences in the solubilization of the granular starch substrates. Wheat had the highest % of solublized solids, and corn had the lowest percent. Significant differences were not observed in the sugar composition after 24 hours.

Example 4

Solubilization and Hydrolysis of Granular Starch Substrates by Alpha Amylase (G ZYME G 997) and rH-GSHE In a typical experiment, 350 g of water was added separately to 150 grams of each, granular cornstarch, granular wheat starch and granular tapioca starch and the pH was adjusted to pH 5.5 using 6N NaOH. The slurry was kept in a water bath, which was maintained at 60° C. with continuous stirring for uniform mixing. After stabilization of the temperature, alpha amylase as G Zyme G 997 (0.1 Kgs/MT of starch ds) and rH-GSHE (1.0 GSHE Units/gram of starch ds) were added to each starch slurry and incubation was continued. Samples were taken at different intervals of time, centrifuged and Brix was checked. The 24 hour samples were analyzed for sugar composition. The relative solubilization of the granular starch was calculated by comparing the Brix from the jet cooking process and reference is made to Table 7.

TABLE 7

| | % Relative Solubilization (hrs) | | | | | | % Soluble Sugar (24 hrs) | | | |
| --- | --- | --- | --- | --- | --- | --- | --- | --- | --- | --- |
| Starch | 2 | 4 | 6 | 12 | 18 | 24 | DP1 | DP2 | DP3 | DP4+ |
| Wheat | 86.0 | 91.0 | 93.9 | 95.7 | 97.5 | 98.2 | 97.3 | 2.3 | 0.2 | 0.2 |
| Corn | 61.3 | 78.4 | 87.9 | 98.2 | 100.0 | 100.0 | 97.4 | 2.1 | 0.2 | 0.2 |
| Tapioca | 64.9 | 75.4 | 81.8 | 87.4 | 91.6 | 97.5 | 96.5 | 1.6 | 0.4 | 1.5 |

The combined effect of G Zyme G 997 and rH-GSHE resulted in almost complete solubilization of the granular starch substrate under mild conditions compared to the current high temperature jet cooking process. The analysis of the 24-hour samples showed glucose yield greater than 96.5%.

Example 5

Solubilization and Hydrolysis of Granular Cornstarch by Glucoamylases Having Granular Starch Hydrolyzing Activity Commercially available glucoamylases exhibiting granular starch hydrolyzing activity from *Aspergillus niger* (OPTIDEX L-400 and G Zyme G 990 4X from Genencor International Inc), and *Rhizopus niveus* (CU. CONC. from Shin Nihon Chemicals, Japan) were compared with rH-GSHE as described above in example 1. The granular starch hydrolyzing activity of these products was measured using the assay described above.

TABLE 8

| Glucoamylase | GSHE units/g |
|---|---|
| OPTIDEX L-400 | 555 |
| G Zyme G 990 4X | 474 |
| CU.CONC. | 1542 |
| rH-GSHE | 518 |

In a typical experiment, a 30% granular cornstarch slurry in distilled water (150 grams of starch in 350 grams of distilled water) was prepared and the pH was adjusted to pH 5.5 using 6 N NaOH. G Zyme G 997 was added at 0.1 kg/MT of starch ds and the starch slurry was kept in a water bath maintained at 60° C. To each starch slurry containing G Zyme G 997, different glucoamylases were added at an equal dosage, i.e.; 1.5 GSHE units/gram starch, ds and incubated at 60° C. An aliquot was withdrawn at different time intervals and centrifuged. The clear supernatant was used for measuring the Brix. The sample incubated for 2, 6, 22.5 and 49 hours was analyzed by HPLC for total sugar composition and the results are shown in Table 9.

TABLE 9

| Enzyme | Hr | % DP1 | % DP2 | % DP3 | % DP4+ | % Solublized |
|---|---|---|---|---|---|---|
| Distillase L-400 | 2 | 94.2 | 0.9 | 0.2 | 4.7 | |
| G990 4X | 2 | 95.9 | 0.7 | 0.2 | 3.2 | |
| Cu Conc | 2 | 73.5 | 11.1 | 1.4 | 14.0 | |
| rH-GSHE | 2 | 96.4 | 1.1 | 0.1 | 2.3 | |
| Distillase L-400 | 6 | 96.1 | 1.2 | 0.2 | 2.5 | |
| G990 4X | 6 | 96.7 | 1.4 | 0.2 | 1.7 | |
| Cu Conc | 6 | 79.1 | 8.0 | 1.0 | 11.8 | |
| rH-GSHE | 6 | 97.9 | 1.4 | 0.0 | 0.7 | |
| Distillase L-400 | 22.5 | 96.8 | 2.1 | 0.2 | 0.9 | |
| G990 4X | 22.5 | 96.6 | 2.5 | 0.2 | 0.7 | |
| Cu Conc | 22.5 | 81.9 | 6.5 | 1.1 | 10.5 | |
| rH-GSHE | 22.5 | 96.2 | 3.4 | 0.2 | 0.1 | |
| Distillase L-400 | 49 | 96.3 | 3.0 | 0.2 | 0.5 | 81.6 |
| G990 4X | 49 | 96.0 | 3.3 | 0.2 | 0.4 | 81.6 |
| Cu Conc | 49 | 80.8 | 6.9 | 1.5 | 10.8 | 74.6 |
| rH-GSHE | 49 | 93.8 | 5.6 | 0.5 | 0.1 | 97.5 |

Glucoamylases were added at a dose of 1.5 GSHEU/g to a starting slurry having 0.1 kG/MT ds of alpha amylase.

Example 6

The Effect of pH on the Solubilization of Granular Cornstarch (35% Slurry) During Incubation with Alpha Amylase (G Zyme G 997) and rH-GSHE In a typical experiment, 372 grams of water was added to 178 grams of cornstarch. The slurry was stirred well for uniform mixing and the pH of the slurry was adjusted to pH 4.0, 5.0, 5.5, 6.0, 6.5 and 7.0 using 6 N NaOH. The samples were then kept in a water bath maintained at 60° C. After equilibration of the temperature, Zyme G997 at 0.1 kg/MT starch and rH-GSHE as described in example 1 (1.0 GSHE Units/g starch) were added to the slurry. The slurry was continuously stirred during incubation and samples were taken after one hour for measuring the brix (Table 10).

TABLE 10

| Incubation pH at 60° C. | % Maximum Solubilization |
|---|---|
| 4.0 | 9.9 |
| 5.0 | 100.0 |

TABLE 10-continued

| Incubation pH at 60° C. | % Maximum Solubilization |
|---|---|
| 5.5 | 100.0 |
| 6.0 | 95.0 |
| 6.5 | 92.0 |
| 7.0 | 76.7 |

The maximum solubilization occurred at pH 5.0 and pH 5.6. A significant reduction in the solubilization of the granular cornstarch occurred below pH 5.0 and pH 5.5 at 60° C. indicating either lower activity or inactivation of the enzymes.

Example 7

Effect of Temperature on the Solubilization of the Granular Cornstarch (32% Slurry) During Incubation with Alpha Amylase and rH-GSHE In a typical experiment, 372 grams of water was added to 178 grams of cornstarch. The slurry was stirred well for uniform mixing, and the pH of the slurry was adjusted to pH 5.5, using 6 N NaOH. The samples were kept in a water bath maintained at 55° C., 60° C. and 65° C. After equilibration of the temperature, Zyme G997 at 0.1 Kgs/MT starch and rH-GSHE as described in example 1 (1.0 GSHE Units/g starch) were added. The slurry was continuously stirred during incubation and the brix was measured after one hour. (Table 11).

TABLE 11

| Incubation Temperature ° C. | % Starch Solubilized |
|---|---|
| 55 | 28.7 |
| 60 | 51.4 |
| 65 | 59.6 |
| 70 | 75.1 |

The solubility of the granular cornstarch was increased with increasing temperature in the presence of G Zyme G997 and rH-GSHE. However HPLC analysis of the solublized carbohydrate above 65° C. indicated inactivation of rH-GSHE as evidenced by lower level of glucose content. The increase in the dissolved solids content at higher temperature (>65° C.) was mainly due to the liquefaction effect of G Zyme G997 on granular cornstarch at higher temperatures.

Example 8

Effect of G Zyme G997 and rH-GSHE Concentrations on the Solubilization and Hydrolysis of Granular Cornstarch In different flasks granular cornstarch (178 g) in 372 g water was stirred well for uniform mixing. The pH of the slurry was adjusted to pH 5.5. Two different levels of G Zyme G 997, 0.1 Kgs/MT starch and 0.5 Kgs/MT were incubated with rH-GSHE at 0.25. 0.5, and 1.0 GSHE units/g ds starch at 60° C. Samples were drawn at different intervals time, and used for measuring the brix and total sugar composition (Tables 12A and 12B).

TABLE 12A

Enzyme Concentration

| G Zyme G997 Kgs/MT starch | rH-GSHE GSHE Units/g starch | % Relative Solubilization | | | | | |
|---|---|---|---|---|---|---|---|
| | | 3 hr | 6 hr | 9 hr | 12 hr | 24 hr | 30 hr |
| 0.1 | 0.25 | 50.9 | 59.3 | 70.2 | 75.1 | 85.8 | 88.6 |
| 0.1 | 0.50 | 54.3 | 72.9 | 80.4 | 85.2 | 94.0 | 96.8 |
| 0.1 | 1.0 | 60.7 | 80.4 | 88.6 | 92.1 | 98.1 | 100 |
| 0.5 | 0.25 | 60.9 | 71.9 | 77.6 | 83.3 | 91.2 | 94.0 |
| 0.5 | 0.5 | 66.9 | 79.5 | 85.8 | 89.9 | 97.2 | 99.4 |
| 0.5 | 1.0 | 76.7 | 87.4 | 92.4 | 95.3 | 99.1 | 99.7 |

The results in Table 12A indicate that increasing the dosage of G Zyme G 997 from 0.1 Kgs/MT of starch to 0.5 Kg/MT of starch resulted in a faster solubilization of granular starch. But at both levels greater than 95% solubilization of granular starch occurred in 24 hours in presence of 1.0 GSHE units of rH-GSHE. The effect of rH-GSHE concentration on the solubilization of granular starch in the presence of G Zyme G 997 increased dramatically with increasing dosage of concentration. The above results clearly show that neither of the enzymes, G Zyme G 997 or rH-GSHE alone can solubilize the granular starch to completion. However, complete solubilization of the granular starch occurred when the enzymes were added together.

The carbohydrate (sugar) composition of the solublized granular (32% slurry) cornstarch during incubation of the granular cornstarch with G ZYME G997 and rH-GSHE at 12, 24 and 30 hour at pH 5.5 and 60° C. was analyzed by HPLC and reference is made to Table 12B.

TABLE 12B

Enzyme composition

| G Zyme G997 kg/MT st | rH-GSHE GSHE U/g st | Incubation Time (hr) | % starch solubilized | % Carbohydrate Composition | | | |
|---|---|---|---|---|---|---|---|
| | | | | DP1 | DP2 | DP3 | DP4+ |
| 0.1 | 0.25 | 12 | 75.1 | 87.9 | 4.1 | 0.9 | 7.2 |
| | | 24 | 85.8 | 93.2 | 2.4 | 0.8 | 3.6 |
| | | 30 | 88.6 | 94.7 | 2.0 | 0.8 | 2.6 |
| 0.1 | 0.50 | 12 | 85.2 | 95.9 | 1.6 | 0.4 | 2.1 |
| | | 24 | 94.0 | 97.0 | 1.8 | 0.3 | 0.9 |
| | | 30 | 96.8 | 97.5 | 2.0 | 0.2 | 0.4 |
| 0.1 | 1.00 | 12 | 92.1 | 97.5 | 1.9 | 0.2 | 0.5 |
| | | 24 | 98.1 | 96.9 | 2.8 | 0.2 | 0.2 |
| | | 30 | 100.0 | 96.3 | 3.3 | 0.3 | 0.2 |
| 0.5 | 0.25 | 12 | 83.3 | 84.4 | 6.4 | 1.4 | 7.8 |
| | | 24 | 91.2 | 92.0 | 3.0 | 1.3 | 3.6 |
| | | 30 | 94.0 | 94.0 | 2.3 | 1.1 | 2.6 |
| 0.5 | 0.50 | 12 | 98.9 | 95.0 | 2.0 | 0.9 | 2.4 |
| | | 24 | 97.2 | 96.6 | 1.9 | 0.5 | 0.9 |
| | | 30 | 99.4 | 96.9 | 2.1 | 0.4 | 0.6 |
| 0.5 | 1.00 | 12 | 95.3 | 97.1 | 1.9 | 0.3 | 0.7 |
| | | 24 | 99.1 | 96.7 | 2.3 | 0.3 | 0.2 |
| | | 30 | 99.7 | 96.4 | 3.2 | 0.3 | 0.2 |

The results in Table 12B illustrate that an appropriate blend of *Bacillus stearothermophilus* alpha amylase and rH-GSHE would meet a variety of demands in the commercial production of sugar sweeteners and biochemicals directly from granular starch without applying conventional high temperature cooking process. High levels of alpha amylase accelerates the rate of solubilization of granular starch but higher level of rH-GSHE resulted in high levels of reversion reaction products resulting in significantly low levels of higher sugar.

Example 9

Comparison on the Hydrolysis of Enzyme Liquefied Cornstarch Substrate (Soluble Starch Substrate) and Granular Cornstarch Substrate (Insoluble) by Glucoamylase Preparations In a typical experiment, cornstarch (32% ds) was liquefied at pH 5.6 using the low temperature jet cooking process (105° C., 8 min) followed by hydrolysis at 95° C. for 90 min. SPEZYME FRED (Genencor International Inc) was added at 0.4 Kgs/MT of starch, ds. in the liquefaction process. The pH of the SPEZYME FRED liquefied starch substrate was adjusted to pH 4.2 and glucoamylase (OPTIDEX L-400) was added at 0.22 GAU/g ds. The hydrolysis was carried out at 60° C. Samples were withdrawn at different time intervals and analyzed by HPLC to determine the time required for reaching the maximum glucose yield.

Thirty two percent ds granular cornstarch slurry in distilled water was prepared and the pH of the slurry was adjusted to pH 5.5 using 1 N NaOH. The flask was then kept in a water bath maintained at 60° C. and G Zyme G997 was added at 0.1 Kgs/MT ds and rH-GSHE was added at 1.0 GSHE Units/gram ds and the sample was incubated at 60° C. with constant stirring. Samples were withdrawn at different intervals of time for measuring the BRIX and glucose yield (Table 13).

TABLE 13

| Substrate | Glucoamylase | Time (hr) for reaching Max. glucose | Composition at Maximum. Glucose yield (%) | | | |
|---|---|---|---|---|---|---|
| | | | DP1 | DP2 | DP3 | DP4+ |
| Liquefied Starch Soluble, 32% slurry | OPTIDEX L-400 | 61 | 95.2 | 3.1 | 0.4 | 1.3 |
| Granular Starch Insoluble, 32% slurry | rH-GSHE and G ZYME G997 | 24 | 96.8 | 2.8 | 0.2 | 0.2 |

Hydrolysis of the liquefied soluble starch by glucoamylase required a longer time to achieve the maximum glucose yield compared to the hydrolysis of insoluble granular starch. At the peak time for reaching maximum glucose yield, the glucose level by granular starch as compared to liquefied soluble starch was higher with significantly lower sugars at DP4+ (96.8 and 0.2 compared with 95.2 and 1.3).

Higher glucose yield, the potential for shorter saccharification time and a total elimination of high temperature jet cooking step, differentiates the application of the alpha amylase and GSHE enzyme blend of the present invention.

Example 10

Effect of Granular Cornstarch Concentration on the Solubilization and Hydrolysis of Starch During the Incubation with G Zyme G 997 (0.1 Kgs/MT) and rH-GSHE (1.0 GSHE Units/g)

Different concentrations of granular cornstarch slurry were prepared in distilled water. i.e., 32%, 35%, 38%, 40% and 42%. The pH of the slurry was adjusted to pH 5.5. The samples were then kept in a water bath maintained at 60° C. and stirred continuously for uniform mixing. G Zyme G997 (0.1 Kgs/MT of ds) and rH-GSHE obtained from Example 1 (1.0 GSHE units/g ds) were added to the slurry. An aliquot sample was withdrawn at different time intervals during incubation for measuring brix and sugar composition (Table 14).

TABLE 14

| Trial | Starting % DS | Sample % DS | Hours | % Cabohydrate Profile | | | |
|---|---|---|---|---|---|---|---|
| | | | | DP > 3 | DP3 | DP2 | DP1 |
| 1 | 32 | 0.41 | 0 | | | | |
| 1 | 32 | 21.31 | 2.5 | | | | |
| 1 | 32 | 26.84 | 7 | 1.56 | 0.35 | 1.71 | 96.38 |
| 1 | 32 | 33.55 | 24 | 0.28 | 0.39 | 3.30 | 96.03 |
| 1 | 32 | 34.50 | 48 | 0.49 | 0.40 | 3.83 | 95.28 |
| 2 | 35 | 0.49 | 0 | | | | |
| 2 | 35 | 22.57 | 2.5 | | | | |
| 2 | 35 | 28.57 | 7 | 1.24 | 0.35 | 1.81 | 96.60 |
| 2 | 35 | 34.50 | 24 | 0.33 | 0.71 | 4.16 | 94.80 |
| 2 | 35 | 36.91 | 48 | 0.21 | 0.68 | 4.71 | 94.40 |
| 3 | 38 | 0.62 | 0 | | | | |
| 3 | 38 | 23.89 | 2.5 | | | | |
| 3 | 38 | 29.67 | 7 | 1.38 | 0.33 | 1.84 | 96.45 |
| 3 | 38 | 35.76 | 24 | 0.31 | 0.38 | 3.21 | 96.11 |
| 3 | 38 | 38.64 | 48 | 0.48 | 0.56 | 4.76 | 94.19 |
| 4 | 40 | 0.34 | 0 | | | | |
| 4 | 40 | 27.78 | 2.5 | | | | |
| 4 | 40 | 30.47 | 7 | 1.36 | 0.35 | 1.94 | 96.35 |
| 4 | 40 | 36.58 | 24 | 0.38 | 0.50 | 2.79 | 96.33 |
| 4 | 40 | 39.71 | 48 | 0.22 | 0.70 | 4.77 | 94.31 |
| 5 | 42 | 0.48 | 0 | | | | |
| 5 | 42 | 25.31 | 2.5 | | | | |
| 5 | 42 | 31.64 | 7 | 1.23 | 0.34 | 2.00 | 96.43 |
| 5 | 42 | 37.94 | 24 | 0.63 | 0.35 | 3.09 | 95.93 |
| 5 | 42 | 40.82 | 48 | 0.40 | 1.29 | 6.57 | 91.74 |

The results show over 96% glucose syrup could be reached within 24 hours of the saccharification at dissolved solids as high as 36%. The glucose yield of greater than 96% at a solid level higher than 35% was reached when an insoluble granular starch was used in the saccharification process.

Example 11

As taught above and known in the art, the enzyme-enzyme starch conversion process for high glucose syrup consists of producing a soluble liquefact by subjecting an insoluble starch substrate to a high temperature liquefaction process using a thermostable alpha amylase. It is the normal practice in the commerce to inactivate the residual alpha amylase activity prior to the saccharification by glucoamylase to reduce the loss of glucose yield due to the presence of active alpha amylase. The inactivation of the residual alpha amylase activity is normally carried out by decreasing the liquefact to pH 4.2 at 95° C. High temperature and pH 4.5 result in the complete inactivation of the alpha amylase. So we studied the effect of glucose yield with and without active alpha amylase during saccharification of liquefact starch at pH 5.5.

In a typical experiment, soluble liquefact from cornstarch was produced using G Zyme G 997 (0.4 Kgs/MT starch) as a liquefying enzyme under jet cooking process conditions (32% ds starch at 105° C. at 8 min followed by 95° C. for 90 min). A portion of the liquefied starch was further heated to inactivate the residual alpha amylase activity. The saccharification of the liquefied starch with and without residual alpha amylase activity was further saccharified (32% ds) at pH 5.5, 60° C. using rH-GSHE as described in example 1 at 0.5 GSHE units/g. Samples were withdrawn at different intervals of time and analyzed for glucose yield using HPLC (Table 15).

TABLE 15

| Alpha Amylase Activity During Saccharification | Substrate | Sac. Time (Hrs) | % Sugar Composition | | | |
|---|---|---|---|---|---|---|
| | | | DP1 | DP2 | DP3 | DP4+ |
| Inactive | Soluble Liquefact | 18 | 91.48 | 1.85 | 0.41 | 6.25 |
| | | 24 | 94.37 | 1.88 | 0.33 | 3.43 |
| | | 42 | 96.08 | 2.74 | 0.32 | 0.86 |
| | | 48 | 96.01 | 2.95 | 0.30 | 0.74 |
| | | 68 | 95.25 | 3.79 | 0.44 | 0.52 |
| Active | Soluble Liquefact | 18 | 91.88 | 2.54 | 1.19 | 4.39 |
| | | 24 | 94.31 | 2.20 | 1.00 | 2.49 |
| | | 42 | 95.78 | 2.84 | 0.62 | 0.77 |
| | | 48 | 95.85 | 3.03 | 0.53 | 0.59 |
| | | 68 | 95.33 | 3.85 | 0.57 | 0.24 |
| Active | Insoluble starch | 24 | 96.84 | 2.75 | 0.23 | 0.18 |

The results in Table 15 demonstrate that the presence of alpha amylase activity of G Zyme G 997 during the saccharification of the soluble starch substrate (liquefact) by glucoamylase resulted in the lower glucose yield. Whereas, alpha amylase enhances the hydrolysis of insoluble (granular) starch substrate by glucoamylase resulting in a substantially high level of glucose.

Example 12

Production of Glucose Syrup and Residual Starch from Hydrolysis of Corn Starch

In a reactor vessel, granular cornstarch (800 g) in 1200 g water was stirred well for uniform mixing to obtain a slurry. The pH of the slurry was adjusted to pH 5.5 with 4 N NaOH. G ZYME G 997 (0.1 Kgs/MT starch) and *Humicola grisea* var. *theromidea* expressed in *Trichoderma reesei* (rH-GSHE) at 1.0 GSHE U/g starch were added at 60° C. Samples were withdrawn at various time intervals and used for measuring the brix and total sugar composition (Table 16).

TABLE 16

| | Reaction Time | | |
|---|---|---|---|
| | 3 hr | 6 hr | 9 hr |
| % Solublization | 60.7 | 80.4 | 88.6 |

After achieving greater that 90% solubilization of granular starch in a 10 hour reaction time, the sugar composition, measured by HPLC, of the solublized granular cornstarch was achieved as illustrated in Table 17.

TABLE 17

| | Sugar Type | | | |
|---|---|---|---|---|
| | DP1 | DP2 | DP3 | DP 4+ |
| % Composition | 97.5 | 1.9 | 0.2 | 0.5 |

After a 10 hr reaction time, the hydrolysis was stopped by adjusting the pH to 3.5 with 4N $H_2SO_4$. The syrup mixture contained greater than 96% dextrose at greater than 30% dissolved solids. The mixture was filtered at 60° C. by using a 500,000 molecular weight cut-off (MWCO) ultrafiltration membrane cartridge (AG Technology, MA). The residual starch could then be recycled which would significantly reduced capital and operating costs incurred in the production of glucose syrup.

A sample of the residual starch was dried and examined for its structure by scanning electron microscope (Hitachi S-5000 cold field emission SEM (Tokyo, Japan)) and compared with a typical starch granular before expose to enzymes in accordance with the method of the invention (FIG. 12). The dried samples were mounted on SEM sample stubs using double-sided adhesive carbon tape. Any excess sample was removed by dusting with compressed air. The samples were then mounted at about a 30° angle in a Bal-Tec Med 020 Modular High Vacuum Coating System (Liechtenstein) and sputter coated with 10 nn of platinum (Pt) while rotating at 60 rpm. These settings ensured that the granules were evenly coated on all sides. The thickness of the coating is negligible compared to the size of the features resulting from the enzymatic action of the starch granules. The accelerating voltage varied from 2-5 kV and magnification was between 500-15,000×.

Figure 12A:
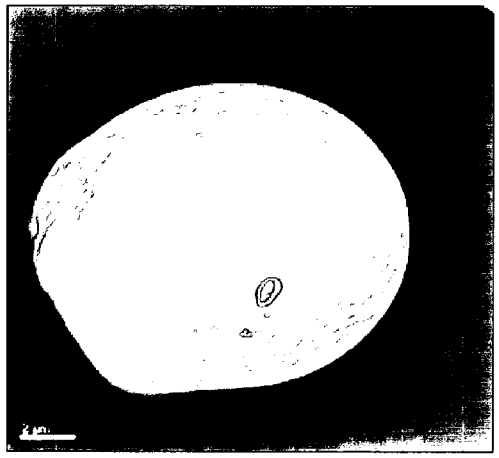
FIG. 12A shows a corn starch granule before exposure to a process of the invention.
Figure 12B:
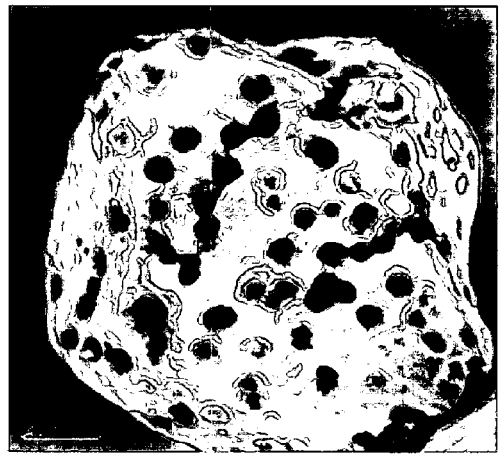
FIG. 12B, FIG. 12C, and FIG. 12D show scanning electron micrographs of residual starch after exposure to the process encompassed by the invention.
Figure 12C:
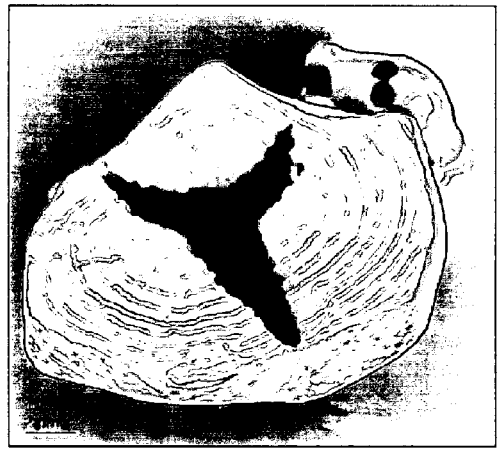
Figure 12D:

Micrograph FIG. 12a depicts a typical starch granule before exposure to an enzyme composition and method of the invention. The surface is smooth and homogenous and the only noticeable feature is a fine cracking due to the platinum metal coating. Once exposed to the enzyme blend and method of the invention, the surface morphology of the granules change. As seen in micrographs b-d of FIG. 12, large round holes are bored into the granules due to enzyme digestion of the starch granule substrate. The holes range in diameter and vary in depth, and reflect a population of starch granules at different kinetic stages of enzymatic reaction. Some granules have only a few number of holes and some are nearly covered in holes (micrograph b). Some granules were also sliced in half revealing a cross section of digested interior (micrographs c and d). Micrograph d) reveals granule digestion to completion, showing a fragment of a hollowed out shell.

The invention claimed is:

1. A process for producing residual starch from a granular starch slurry, said process comprising:
    contacting a granular starch slurry obtained from a granular starch substrate simultaneously with an alpha amylase and a glucoamylase, wherein the glucoamylase has at least 97% amino acid sequence identity with SEQ ID NO: 3, at a temperature equal to or below the gelatinization temperature of the granular starch;
    allowing the alpha amylase and the glucoamylase to act for a period of time sufficient to hydrolyze the granular starch to obtain glucose and residual starch; and,
    retaining the residual starch to produce residual starch from the granular starch slurry.

2. The method of claim 1 wherein the residual starch is used for the production of end products selected from the group consisting of fructose syrup, L-amino acids and ethanol.

3. The method of claim 1 wherein the residual starch is recycled and contacted with the alpha amylase and glucoamylase at the temperature equal to or below the gelatinization temperature of the granular starch.

* * * * *

SEQUENCE LISTING

<160> NUMBER OF SEQ ID NOS: 11

<210> SEQ ID NO 1
<211> LENGTH: 2103
<212> TYPE: DNA
<213> ORGANISM: Humicola grisea var. thermoidea

<400> SEQUENCE: 1

```
atgcatacct tctccaagct cctcgtcctg ggctctgccg tccagtctgc cctcgggcgg      60
cctcacggct cttcgcgtct ccaggaacgc gctgccgttg ataccttcat caacaccgag     120
aagcccatcg catggaacaa gctgctcgcc aacatcggcc ctaacggcaa agccgctccc     180
ggtgccgccg ccggcgttgt gattgccagc ccttccagga cggaccctcc ttgtacgtgg     240
tggcatggaa tggacccaag agactggttt tagatgaaag agagtttctg ctaaccgcca     300
cacccagact tcttcacctg gacccgcgat gccgccctgg tcctcaccgg catcatcgag     360
tcccttggcc acaactacaa caccaccctg cagaccgtca tccagaacta cgtcgcgtcg     420
caggccaagc tgcagcaggt ctcgaacccc tcgggaacct tcgccgacgg ctcgggtctc     480
ggtgaggcca agttcaatgt cgacctcact gccttcactg gcgaatgggg tcgccctcag     540
agggacggcc cgcccctgcg cgccatcgct ctcatccagt acgccaagtg gctgatcgcc     600
aacggctaca agagcacggc caagagcgtc gtctggcccg tcgtcaagaa cgatctcgcc     660
tacacggccc agtactggaa cgagaccggc ttcgatctct gggaggaggt ccccggcagc     720 tcgttctttta ccatcgccag ctctcacagg ggtgagtcat ttattgttca gtgttttctc     780
attgaataat taccggaatg ccactgacgc caaacagctc tgactgaggg tgcttacctc     840
gccgctcagc tcgacaccga gtgccgcgcc tgcacgaccg tcgccctca ggttctgtgc     900
```

-continued

```
ttccagcagg ccttctggaa ctccaagggc aactatgtcg tctccaacag taagatccct    960
acaccaacaa aaaaaatcga aaggaacgt tagctgaccc ttctagtcaa cggcggcgag   1020
tatcgctccg gcaaggacgc caactcgatc ctggcgtcca tccacaactt cgaccctgag   1080
gccggctgcg acaacctgac cttccagccc tgcagcgagc gcgccctggc caaccacaag   1140
gcctatgtcg actcgttccg caacctctac gccatcaaca agggcatcgc ccagggcaag   1200
gccgttgccg tcggccgcta ctcggaggat gtctactaca cggcaaccc gtggtacctg   1260
gccaactttg ccgccgccga gcagctctac gacgccatct acgtgtggaa caagcagggc   1320
tccatcaccg tgacctcggt ctccctgccc ttcttccgcg accttgtctc gtcggtcagc   1380
accggcacct actccaagag cagctcgacc ttcaccaaca tcgtcaacgc cgtcaaggcc   1440
tacgccgacg gcttcatcga ggtggcggcc aagtacaccc cgtccaacgg cgcgctcgcc   1500
gagcagtacg accgcaacac gggcaagccc gactcggccg ccgacctgac gtggtcgtac   1560
tcggccttcc tctcggccat cgaccgccgc gcgggtctcg tccccccgag ctggcgggcc   1620
agcgtggcca agagccagct gccgtccacc tgctcgcgca tcgaggtcgc cggcacctac   1680
gtcgccgcca cgagcacctc gttcccgtcc aagcagaccc cgaacccctc gcggcgcccc   1740
tccccgtccc cctacccgac cgcctgcgcg gacgctagcg aggtgtacgt caccttcaac   1800
gagcgcgtgt cgaccgcgtg gggcgagacc atcaaggtgg tgggcaacgt gccggcgctg   1860
gggaactggg acacgtccaa ggcggtgacc ctgtcggcca gcgggtacaa gtcgaatgat   1920
cccctctgga gcatcacggt gcccatcaag gcgacgggct cggccgtgca gtacaagtat   1980
atcaaggtcg gcaccaacgg gaagattact tgggagtcgg accccaacag gagcattacc   2040
ctgcagacgg cgtcgtctgc gggcaagtgc gccgcgcaga cggtgaatga ttcgtggcgt   2100
taa                                                                2103
```

<210> SEQ ID NO 2
<211> LENGTH: 634
<212> TYPE: PRT
<213> ORGANISM: Humicola grisea var. thermoidea

<400> SEQUENCE: 2

```
Met His Thr Phe Ser Lys Leu Leu Val Leu Gly Ser Ala Val Gln Ser
  1               5                  10                  15

Ala Leu Gly Arg Pro His Gly Ser Ser Arg Leu Gln Glu Arg Ala Ala
                 20                  25                  30

Val Asp Thr Phe Ile Asn Thr Glu Lys Pro Ile Ala Trp Asn Lys Leu
             35                  40                  45

Leu Ala Asn Ile Gly Pro Asn Gly Lys Ala Ala Pro Gly Ala Ala Ala
         50                  55                  60

Gly Val Val Ile Ala Ser Pro Ser Arg Thr Asp Pro Pro Tyr Phe Phe
 65                  70                  75                  80

Thr Trp Thr Arg Asp Ala Ala Leu Val Leu Thr Gly Ile Ile Glu Ser
                 85                  90                  95

Leu Gly His Asn Tyr Asn Thr Thr Leu Gln Thr Val Ile Gln Asn Tyr
                100                 105                 110

Val Ala Ser Gln Ala Lys Leu Gln Gln Val Ser Asn Pro Ser Gly Thr
            115                 120                 125

Phe Ala Asp Gly Ser Gly Leu Gly Glu Ala Lys Phe Asn Val Asp Leu
        130                 135                 140

Thr Ala Phe Thr Gly Glu Trp Gly Arg Pro Gln Arg Asp Gly Pro Pro
```

```
145                 150                 155                 160
Leu Arg Ala Ile Ala Leu Ile Gln Tyr Ala Lys Trp Leu Ile Ala Asn
                165                 170                 175
Gly Tyr Lys Ser Thr Ala Lys Ser Val Val Trp Pro Val Val Lys Asn
                180                 185                 190
Asp Leu Ala Tyr Thr Ala Gln Tyr Trp Asn Glu Thr Gly Phe Asp Leu
                195                 200                 205
Trp Glu Glu Val Pro Gly Ser Ser Phe Phe Thr Ile Ala Ser Ser His
    210                 215                 220
Arg Ala Leu Thr Glu Gly Ala Tyr Leu Ala Ala Gln Leu Asp Thr Glu
225                 230                 235                 240
Cys Arg Ala Cys Thr Thr Val Ala Pro Gln Val Leu Cys Phe Gln Gln
                245                 250                 255
Ala Phe Trp Asn Ser Lys Gly Asn Tyr Val Val Ser Asn Ile Asn Gly
                260                 265                 270
Gly Glu Tyr Arg Ser Gly Lys Asp Ala Asn Ser Ile Leu Ala Ser Ile
                275                 280                 285
His Asn Phe Asp Pro Glu Ala Gly Cys Asp Asn Leu Thr Phe Gln Pro
    290                 295                 300
Cys Ser Glu Arg Ala Leu Ala Asn His Lys Ala Tyr Val Asp Ser Phe
305                 310                 315                 320
Arg Asn Leu Tyr Ala Ile Asn Lys Gly Ile Ala Gln Gly Lys Ala Val
                325                 330                 335
Ala Val Gly Arg Tyr Ser Glu Asp Val Tyr Tyr Asn Gly Asn Pro Trp
                340                 345                 350
Tyr Leu Ala Asn Phe Ala Ala Ala Glu Gln Leu Tyr Asp Ala Ile Tyr
                355                 360                 365
Val Trp Asn Lys Gln Gly Ser Ile Thr Val Thr Ser Val Ser Leu Pro
                370                 375                 380
Phe Phe Arg Asp Leu Val Ser Ser Val Ser Thr Gly Thr Tyr Ser Lys
385                 390                 395                 400
Ser Ser Ser Thr Phe Thr Asn Ile Val Asn Ala Val Lys Ala Tyr Ala
                405                 410                 415
Asp Gly Phe Ile Glu Val Ala Ala Lys Tyr Thr Pro Ser Asn Gly Ala
                420                 425                 430
Leu Ala Glu Gln Tyr Asp Arg Asn Thr Gly Lys Pro Asp Ser Ala Ala
                435                 440                 445
Asp Leu Thr Trp Ser Tyr Ser Ala Phe Leu Ser Ala Ile Asp Arg Arg
    450                 455                 460
Ala Gly Leu Val Pro Pro Ser Trp Arg Ala Ser Val Ala Lys Ser Gln
465                 470                 475                 480
Leu Pro Ser Thr Cys Ser Arg Ile Glu Val Ala Gly Thr Tyr Val Ala
                485                 490                 495
Ala Thr Ser Thr Ser Phe Pro Ser Lys Gln Thr Pro Asn Pro Ser Ala
                500                 505                 510
Ala Pro Ser Pro Ser Pro Tyr Pro Thr Ala Cys Ala Asp Ala Ser Glu
    515                 520                 525
Val Tyr Val Thr Phe Asn Glu Arg Val Ser Thr Ala Trp Gly Glu Thr
    530                 535                 540
Ile Lys Val Val Gly Asn Val Pro Ala Leu Gly Asn Trp Asp Thr Ser
545                 550                 555                 560
Lys Ala Val Thr Leu Ser Ala Ser Gly Tyr Lys Ser Asn Asp Pro Leu
                565                 570                 575
```

```
Trp Ser Ile Thr Val Pro Ile Lys Ala Thr Gly Ser Ala Val Gln Tyr
            580                 585                 590

Lys Tyr Ile Lys Val Gly Thr Asn Gly Lys Ile Thr Trp Glu Ser Asp
        595                 600                 605

Pro Asn Arg Ser Ile Thr Leu Gln Thr Ala Ser Ser Ala Gly Lys Cys
610                 615                 620

Ala Ala Gln Thr Val Asn Asp Ser Trp Arg
625                 630

<210> SEQ ID NO 3
<211> LENGTH: 604
<212> TYPE: PRT
<213> ORGANISM: Humicola grisea var. thermoidea

<400> SEQUENCE: 3

Ala Ala Val Asp Thr Phe Ile Asn Thr Glu Lys Pro Ile Ala Trp Asn
1               5                   10                  15

Lys Leu Leu Ala Asn Ile Gly Pro Asn Gly Lys Ala Ala Pro Gly Ala
            20                  25                  30

Ala Ala Gly Val Val Ile Ala Ser Pro Ser Arg Thr Asp Pro Pro Tyr
        35                  40                  45

Phe Phe Thr Trp Thr Arg Asp Ala Ala Leu Val Leu Thr Gly Ile Ile
    50                  55                  60

Glu Ser Leu Gly His Asn Tyr Asn Thr Thr Leu Gln Thr Val Ile Gln
65                  70                  75                  80

Asn Tyr Val Ala Ser Gln Ala Lys Leu Gln Gln Val Ser Asn Pro Ser
                85                  90                  95

Gly Thr Phe Ala Asp Gly Ser Gly Leu Gly Glu Ala Lys Phe Asn Val
            100                 105                 110

Asp Leu Thr Ala Phe Thr Gly Glu Trp Gly Arg Pro Gln Arg Asp Gly
        115                 120                 125

Pro Pro Leu Arg Ala Ile Ala Leu Ile Gln Tyr Ala Lys Trp Leu Ile
    130                 135                 140

Ala Asn Gly Tyr Lys Ser Thr Ala Lys Ser Val Val Trp Pro Val Val
145                 150                 155                 160

Lys Asn Asp Leu Ala Tyr Thr Ala Gln Tyr Trp Asn Glu Thr Gly Phe
                165                 170                 175

Asp Leu Trp Glu Glu Val Pro Gly Ser Ser Phe Phe Thr Ile Ala Ser
            180                 185                 190

Ser His Arg Ala Leu Thr Glu Gly Ala Tyr Leu Ala Ala Gln Leu Asp
        195                 200                 205

Thr Glu Cys Arg Ala Cys Thr Thr Val Ala Pro Gln Val Leu Cys Phe
    210                 215                 220

Gln Gln Ala Phe Trp Asn Ser Lys Gly Asn Tyr Val Val Ser Asn Ile
225                 230                 235                 240

Asn Gly Gly Glu Tyr Arg Ser Gly Lys Asp Ala Asn Ser Ile Leu Ala
                245                 250                 255

Ser Ile His Asn Phe Asp Pro Glu Ala Gly Cys Asp Asn Leu Thr Phe
            260                 265                 270

Gln Pro Cys Ser Glu Arg Ala Leu Ala Asn His Lys Ala Tyr Val Asp
        275                 280                 285

Ser Phe Arg Asn Leu Tyr Ala Ile Asn Lys Gly Ile Ala Gln Gly Lys
    290                 295                 300

Ala Val Ala Val Gly Arg Tyr Ser Glu Asp Val Tyr Tyr Asn Gly Asn
```

```
              305                 310                 315                 320
            Pro Trp Tyr Leu Ala Asn Phe Ala Ala Ala Glu Gln Leu Tyr Asp Ala
                            325                 330                 335

Ile Tyr Val Trp Asn Lys Gln Gly Ser Ile Thr Val Thr Ser Val Ser
                            340                 345                 350

Leu Pro Phe Phe Arg Asp Leu Val Ser Ser Val Ser Thr Gly Thr Tyr
                            355                 360                 365

Ser Lys Ser Ser Ser Thr Phe Thr Asn Ile Val Asn Ala Val Lys Ala
                    370                 375                 380

Tyr Ala Asp Gly Phe Ile Glu Val Ala Ala Lys Tyr Thr Pro Ser Asn
            385                 390                 395                 400

Gly Ala Leu Ala Glu Gln Tyr Asp Arg Asn Thr Gly Lys Pro Asp Ser
                            405                 410                 415

Ala Ala Asp Leu Thr Trp Ser Tyr Ser Ala Phe Leu Ser Ala Ile Asp
                            420                 425                 430

Arg Arg Ala Gly Leu Val Pro Pro Ser Trp Arg Ala Ser Val Ala Lys
                            435                 440                 445

Ser Gln Leu Pro Ser Thr Cys Ser Arg Ile Glu Val Ala Gly Thr Tyr
                    450                 455                 460

Val Ala Ala Thr Ser Thr Ser Phe Pro Ser Lys Gln Thr Pro Asn Pro
            465                 470                 475                 480

Ser Ala Ala Pro Ser Pro Ser Pro Tyr Pro Thr Ala Cys Ala Asp Ala
                            485                 490                 495

Ser Glu Val Tyr Val Thr Phe Asn Glu Arg Val Ser Thr Ala Trp Gly
                            500                 505                 510

Glu Thr Ile Lys Val Val Gly Asn Val Pro Ala Leu Gly Asn Trp Asp
                            515                 520                 525

Thr Ser Lys Ala Val Thr Leu Ser Ala Ser Gly Tyr Lys Ser Asn Asp
                    530                 535                 540

Pro Leu Trp Ser Ile Thr Val Pro Ile Lys Ala Thr Gly Ser Ala Val
            545                 550                 555                 560

Gln Tyr Lys Tyr Ile Lys Val Gly Thr Asn Gly Lys Ile Thr Trp Glu
                            565                 570                 575

Ser Asp Pro Asn Arg Ser Ile Thr Leu Gln Thr Ala Ser Ser Ala Gly
                            580                 585                 590

Lys Cys Ala Ala Gln Thr Val Asn Asp Ser Trp Arg
                    595                 600

<210> SEQ ID NO 4
<211> LENGTH: 2169
<212> TYPE: DNA
<213> ORGANISM: Aspergillus awamori var. kawachi

<400> SEQUENCE: 4
atgtcgttcc gatctcttct cgccctgagc ggccttgtct gctcggggtt ggcaagtgtg      60
atttccaagc gcgcgacctt ggattcgtgg ttgagcaacg aagcgaccgt ggcccgtact     120
gcgatcctga ataacatcgg gcggacggt gcttgggtgt cgggcgcgga ctctggcatt      180
gtcgttgcca gtcccagcac cgataacccg gactgtatgt tttgagttcg gattatgaat     240
gtgtcttggt tgattgatgc tgactggcgt gtcttttgat gattgtagac ttctacacct     300
ggactcgcga ctctggtctc gtcatcaaga ccctcgtcga cctcttccgc aatggagata     360
ctgatctcct ttccaccatt gagcactaca tctcctctca ggcaattatt cagggtgtca     420
gtaacccctc tggtgatctg tccagcggtg gtcttggtga gcccaagttc aatgtcgatg     480
```

```
agactgccta caccggttct tggggacggc cgcagcgtga tggtcctgcc ctgagagcaa    540
ctgctatgat cggctttggg cagtggctgc ttgtatgttc tccacctcct gcgtctgat     600
ctgcaacata tgtagccgac tggtcaggac aatggctaca ccagcgctgc aacagagatt    660
gtttggcccc tcgttaggaa cgacctgtcg tatgtggctc agtactggaa ccagacggga    720
tatggtgtgt ttgattgatc ggggttcaag ggtgtttgtg catcggagct aacttcgcgg    780
tcgcagatct ctgggaagaa gttaatggct cgtccttctt cactattgcc gtgcaacacc    840
gcgccctcgt cgaaggtagt gccttcgcga cggccgtcgg ctcgtcctgc tcctggtgtg    900
attcgcaggc acctcagatt ctctgttact gcagtccttt ctggaccggc agctacatcc    960
tggccaactt tgacagcagc cgttccggca aggacacaaa caccctcctg ggaagcatcc    1020
acacctttga tcctgaggct ggatgcgacg actccacctt ccagccctgc tccccgcgtg    1080
cgctcgccaa ccataaggag gttgtagact cttttccgctc gatctatact ctcaacgatg    1140
gtctcagtga cagtgaggcg gttgcggtcg gtcggtaccc tgaggatagc tactacaacg    1200
gcaacccgtg gttcctgtgc accttggctg ccgcggaaca gctgtacgat gctctgtacc    1260
agtgggacaa gcaggggtcg ttggagatca cagacgtgtc acttgacttc ttcaaggctc    1320
tgtacagtgg tgctgccacc ggcacgtact cttcgtccag ctcgacctat agcagcattg    1380
tgagtgccgt caagactttc gctgatggtt ttgtttctat tgtggtaagt ctacgctaga    1440
cgagcgctca tatttacaga gggtgcgtac taacaggatt aggaaactca cgccgcaagc    1500
aacggctctc tgtctgagca attcgacaag tctgatggcg acgagctttc tgctcgcgat    1560
ctgacctggt cttacgctgc tctgctgacc gccaacaacc gtcgtaattc tgtcgtgccc    1620
ccgtcttggg gtgagacctc tgccagcagc gtgcccggca ctgtgcggc tacctctgcc     1680
tctggtacct acagcagtgt gaccgtcacc tcgtggccga gcatcgtggc tactggtggc    1740
accactacga cggctactac cactggatcg ggcggcgtga cctcgaccag caagaccacc    1800
acaactgcta gtaagaccag caccactacg tcctcgacct cctgcaccac ccccactgcc    1860
gtagctgtga ccttttgatct gacggcgacc accacctacg gcgagaacat ctacctggtc    1920
gggtcgatct ctcagctcgg tgactgggag accagcgatg gcatagctct gagcgctgac    1980
aagtacactt ccagcaaccc gctttggtat gtaactgtga ctctgccggc tggtgagtca    2040
tttgagtaca agttcatccg cgtcgagagc gatgactccg tggagtggga gagcgacccg    2100
aaccgggaat acaccgttcc tcaggcgtgc ggcgagtcga ccgcgacggt gaccgacacc    2160
tggcggtag                                                          2169
```

<210> SEQ ID NO 5
<211> LENGTH: 639
<212> TYPE: PRT
<213> ORGANISM: Aspergillus awamori var. kawachi

<400> SEQUENCE: 5

Met Ser Phe Arg Ser Leu Leu Ala Leu Ser Gly Leu Val Cys Ser Gly
1               5                   10                  15

Leu Ala Ser Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Asp Ser Gly Ile Val Val Ala Ser
    50                  55                  60

Pro Ser Thr Asp Asn Pro Asp Tyr Phe Tyr Thr Trp Thr Arg Asp Ser
 65                  70                  75                  80

Gly Leu Val Ile Lys Thr Leu Val Asp Leu Phe Arg Asn Gly Asp Thr
                 85                  90                  95

Asp Leu Leu Ser Thr Ile Glu His Tyr Ile Ser Ser Gln Ala Ile Ile
            100                 105                 110

Gln Gly Val Ser Asn Pro Ser Gly Asp Leu Ser Ser Gly Gly Leu Gly
        115                 120                 125

Glu Pro Lys Phe Asn Val Asp Glu Thr Ala Tyr Thr Gly Ser Trp Gly
    130                 135                 140

Arg Pro Gln Arg Asp Gly Pro Ala Leu Arg Ala Thr Ala Met Ile Gly
145                 150                 155                 160

Phe Gly Gln Trp Leu Leu Asp Asn Gly Tyr Thr Ser Ala Ala Thr Glu
                165                 170                 175

Ile Val Trp Pro Leu Val Arg Asn Asp Leu Ser Tyr Val Ala Gln Tyr
            180                 185                 190

Trp Asn Gln Thr Gly Tyr Asp Leu Trp Glu Glu Val Asn Gly Ser Ser
        195                 200                 205

Phe Phe Thr Ile Ala Val Gln His Arg Ala Leu Val Glu Gly Ser Ala
    210                 215                 220

Phe Ala Thr Ala Val Gly Ser Ser Cys Ser Trp Cys Asp Ser Gln Ala
225                 230                 235                 240

Pro Gln Ile Leu Cys Tyr Leu Gln Ser Phe Trp Thr Gly Ser Tyr Ile
                245                 250                 255

Leu Ala Asn Phe Asp Ser Ser Arg Ser Gly Lys Asp Thr Asn Thr Leu
            260                 265                 270

Leu Gly Ser Ile His Thr Phe Asp Pro Glu Ala Gly Cys Asp Asp Ser
        275                 280                 285

Thr Phe Gln Pro Cys Ser Pro Arg Ala Leu Ala Asn His Lys Glu Val
    290                 295                 300

Val Asp Ser Phe Arg Ser Ile Tyr Thr Leu Asn Asp Gly Leu Ser Asp
305                 310                 315                 320

Ser Glu Ala Val Ala Val Gly Arg Tyr Pro Glu Asp Ser Tyr Tyr Asn
                325                 330                 335

Gly Asn Pro Trp Phe Leu Cys Thr Leu Ala Ala Ala Glu Gln Leu Tyr
            340                 345                 350

Asp Ala Leu Tyr Gln Trp Asp Lys Gln Gly Ser Leu Glu Ile Thr Asp
        355                 360                 365

Val Ser Leu Asp Phe Phe Lys Ala Leu Tyr Ser Gly Ala Ala Thr Gly
    370                 375                 380

Thr Tyr Ser Ser Ser Ser Thr Tyr Ser Ser Ile Val Ser Ala Val
385                 390                 395                 400

Lys Thr Phe Ala Asp Gly Phe Val Ser Ile Val Glu Thr His Ala Ala
                405                 410                 415

Ser Asn Gly Ser Leu Ser Glu Gln Phe Asp Lys Ser Asp Gly Asp Glu
            420                 425                 430

Leu Ser Ala Arg Asp Leu Thr Trp Ser Tyr Ala Ala Leu Leu Thr Ala
        435                 440                 445

Asn Asn Arg Arg Asn Ser Val Val Pro Pro Ser Trp Gly Glu Thr Ser
    450                 455                 460

Ala Ser Ser Val Pro Gly Thr Cys Ala Ala Thr Ser Ala Ser Gly Thr
465                 470                 475                 480

Tyr Ser Ser Val Thr Val Thr Ser Trp Pro Ser Ile Val Ala Thr Gly

```
            485                 490                 495
Gly Thr Thr Thr Thr Ala Thr Thr Thr Gly Ser Gly Gly Val Thr Ser
            500                 505                 510

Thr Ser Lys Thr Thr Thr Thr Ala Ser Lys Thr Ser Thr Thr Thr Ser
            515                 520                 525

Ser Thr Ser Cys Thr Thr Pro Thr Ala Val Ala Val Thr Phe Asp Leu
            530                 535                 540

Thr Ala Thr Thr Thr Tyr Gly Glu Asn Ile Tyr Leu Val Gly Ser Ile
545                 550                 555                 560

Ser Gln Leu Gly Asp Trp Glu Thr Ser Asp Gly Ile Ala Leu Ser Ala
            565                 570                 575

Asp Lys Tyr Thr Ser Ser Asn Pro Leu Trp Tyr Val Thr Val Thr Leu
            580                 585                 590

Pro Ala Gly Glu Ser Phe Glu Tyr Lys Phe Ile Arg Val Glu Ser Asp
            595                 600                 605

Asp Ser Val Glu Trp Glu Ser Asp Pro Asn Arg Glu Tyr Thr Val Pro
            610                 615                 620

Gln Ala Cys Gly Glu Ser Thr Ala Thr Val Thr Asp Thr Trp Arg
625                 630                 635

<210> SEQ ID NO 6
<211> LENGTH: 615
<212> TYPE: PRT
<213> ORGANISM: Aspergillus awamori var. kawachi

<400> SEQUENCE: 6

Ala Thr Leu Asp Ser Trp Leu Ser Asn Glu Ala Thr Val Ala Arg Thr
 1               5                  10                  15

Ala Ile Leu Asn Asn Ile Gly Ala Asp Gly Ala Trp Val Ser Gly Ala
             20                  25                  30

Asp Ser Gly Ile Val Val Ala Ser Pro Ser Thr Asp Asn Pro Asp Tyr
         35                  40                  45

Phe Tyr Thr Trp Thr Arg Asp Ser Gly Leu Val Ile Lys Thr Leu Val
 50                  55                  60

Asp Leu Phe Arg Asn Gly Asp Thr Asp Leu Leu Ser Thr Ile Glu His
 65                  70                  75                  80

Tyr Ile Ser Ser Gln Ala Ile Ile Gln Gly Val Ser Asn Pro Ser Gly
             85                  90                  95

Asp Leu Ser Ser Gly Gly Leu Gly Glu Pro Lys Phe Asn Val Asp Glu
            100                 105                 110

Thr Ala Tyr Thr Gly Ser Trp Gly Arg Pro Gln Arg Asp Gly Pro Ala
        115                 120                 125

Leu Arg Ala Thr Ala Met Ile Gly Phe Gly Gln Trp Leu Leu Asp Asn
130                 135                 140

Gly Tyr Thr Ser Ala Ala Thr Glu Ile Val Trp Pro Leu Val Arg Asn
145                 150                 155                 160

Asp Leu Ser Tyr Val Ala Gln Tyr Trp Asn Gln Thr Gly Tyr Asp Leu
            165                 170                 175

Trp Glu Glu Val Asn Gly Ser Ser Phe Phe Thr Ile Ala Val Gln His
            180                 185                 190

Arg Ala Leu Val Glu Gly Ser Ala Phe Ala Thr Ala Val Gly Ser Ser
        195                 200                 205

Cys Ser Trp Cys Asp Ser Gln Ala Pro Gln Ile Leu Cys Tyr Leu Gln
210                 215                 220
```

-continued

Ser Phe Trp Thr Gly Ser Tyr Ile Leu Ala Asn Phe Asp Ser Ser Arg
225                 230                 235                 240

Ser Gly Lys Asp Thr Asn Thr Leu Leu Gly Ser Ile His Thr Phe Asp
            245                 250                 255

Pro Glu Ala Gly Cys Asp Asp Ser Thr Phe Gln Pro Cys Ser Pro Arg
            260                 265                 270

Ala Leu Ala Asn His Lys Glu Val Val Asp Ser Phe Arg Ser Ile Tyr
            275                 280                 285

Thr Leu Asn Asp Gly Leu Ser Asp Ser Glu Ala Val Ala Val Gly Arg
        290                 295                 300

Tyr Pro Glu Asp Ser Tyr Tyr Asn Gly Asn Pro Trp Phe Leu Cys Thr
305                 310                 315                 320

Leu Ala Ala Ala Glu Gln Leu Tyr Asp Ala Leu Tyr Gln Trp Asp Lys
                325                 330                 335

Gln Gly Ser Leu Glu Ile Thr Asp Val Ser Leu Asp Phe Phe Lys Ala
            340                 345                 350

Leu Tyr Ser Gly Ala Ala Thr Gly Thr Tyr Ser Ser Ser Ser Ser Thr
            355                 360                 365

Tyr Ser Ser Ile Val Ser Ala Val Lys Thr Phe Ala Asp Gly Phe Val
370                 375                 380

Ser Ile Val Glu Thr His Ala Ala Ser Asn Gly Ser Leu Ser Glu Gln
385                 390                 395                 400

Phe Asp Lys Ser Asp Gly Asp Glu Leu Ser Ala Arg Asp Leu Thr Trp
                405                 410                 415

Ser Tyr Ala Ala Leu Leu Thr Ala Asn Asn Arg Arg Asn Ser Val Val
            420                 425                 430

Pro Pro Ser Trp Gly Glu Thr Ser Ala Ser Ser Val Pro Gly Thr Cys
            435                 440                 445

Ala Ala Thr Ser Ala Ser Gly Thr Tyr Ser Ser Val Thr Val Thr Ser
            450                 455                 460

Trp Pro Ser Ile Val Ala Thr Gly Gly Thr Thr Thr Thr Ala Thr Thr
465                 470                 475                 480

Thr Gly Ser Gly Gly Val Thr Ser Thr Ser Lys Thr Thr Thr Thr Ala
                485                 490                 495

Ser Lys Thr Ser Thr Thr Thr Ser Ser Thr Ser Cys Thr Thr Pro Thr
            500                 505                 510

Ala Val Ala Val Thr Phe Asp Leu Thr Ala Thr Thr Thr Tyr Gly Glu
            515                 520                 525

Asn Ile Tyr Leu Val Gly Ser Ile Ser Gln Leu Gly Asp Trp Glu Thr
            530                 535                 540

Ser Asp Gly Ile Ala Leu Ser Ala Asp Lys Tyr Thr Ser Ser Asn Pro
545                 550                 555                 560

Leu Trp Tyr Val Thr Val Thr Leu Pro Ala Gly Glu Ser Phe Glu Tyr
                565                 570                 575

Lys Phe Ile Arg Val Glu Ser Asp Ser Val Glu Trp Glu Ser Asp Pro
            580                 585                 590

Pro Asn Arg Glu Tyr Thr Val Pro Gln Ala Cys Gly Glu Ser Thr Ala
            595                 600                 605

Thr Val Thr Asp Thr Trp Arg
        610                 615

<210> SEQ ID NO 7
<211> LENGTH: 28
<212> TYPE: DNA

```
<213> ORGANISM: Artificial Sequence
<220> FEATURE:
<223> OTHER INFORMATION: primer

<400> SEQUENCE: 7
caacatgcat accttctcca agctcctc                                              28

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
ttaacgccac gaatcattca ccgtc                                                 25

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
caccatgtcg ttccgatctc ttctc                                                 25

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
ctaccgccag gtgtcggtca c                                                     21

<210> SEQ ID NO 11
<211> LENGTH: 10739
<212> TYPE: DNA
<213> ORGANISM: Artificial Sequence
<220> FEATURE:
<223> OTHER INFORMATION: constructed pTrex3g_N13 plasmid

<400> SEQUENCE: 11
aagcttacta gtacttctcg agctctgtac atgtccggtc gcgacgtacg cgtatcgatg           60
gcgccagctg caggcggccg cctgcagcca cttgcagtcc cgtggaattc tcacggtgaa          120
tgtaggcctt ttgtagggta ggaattgtca ctcaagcacc cccaacctcc attacgcctc          180
ccccatagag ttcccaatca gtgagtcatg gcactgttct caaatagatt ggggagaagt          240
tgacttccgc ccagagctga aggtcgcaca accgcatgat atagggtcgg caacggcaaa          300
aaagcacgtg gctcaccgaa agcaagatg tttgcgatct aacatccagg aacctggata           360
catccatcat cacgcacgac cactttgatc tgctggtaaa ctcgtattcg ccctaaaccg          420
aagtgcgtgg taaatctaca cgtgggcccc tttcggtata ctgcgtgtgt cttctctagg          480
tgccattctt ttcccttcct ctagtgttga attgtttgtg ttggagtccg agctgtaact          540
acctctgaat ctctggagaa tggtggacta acgactaccg tgcacctgca tcatgtatat          600
aatagtgatc ctgagaaggg ggttttggag caatgtggga ctttgatggt catcaaacaa          660
agaacgaaga cgcctctttt gcaaagtttt gtttcggcta cggtgaagaa ctggatactt          720
gttgtgtctt ctgtgtattt ttgtggcaac aagaggccag agacaatcta ttcaaacacc          780
```

```
aagcttgctc ttttgagcta caagaacctg tggggtatat atctagagtt gtgaagtcgg    840
taatcccgct gtatagtaat acgagtcgca tctaaatact ccgaagctgc tgcgaacccg    900
gagaatcgag atgtgctgga aagcttctag cgagcggcta aattagcatg aaaggctatg    960
agaaattctg gagacggctt gttgaatcat ggcgttccat tcttcgacaa gcaaagcgtt   1020
ccgtcgcagt agcaggcact cattcccgaa aaaactcgga gattcctaag tagcgatgga   1080
accggaataa tataataggc aatacattga gttgcctcga cggttgcaat gcaggggtac   1140
tgagcttgga cataactgtt ccgtacccca cctcttctca acctttggcg tttccctgat   1200
tcagcgtacc cgtacaagtc gtaatcacta ttaacccaga ctgaccggac gtgttttgcc   1260
cttcatttgg agaaataatg tcattgcgat gtgtaatttg cctgcttgac cgactggggc   1320
tgttcgaagc ccgaatgtag gattgttatc cgaactctgc tcgtagaggc atgttgtgaa   1380
tctgtgtcgg gcaggacacg cctcgaaggt tcacggcaag ggaaaccacc gatagcagtg   1440
tctagtagca acctgtaaag ccgcaatgca gcatcactgg aaaatacaaa ccaatggcta   1500
aaagtacata agttaatgcc taaagaagtc atataccagc ggctaataat tgtacaatca   1560
agtggctaaa cgtaccgtaa tttgccaacg gcttgtgggg ttgcagaagc aacggcaaag   1620
ccccacttcc ccacgtttgt ttcttcactc agtccaatct cagctggtga tcccccaatt   1680
gggtcgcttg tttgttccgg tgaagtgaaa gaagacagag gtaagaatgt ctgactcgga   1740
gcgttttgca tacaaccaag ggcagtgatg aagacagtg aaatgttgac attcaaggag   1800
tatttagcca gggatgcttg agtgtatcgt gtaaggaggt ttgtctgccg atacgacgaa   1860
tactgtatag tcacttctga tgaagtggtc catattgaaa tgtaaagtcg gcactgaaca   1920
ggcaaaagat tgagttgaaa ctgcctaaga tctcgggccc tcgggccttc ggcctttggg   1980
tgtacatgtt tgtgctccgg gcaaatgcaa agtgtggtag gatcgaacac actgctgcct   2040
ttaccaagca gctgagggta tgtgataggc aaatgttcag gggccactgc atggtttcga   2100
atagaaagag aagcttagcc aagaacaata gccgataaag atagcctcat taaacggaat   2160
gagctagtag gcaaagtcag cgaatgtgta tatataaagg ttcgaggtcc gtgcctccct   2220
catgctctcc ccatctactc atcaactcag atcctccagg agacttgtac accatctttt   2280
gaggcacaga aacccaatag tcaaccatca caagtttgta caaaaaagca ggctccgcgg   2340
ccgcccccTT caacatgcat accttctcca agctcctcgt cctgggctct gccgtccagt   2400
ctgccctcgg gcggcctcac ggctcttcgc gtctccagga acgcgctgcc gttgatacct   2460
tcatcaacac cgagaagccc atcgcatgga acaagctgct cgccaacatc ggccctaacg   2520
gcaaagccgc tcccggtgcc gccgccggcg ttgtgattgc cagcccttcc aggacggacc   2580
ctccttgtac gtggtggcat ggaatggacc caagagactg gttttagatg aaagagagtt   2640
tctgctaacc gccacaccca gacttcttca cctggacccg cgatgccgcc ctggtcctca   2700
ccggcatcat cgagtccctt ggccacaact acaacaccac cctgcagacc gtcatccaga   2760
actacgtcgc gtcgcaggcc aagctgcagc aggtctcgaa cccctcggga accttcgccg   2820
acggctcggg tctcggtgag gccaagttca atgtcgacct cactgccttc actggcgaat   2880
ggggtcgccc tcagagggac ggcccgcccc tgcgcgccat cgctctcatc cagtacgcca   2940
agtggctgat cgccaacggc tacaagagca cggccaagag cgtcgtctgg cccgtcgtca   3000
agaacgatct cgcctacacg gcccagtact ggaacgagac cggcttcgat ctctgggagg   3060
aggtccccgg cagctcgttc tttaccatcg ccagctctca caggggtgag tcatttattg   3120
```

```
ttcagtgttt tctcattgaa taattaccgg aatgccactg acgccaaaca gctctgactg    3180
agggtgctta cctcgccgct cagctcgaca ccgagtgccg cgcctgcacg accgtcgccc    3240
ctcaggttct gtgcttccag caggccttct ggaactccaa gggcaactat gtcgtctcca    3300
acagtaagat ccctacacca acaaaaaaaa tcgaaaagga acgttagctg acccttctag    3360
tcaacggcgg cgagtatcgc tccggcaagg acgccaactc gatcctggcg tccatccaca    3420
acttcgaccc tgaggccggc tgcgacaacc tgaccttcca gccctgcagc gagcgcgccc    3480
tggccaacca caaggcctat gtcgactcgt tccgcaacct ctacgccatc aacaagggca    3540
tcgcccaggg caaggccgtt gccgtcggcc gctactcgga ggatgtctac tacaacggca    3600
acccgtggta cctggccaac tttgccgccg ccgagcagct ctacgacgcc atctacgtgt    3660
ggaacaagca gggctccatc accgtgacct cggtctccct gcccttcttc cgcgaccttg    3720
tctcgtcggt cagcaccggc acctactcca agagcagctc gaccttcacc aacatcgtca    3780
acgccgtcaa ggcctacgcc gacggcttca tcgaggtggc ggccaagtac accccgtcca    3840
acggcgcgct cgccgagcag tacgaccgca acacgggcaa gcccgactcg gccgccgacc    3900
tgacgtggtc gtactcggcc ttcctctcgg ccatcgaccg ccgcgcgggt ctcgtccccc    3960
cgagctggcg ggccagcgtg gccaagagcc agctgccgtc cacctgctcg cgcatcgagg    4020
tcgccggcac ctacgtcgcc gccacgagca cctcgttccc gtccaagcag accccgaacc    4080
cctccgcggc gccctccccg tcccctaccc gaccgcctg cgcggacgct agcgaggtgt    4140
acgtcacctt caacgagcgc gtgtcgaccg cgtggggcga gaccatcaag gtggtgggca    4200
acgtgccggc gctggggaac tgggacacgt ccaaggcggt gaccctgtcg gccagcgggt    4260
acaagtcgaa tgatcccctc tggagcatca cggtgcccat caaggcgacg ggctcggccg    4320
tgcagtacaa gtatatcaag gtcggcacca acggggaagat tacttgggag tcggaccca    4380 acaggagcat taccctgcag acggcgtcgt ctgcgggcaa gtgcgccgcg cagacggtga    4440
atgattcgtg gcgttaaaag ggtgggcgcg ccgacccagc tttcttgtac aaagtggtga    4500
tcgcgccagc tccgtgcgaa agcctgacgc accggtagat tcttggtgag cccgtatcat    4560
gacggcggcg ggagctacat ggccccgggt gatttatttt ttttgtatct acttctgacc    4620
cttttcaaat atacggtcaa ctcatctttc actggagatg cggcctgctt ggtattgcga    4680
tgttgtcagc ttggcaaatt gtggctttcg aaaacacaaa acgattcctt agtagccatg    4740
cattttaaga taacggaata gaagaaagag gaaattaaaa aaaaaaaaaa aacaaacatc    4800
ccgttcataa cccgtagaat cgccgctctt cgtgtatccc agtaccagtt tattttgaat    4860
agctcgcccg ctggagagca tcctgaatgc aagtaacaac cgtagaggct gacacggcag    4920
gtgttgctag ggagcgtcgt gttctacaag gccagacgtc ttcgcggttg atatatatgt    4980
atgtttgact gcaggctgct cagcgacgac agtcaagttc gccctcgctg cttgtgcaat    5040
aatcgcagtg gggaagccac accgtgactc ccatctttca gtaaagctct gttggtgttt    5100
atcagcaata cacgtaattt aaactcgtta gcatggggct gatagcttaa ttaccgttta    5160
ccagtgccat ggttctgcag ctttccttgg cccgtaaaat tcggcgaagc cagccaatca    5220
ccagctaggc accagctaaa ccctataatt agtctcttat caacaccatc cgctcccccg    5280
ggatcaatga ggagaatgag ggggatgcgg ggctaaagaa gcctacataa ccctcatgcc    5340
aactcccagt ttacactcgt cgagccaaca tcctgactat aagctaacac agaatgcctc    5400
aatcctggga agaactggcc gctgataagc gcgcccgcct cgcaaaaacc atccctgatg    5460
aatggaaagt ccagacgctg cctgcggaag acagcgttat tgatttccca aagaaatcgg    5520
```

```
ggatcctttc agaggccgaa ctgaagatca cagaggcctc cgctgcagat cttgtgtcca    5580
agctggcggc cggagagttg acctcggtgg aagttacgct agcattctgt aaacgggcag    5640
caatcgccca gcagttagta gggtcccctc tacctctcag ggagatgtaa caacgccacc    5700
ttatgggact atcaagctga cgctggcttc tgtgcagaca aactgcgccc acgagttctt    5760
ccctgacgcc gctctcgcgc aggcaaggga actcgatgaa tactacgcaa agcacaagag    5820
acccgttggt ccactccatg gcctcccccat ctctctcaaa gaccagcttc gagtcaaggt    5880
acaccgttgc ccctaagtcg ttagatgtcc cttttttgtca gctaacatat gccaccaggg   5940
ctacgaaaca tcaatgggct acatctcatg gctaaacaag tacgacgaag gggactcggt    6000
tctgacaacc atgctccgca aagccggtgc cgtcttctac gtcaagacct ctgtcccgca    6060
gaccctgatg gtctgcgaga cagtcaacaa catcatcggg cgcaccgtca acccacgcaa    6120
caagaactgg tcgtgcggcg gcagttctgg tggtgagggt gcgatcgttg ggattcgcrv    6180
tggtggcgtc atcggtgtag gaacggatat cggtggctcg attcgagtgc cggccgcgtt    6240
caacttcctg tacggtctaa ggccgagtca tgggcggctg ccgtatgcaa agatggcgaa    6300
cagcatggag ggtcaggaga cggtgcacag cgttgtcggg ccgattacgc actctgttga    6360
gggtgagtcc ttcgcctctt ccttcttttc ctgctctata ccaggcctcc actgtcctcc    6420
tttcttgctt tttatactat atacgagacc ggcagtcact gatgaagtat gttagacctc    6480
cgcctcttca ccaaatccgt cctcggtcag gagccatgga aatacgactc caaggtcatc    6540
cccatgccct ggcgccagtc cgagtcggac attattgcct ccaagatcaa gaacggcggg    6600
ctcaatatcg gctactacaa cttcgacggc aatgtccttc cacaccctcc tatcctgcgc    6660
ggcgtggaaa ccaccgtcgc cgcactcgcc aaagccggtc acaccgtgac cccgtggacg    6720
ccatacaagc acgatttcgg ccacgatctc atctcccata tctacgcggc tgacggcagc    6780
crvgccgacg taatgcgcga tatcagtgca tccggcgagc cggcgattcc aaatatcaaa    6840
gacctactga acccgaacat caaagctgtt aacatgaacg agctctggga cacgcatctc    6900
cagaagtgga attaccagat ggagtacctt gagaaatggc gggaggctga agaaaaggcc    6960
gggaaggaac tggacgccat catcgcgccg attacgccta ccgctgcggt acggcatgac    7020
cagttccggt actatgggta tgcctctgtg atcaacctgc tggatttcac gagcgtggtt    7080
gttccggtta cctttgcgga taagaacatc gataagaaga tgagagtttt caaggcggtt    7140
agtgagcttg atgccctcgt gcaggaagag tatgatccgg aggcgtacca tggggcaccg    7200
gttgcagtgc aggttatcgg acggagactc agtgaagaga ggacgttggc gattgcagag    7260
gaagtgggga agttgctggg aaatgtggtg actccatagc taataagtgt cagatagcaa    7320
tttgcacaag aaatcaatac cagcaactgt aaataagcgc tgaagtgacc atgccatgct    7380
acgaaagagc agaaaaaaac ctgccgtaga accgaagaga tatgacacgc ttccatctct    7440
caaaggaaga atcccttcag ggttgcgttt ccagtctaga cacgtataac ggcacaagtg    7500
tctctcacca aatgggttat atctcaaatg tgatctaagg atggaaagcc cagaatatcg    7560
atcgcgcgca gatccatata tagggcccgg gttataatta cctcaggtcg acgtcccatg    7620
gccattcgaa ttcgtaatca tggtcatagc tgtttcctgt gtgaaattgt tatccgctca    7680
caattccaca acatacgagc cggaagcata aagtgtaaag cctggggtgc ctaatgagt    7740
tgagctaact cacattaatt gcgttgcgct cactgcccgc tttccagtcg ggaaacctgt    7800
cgtgccagct gcattaatga atcggccaac gcgcggggag aggcggtttg cgtattgggc    7860
```

```
gctcttccgc ttcctcgctc actgactcgc tgcgctcggt cgttcggctg cggcgagcgg    7920
tatcagctca ctcaaaggcg gtaatacggt tatccacaga atcaggggat aacgcaggaa    7980
agaacatgtg agcaaaaggc cagcaaaagg ccaggaaccg taaaaaggcc gcgttgctgg    8040
cgtttttcca taggctccgc cccctgacg agcatcacaa aaatcgacgc tcaagtcaga     8100
ggtggcgaaa cccgacagga ctataaagat accaggcgtt tccccctgga agctccctcg    8160
tgcgctctcc tgttccgacc ctgccgctta ccggatacct gtccgccttt ctcccttcgg    8220
gaagcgtggc gctttctcat agctcacgct gtaggtatct cagttcggtg taggtcgttc    8280
gctccaagct gggctgtgtg cacgaacccc ccgttcagcc cgaccgctgc gccttatccg    8340
gtaactatcg tcttgagtcc aacccggtaa gacacgactt atcgccactg gcagcagcca    8400
ctggtaacag gattagcaga gcgaggtatg taggcggtgc tacagagttc ttgaagtggt    8460
ggcctaacta cggctacact agaagaacag tatttggtat ctgcgctctg ctgaagccag    8520
ttaccttcgg aaaaagagtt ggtagctctt gatccggcaa acaaaccacc gctggtagcg    8580
gtggtttttt tgtttgcaag cagcagatta cgcgcagaaa aaaaggatct caagaagatc    8640
ctttgatctt ttctacgggg tctgacgctc agtggaacga aaactcacgt taagggattt    8700
tggtcatgag attatcaaaa aggatcttca cctagatcct tttaaattaa aaatgaagtt    8760
ttaaatcaat ctaaagtata tatgagtaaa cttggtctga cagttaccaa tgcttaatca    8820
gtgaggcacc tatctcagcg atctgtctat ttcgttcatc catagttgcc tgactccccg    8880
tcgtgtagat aactacgata cgggagggct taccatctgg ccccagtgct gcaatgatac    8940
cgcgagaccc acgctcaccg gctccagatt tatcagcaat aaaccagcca gccggaaggg    9000
ccgagcgcag aagtggtcct gcaactttat ccgcctccat ccagtctatt aattgttgcc    9060
gggaagctag agtaagtagt tcgccagtta atagtttgcg caacgttgtt gccattgcta    9120
caggcatcgt ggtgtcacgc tcgtcgtttg gtatggcttc attcagctcc ggttcccaac    9180
gatcaaggcg agttacatga tcccccatgt tgtgcaaaaa agcggttagc tccttcggtc    9240
ctccgatcgt tgtcagaagt aagttggccg cagtgttatc actcatggtt atggcagcac    9300
tgcataattc tcttactgtc atgccatccg taagatgctt ttctgtgact ggtgagtact    9360
caaccaagtc attctgagaa tagtgtatgc ggcgaccgag ttgctcttgc ccggcgtcaa    9420
tacgggataa taccgcgcca catagcagaa ctttaaaagt gctcatcatt ggaaaacgtt    9480
cttcggggcg aaaactctca aggatcttac cgctgttgag atccagttcg atgtaaccca    9540
ctcgtgcacc caactgatct tcagcatctt ttactttcac cagcgtttct gggtgagcaa    9600
aaacaggaag gcaaaatgcc gcaaaaaagg gaataagggc gacacggaaa tgttgaatac    9660
tcatactctt cctttttcaa tattattgaa gcatttatca gggttattgt ctcatgagcg    9720
gatacatatt tgaatgtatt tagaaaaata aacaataggg gttccgcgc acatttcccc     9780 gaaaagtgcc acctgacgtc taagaaacca ttattatcat gacattaacc tataaaaata    9840
ggcgtatcac gaggcccttt cgtctcgcgc gtttcggtga tgacggtgaa aacctctgac    9900
acatgcagct cccggagacg gtcacagctt gtctgtaagc ggatgccggg agcagacaag    9960
cccgtcaggg cgcgtcagcg ggtgttggcg ggtgtcgggg ctggcttaac tatgcggcat    10020
cagagcagat tgtactgaga gtgcaccata aaattgtaaa cgttaatatt tgttaaaat    10080 tcgcgttaaa tttttgttaa atcagctcat tttttaacca ataggccgaa atcggcaaaa    10140
tcccttataa atcaaaagaa tagcccgaga taggggtgag tgttgttcca gtttggaaca    10200
agagtccact attaaagaac gtggactcca acgtcaaagg gcgaaaaacc gtctatcagg    10260
```

```
gcgatggccc actacgtgaa ccatcaccca aatcaagttt tttggggtcg aggtgccgta    10320
aagcactaaa tcggaaccct aaagggagcc cccgatttag agcttgacgg ggaaagccgg    10380
cgaacgtggc gagaaaggaa gggaagaaag cgaaaggagc gggcgctagg gcgctggcaa    10440
gtgtagcggt cacgctgcgc gtaaccacca cacccgccgc gcttaatgcg ccgctacagg    10500
gcgcgtacta tggttgcttt gacgtatgcg gtgtgaaata ccgcacagat gcgtaaggag    10560
aaaataccgc atcaggcgcc attcgccatt caggctgcgc aactgttggg aagggcgatc    10620
ggtgcgggcc tcttcgctat tacgccagct ggcgaaaggg ggatgtgctg caaggcgatt    10680
aagttgggta acgccagggt tttcccagtc acgacgttgt aaaacgacgg ccagtgccc     10739
```